(12) United States Patent
Takasuka et al.

(10) Patent No.: US 8,969,629 B2
(45) Date of Patent: Mar. 3, 2015

(54) CYCLIC COMPOUND, PRODUCTION PROCESS THEREOF, RADIATION-SENSITIVE COMPOSITION AND RESIST PATTERN FORMATION METHOD

(75) Inventors: Masaaki Takasuka, Kanagawa (JP); Masatoshi Echigo, Kanagawa (JP); Yu Okada, Kanagawa (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 0 days.

(21) Appl. No.: 13/512,099

(22) PCT Filed: Nov. 25, 2010

(86) PCT No.: PCT/JP2010/006895
§ 371 (c)(1),
(2), (4) Date: May 25, 2012

(87) PCT Pub. No.: WO2011/065004
PCT Pub. Date: Jun. 3, 2011

(65) Prior Publication Data
US 2012/0282546 A1   Nov. 8, 2012

(30) Foreign Application Priority Data

Nov. 27, 2009  (JP) ................. 2009-270652
Nov. 27, 2009  (JP) ................. 2009-270653
Jun. 17, 2010  (JP) ................. 2010-138525

(51) Int. Cl.
| C07C 41/30 | (2006.01) |
| C07C 43/23 | (2006.01) |
| C07C 43/253 | (2006.01) |
| G03F 7/038 | (2006.01) |

(52) U.S. Cl.
USPC .......... 568/722; 568/723; 568/724; 568/726; 568/727

(58) Field of Classification Search
USPC ......... 568/722, 833, 723, 726, 727, 744, 717, 568/720
See application file for complete search history.

(56) References Cited

U.S. PATENT DOCUMENTS

| 4,866,198 | A | * | 9/1989 | Harris | 560/61 |
| 5,143,784 | A | * | 9/1992 | Mita | 428/336 |
| 5,757,034 | A | * | 5/1998 | Ajit | 257/133 |
| 5,804,664 | A | * | 9/1998 | Kennedy et al. | 525/314 |
| 6,093,517 | A | * | 7/2000 | Ito et al. | 430/270.1 |
| 7,993,812 | B2 | * | 8/2011 | Bozano et al. | 430/270.1 |
| 8,530,136 | B2 | * | 9/2013 | Bozano et al. | 430/270.1 |

FOREIGN PATENT DOCUMENTS

| EP | 2 080 750 A1 | | 7/2009 |
| JP | 2000256362 A | * | 9/2000 |
| JP | 2005-326838 A | | 11/2005 |
| JP | 2008-145539 A | | 6/2008 |
| JP | 2009-173623 A | | 8/2009 |
| JP | 2009-244769 A | | 10/2009 |
| JP | 2011028270 A | * | 2/2011 |
| WO | 2008/053974 A1 | | 5/2008 |
| WO | 2008/136372 A1 | | 11/2008 |
| WO | 2009/060869 A1 | | 5/2009 |
| WO | 2009/075308 A1 | | 6/2009 |

OTHER PUBLICATIONS

Oizumi et al, Development of New Negative-tone Molecular Resists Baed on Calixarene for EUV Lithography, Journal of Photopolymer Science and Technology, vol. 21, No. 3, Jan. 1, 2008, pp. 443-449.*
Extended European Search Report and European Search Opinion issued in counterpart European Application No. 10 83 2853.5, dated Jul. 29, 2013 (5 pages).
Nakayama et al., A New Three-Component Photoresist Based on Calix[4]resorcinarene Derivative, a Cross-linker, and a Photo-acid Generator, The Chemical Society of Japan, 71, 2979-2984 (1998), (6 pages).
Chemical Abstracts, 74-Radiation Chem., Photochem & Other Reprogr. Processes, vol. 144, No. 5, 2006, p. 1586, (1 page).
Barrett, E.S. et al., Assembly and Exchange of Resorcinarene Capsules Monitored by Fluorescence Resonance Energy Transfer, Journal of the American Chemical Society, 2007, vol. 129, No. 13, p. 3818-3819 (2 pages).
Hauke, F. et al., Lower rim mono-functionalization of resorcinarenes, Chemical Communications, 2005, No. 33, p. 4164-4166 (3 pages).
International Search Report from the International Bureau of WIPO for International Application No. PCT/JP2010/006895 dated Feb. 8, 2011 (2 pages) and an English translation of the same (2 pages).
"Three-Component Negative-Type Photoresist Based on Calix[4]resorcinarene, a Cross-linker, and a Photo-acid Generator," Ueda et al., American Chemical Society, Chem. Mater., vol. 10, No. 8, 2230-2234 (Jul. 25, 1998), (5 pages).
Office Action issued in counterpart Chinese Application No. 201080053806.7 dated Dec. 27, 2013 and English translation of the same (37 pages).
Office Action issued in corresponding Taiwan Patent Application No. 10320453480 dated Apr. 3, 2014 and English translation of the same (9 pages).
Chinese Office Action issued on Sep. 10, 2014 for Application No. 201080053806.7 and English translation of the same (16 pages).

* cited by examiner

*Primary Examiner* — Amanda C. Walke
(74) *Attorney, Agent, or Firm* — Fitch, Even, Tabin & Flannery, LLP

(57) ABSTRACT

Disclosed are: a cyclic compound which has high solubility in a safe solvent, is highly sensitive, enables the formation of a resist pattern having a good shape, and rarely causes resist pattern collapse; a process for producing the cyclic compound; a radiation-sensitive composition containing the cyclic compound; and a resist pattern formation method using the composition. Specifically disclosed are: a cyclic compound having a specific structure; a process for producing the cyclic compound; a radiation-sensitive composition containing the compound; and a resist pattern formation method using the composition.

6 Claims, No Drawings

CYCLIC COMPOUND, PRODUCTION PROCESS THEREOF, RADIATION-SENSITIVE COMPOSITION AND RESIST PATTERN FORMATION METHOD

CROSS-REFERENCE TO RELATED APPLICATIONS

This application is a U.S. national phase application filed under 35 U.S.C. §371 of International Application PCT/JP2010/006895, filed on Nov. 25, 2010, designating the United States, which claims priority from Japanese Application 2009-270652, filed Nov. 27, 2009; Japanese Application 2009-270653, filed Nov. 27, 2009; and Japanese Application 2010-138525 filed Jun. 17, 2010, which are hereby incorporated herein by reference in their entirety.

TECHNICAL FIELD

This invention relates to a cyclic compound represented by specific chemical structural formula, which is useful as an acid amplification type non-polymer based resist material, a process for producing the same, a radiation-sensitive composition containing the same, and a resist pattern formation method using the composition.

RELATED ART

Conventional typical resist materials are polymer based materials capable of forming amorphous thin films. For example, a line resist pattern of about 45 to 100 nm is formed by irradiating a resist thin film made by coating a solution of polymer resist material such as polymethyl methacrylate, polyhydroxy styrene with an acid dissociation reactive group, or polyalkyl methacrylate on a substrate with ultraviolet, far ultraviolet, electron beam, extreme ultraviolet (EUV), X-ray or the like.

However, since polymer based resists have the molecular weight as large as about 10,000 to 100,000 and also wide molecular weight distribution, in lithography using a polymer based resist, roughness occurs on a fine resist pattern surface, the resist pattern dimension becomes difficult to be controlled, and the yield decreases. Therefore, there is a limitation in miniaturization with lithography using a conventional polymer based resist material. In order to make a finer resist pattern, various low molecular weight resist materials have been disclosed.

For example, although an alkaline development type, negative type radiation-sensitive composition (see JP-A-2005-326838 and JP-A-2008-145539) using a low molecular weight polynuclear polyphenol compound as a main component has been suggested, it has the disadvantages that the heat resistance is not sufficient and the shape of the resulting resist pattern becomes poor.

As a low molecular weight resist material candidate, an alkaline development type, negative type radiation-sensitive composition using a low molecular weight cyclic polyphenol compound (see JP-A-2009-173623 and T. Nakayama, M. Nomura, K. Haga, M. Ueda: 20 Bull. Chem. Soc. Jpn., 71, 2979 (1998)) or a calixresorcinarene compound (see JP-A-2009-173623 and WO2009/060869) as a main component has been suggested. The low molecular weight cyclic polyphenol compound is expected to provide a resist pattern with small molecular size, high resolution and small roughness due to its low molecular weight. Also, the low molecular weight cyclic polyphenol compound provides high heat resistance even with the low molecular weight, by having a rigid cyclic structure in its backbone.

However, the currently disclosed low molecular weight cyclic polyphenol compound and the calixresorcinarene compound both have problems that the solubility in a safe solvent used for the semiconductor production process is low, the sensitivity is low, the shape of the resulting resist pattern is poor, collapse and peeling of the resist pattern are liable to occur, and the like, so improvement of the low molecular weight cyclic polyphenol compound has been desired.

Moreover, the currently disclosed calixresorcinarene compound synthesized from the methoxyphenol and the benzaldehyde derivative (see WO2009/060869) has problems that the solubility in a safe solvent used for the semiconductor production process is low, the heat resistance is poor, the sensitivity is low, the storage stability of the resist solvent is poor, and the like. In addition, since the yield is low and purification by column chromatography is required, it is not practical.

SUMMARY OF THE INVENTION

The object of the invention is to provide a cyclic compound, which has high solubility in a safe solvent, is highly sensitive, enables the formation of a resist pattern having a good shape, and rarely causes resist pattern collapse or peeling, a process for producing the same, a radiation-sensitive composition containing the cyclic compound, and a resist pattern formation method using the radiation-sensitive composition.

The inventors have, as a result of devoted examinations to solve the above problems, found out that a cyclic compound having a specific structure has high solubility in a safe solvent, has high sensitivity, provides a good resist pattern shape, and rarely causes resist pattern collapse or peeling, and reached the invention.

More specifically, the summary of the invention is as follows.

1. A cyclic compound represented by the following formula (1).

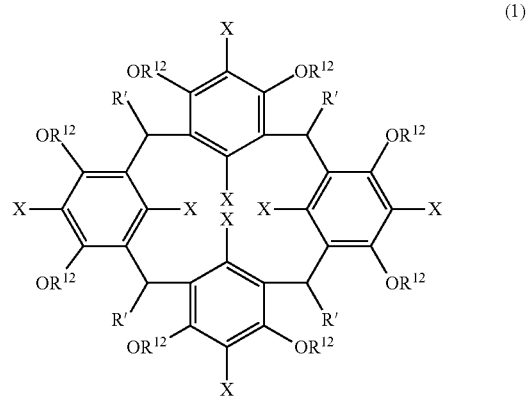

(1)

(In the formula (1), $R^{12}$ is independently a functional group selected from the group consisting of an alkyl group of 6 to 20 carbons, a cycloalkyl group of 3 to 20 carbons, an aryl group of 6 to 20 carbons, an alkylsilyl group of 1 to 20 carbons and an alkyl ester group of 2 to 20 carbons, or a hydrogen atom. (In this regard, at least one of $R^{12}$ among them is a functional group selected from the group consisting of an alkyl group of 6 to 20 carbons, a cycloalkyl group of 3 to 20 carbons, an aryl group of 6 to 20 carbons, an alkylsilyl group of 1 to 20 carbons and an alkyl ester group of 2 to 20 carbons, and at least one other of $R^{12}$ is a hydrogen atom.)

X is independently a functional group selected from the group consisting of a hydrogen atom, an alkyl group of 1 to 20 carbons, a cycloalkyl group of 3 to 20 carbons, an aryl group of 6 to 20 carbons, an alkoxyl group of 1 to 20 carbons, a cyano group, a nitro group, a hydroxyl group, a heterocyclic group, a halogen atom, a carboxyl group, an alkylsilyl group of 1 to 20 carbons and an alkyl ester group of 2 to 20 carbons. R' is independently a functional group selected from the group consisting of an alkyl group of 1 to 20 carbons, an alkyl group of 1 to 20 carbons having a carboxyl group, a cycloalkyl group of 3 to 20 carbons, a cycloalkyl group of 3 to 20 carbons having a carboxyl group, an aryl group of 6 to 20 carbons, an alkoxy group of 1 to 20 carbons, a cyano group, a nitro group, a heterocyclic group, a halogen atom, a carboxyl group, a hydroxyl group, an alkylsilyl group of 1 to 20 carbons and an alkyl ester group of 2 to 20 carbons. (In this regard, at least one of R' is an alkyl group of 1 to 20 carbons having a carboxyl group and/or a hydroxyl group, a cycloalkyl group of 3 to 20 carbons having a carboxyl group and/or a hydroxyl group, or a group represented by the following formula

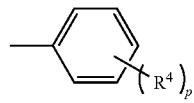

wherein, $R^4$ is a functional group selected from the group consisting of an alkyl group of 1 to 14 carbons, a cycloalkyl group of 3 to 14 carbons, an aryl group of 6 to 14 carbons, an alkoxy group of 1 to 14 carbons, a cyano group, a nitro group, a heterocyclic group, a halogen atom, a carboxyl group, a hydroxyl group, an alkylsilyl group of 1 to 14 carbons and an alkyl ester group of 2 to 14 carbons, at least one of $R^4$ is a hydroxyl group or a carboxyl group, and p is an integer of 1 to 5.))

2. A cyclic compound according to the above item 1, wherein the cyclic compound is a compound represented by the above formula (1), and in the formula (1), at least one of $R^{12}$ is a functional group selected from the group consisting of an alkyl group of 6 to 20 carbons, a cycloalkyl group of 6 to 20 carbons, an aryl group of 6 to 20 carbons, an alkylsilyl group of 1 to 20 carbons and an alkyl ester group of 2 to 20 carbons, and at least one other of $R^{12}$ is a hydrogen atom.

3. A cyclic compound according to the above item 1, wherein the cyclic compound is a compound represented by the following formula (3).

(3)

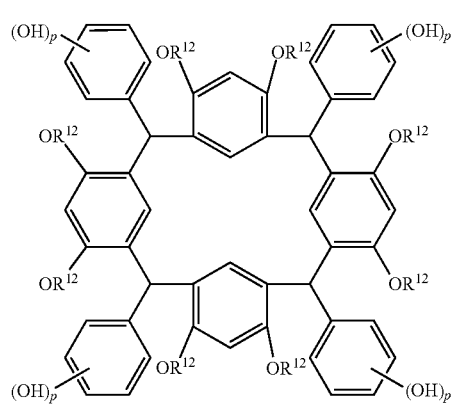

(In the formula (3), $R^{12}$ and p are the same as above.)

4. A cyclic compound according to the above item 3, wherein the cyclic compound is represented by any of the isomers of the following formulae (3-1) to (3-4).

(3-1)

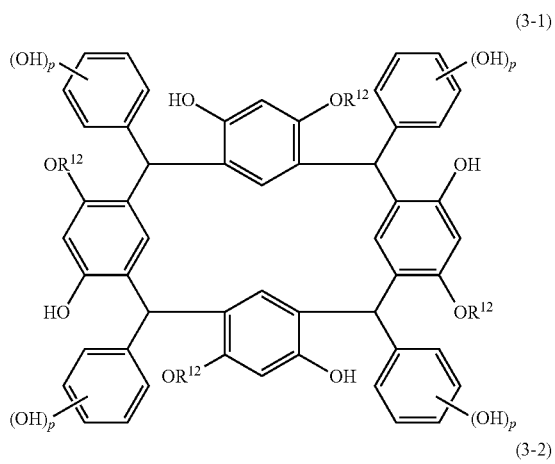

(3-2)

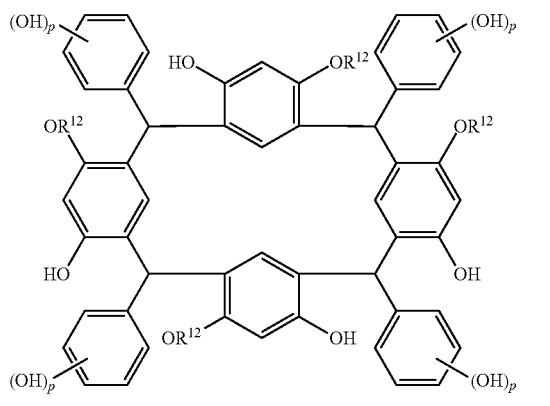

(3-3)

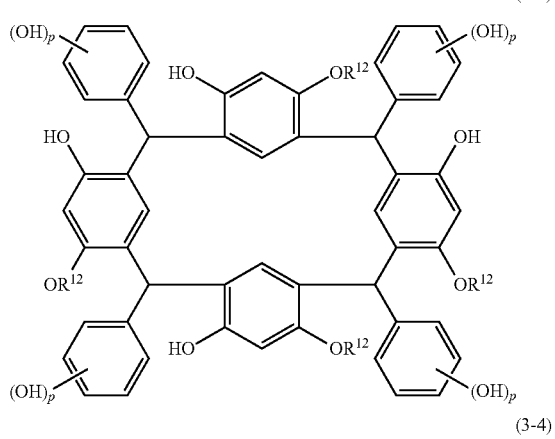

(3-4)

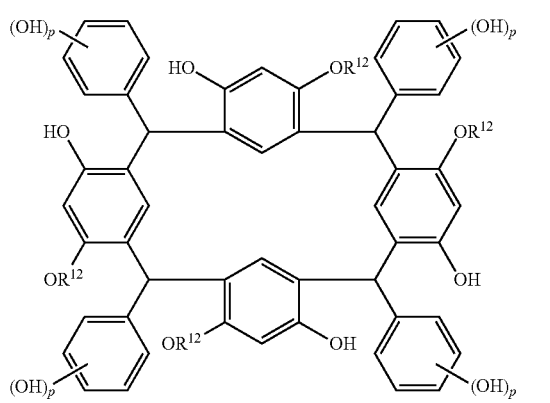

(In the formulae (3-1) to (3-4), $R^{12}$ and p are the same as above.)

5. A cyclic compound according to the above item 3, wherein the cyclic compound is represented by any of the isomers of the following formulae (3'-1) to (3'-4).

(3'-1)

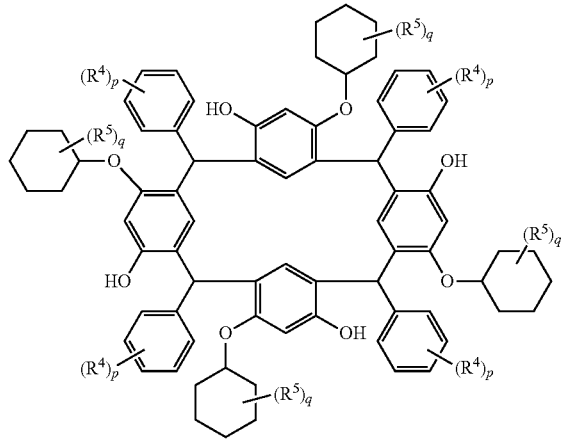

(3'-2)

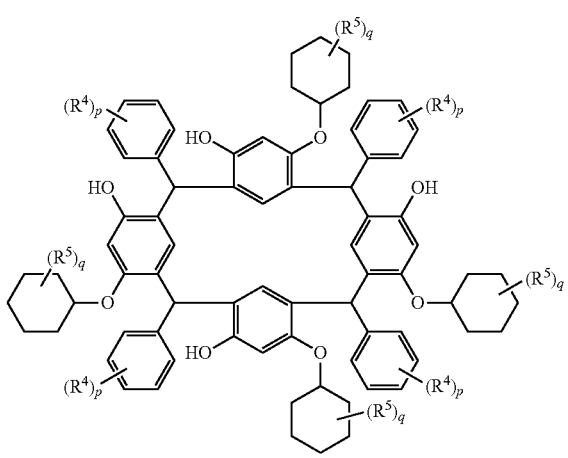

(3'-3)

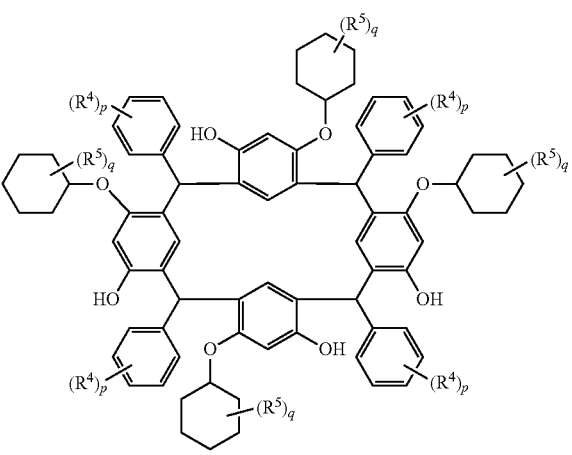

(3'-4)

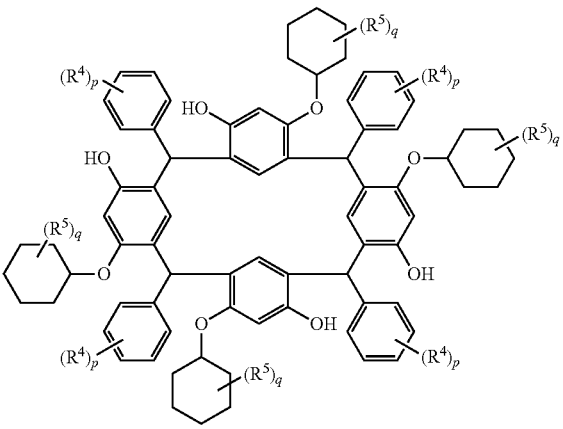

(In the formulae (3'-1) to (3'-4), $R^4$ and p are the same as above. $R^5$ is a functional group selected from the group consisting of an alkyl group of 1 to 3 carbons, a cycloalkyl group of 3 to 6 carbons, an aryl group of 6 to 14 carbons, an alkoxy group of 1 to 14 carbons, a cyano group, a nitro group, a heterocyclic group, a halogen atom, a carboxyl group, a hydroxyl group and an alkylsilyl group of 1 to 14 carbons, or a hydrogen atom, and q is an integer of 0 to 2.)

6. A production process for a cyclic compound (A) represented by the formula (1) comprising a step of conducting a condensation reaction of one or more kinds selected from the group consisting of aromatic carbonyl compound (A1) and one or more kinds selected from the group consisting of phenolic compound (A2).

7. A production process according to the above item 6, wherein the reaction temperature is 0 to 60° C.

8. A radiation-sensitive composition containing a cyclic compound according to the above item 1 and a solvent.

9. A radiation-sensitive composition according to the above item 8 comprising 1 to 80% by weight of solid component and 20 to 99% by weight of solvent.

10. A radiation-sensitive composition according to the above item 8 or 9, wherein the cyclic compound is 50 to 99.999% by weight of the total weight of solid component.

11. A radiation-sensitive composition according to the above item 8, wherein the cyclic compound is a cyclic compound with a molecular weight of 800 to 5500 having at least one phenolic hydroxyl group and having a structure in which a hydrogen atom of at least one phenolic hydroxyl group of a cyclic compound (A) with a molecular weight of 700 to 5000 synthesized by a condensation reaction of a compound (aldehydic compound (A1A)) having 2 to 59 carbons, 1 to 4 formyl groups and 1 to 3 phenolic hydroxyl groups and a compound (phenolic compound (A2)) having 6 to 15 carbons and 1 to 3 phenolic hydroxyl groups, is substituted with an alkyl group of 1 to 20 carbons.

12. A radiation-sensitive composition according to the above item 8 further comprising an acid generating agent (C) generating an acid directly or indirectly by irradiation of any radiation selected from the group consisting of visible light, ultraviolet, excimer laser, electron beam, extreme ultraviolet (EUV), X-ray, and ion beam.

13. A radiation-sensitive composition according to the above item 8 further comprising an acid crosslinking agent (G).

14. A radiation-sensitive composition according to the above item 8 further comprising an acid diffusion controlling agent (E).

15. A radiation-sensitive composition according to the above item 8, wherein the solid component contains cyclic compound/acid generating agent (C)/acid crosslinking agent (G)/acid diffusion controlling agent (E)/optional component (F) in 50 to 99.489/0.001 to 49.49/0.5 to 49.989/0.01 to 49.499/0 to 49.489% by weight based on the solid component.

16. A radiation-sensitive composition according to the above item 8, wherein an amorphous film is formed by spill coating.

17. A radiation-sensitive composition according to the above item 16, wherein the dissolution rate of the amorphous film in 2.38% by weight tetramethylammonium hydroxide aqueous solution at 23° C. is not less than 10 Å/sec.

18. A radiation-sensitive composition according to the above item 16, wherein the dissolution rate of the amorphous film, which is irradiated with KrF excimer laser, extreme ultraviolet, electron beam or X-ray, or heated at 20 to 250° C., in 2.38% by weight tetramethylammonium hydroxide aqueous solution is not more than 5 Å/sec.

19. A resist pattern formation method comprising steps of forming a resist film on a substrate using a radiation-sensitive composition according to the above items 8 to 18, exposing the resist film, and developing the resist film to form a resist pattern.

Effects of the Invention

According to the invention, a cyclic compound, which has high solubility in a safe solvent, is highly sensitivity, enables the formation of a resist pattern having a good shape, and rarely causes resist pattern collapse or peeling, a process for producing the same, a radiation-sensitive composition containing the cyclic compound, and a resist pattern formation method using the radiation-sensitive composition can be provided.

DETAILED DESCRIPTION OF THE PREFERRED EMBODIMENTS

The invention will be descried in details below.

[Cyclic Compound and Production Process Thereof]

The invention relates to a cyclic compound useful as a resist material and a production process thereof.

The cyclic compound of the invention is a cyclic compound represented by the following formula (1).

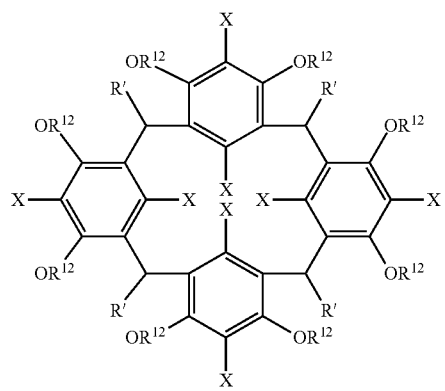

(1)

In the formula (1), $R^{12}$ is independently a functional group selected from the group consisting of an alkyl group of 6 to 20 carbons, a cycloalkyl group of 3 to 20 carbons (preferably a cycloalkyl group of 6 to 12 carbons, more preferably a cyclohexyl group), an aryl group of 6 to 20 carbons, an alkylsilyl group of 1 to 20 carbons and an alkyl ester group of 2 to 20 carbons, or a hydrogen atom. However, at least one of $R^{12}$ thereof is a functional group selected from the group consisting of an alkyl group of 6 to 20 carbons, a cycloalkyl group of 3 to 20 carbons, an aryl group of 6 to 20 carbons, an alkylsilyl group of 1 to 20 carbons and an alkyl ester group of 2 to 20 carbons, and at least one other of $R^{12}$ is preferably a hydrogen atom.

Also, at least one other of $R^{12}$ is preferably a hydrogen atom.

X is independently a functional group selected from the group consisting of a hydrogen atom, an alkyl group of 1 to 20 carbons, a cycloalkyl group of 3 to 20 carbons, an aryl group of 6 to 20 carbons, an alkoxyl group of 1 to 20 carbons, a cyano group, a nitro group, a hydroxyl group, a heterocyclic group, a halogen atom, a carboxyl group, an alkylsilyl group of 1 to 20 carbons, an alkyl ester group of 2 to 20 carbons and a derivative thereof.

R' is independently a functional group selected from the group consisting of an alkyl group of 1 to 20 carbons, an alkyl group of 1 to 20 carbons having a carboxyl group, a cycloalkyl group of 3 to 20 carbons, a cycloalkyl group of 3 to 20 carbons having a carboxyl group, an aryl group of 6 to 20 carbons, an alkoxy group of 1 to 20 carbons, a cyano group, a nitro group, a heterocyclic group, a halogen atom, a carboxyl group, a hydroxyl group, an alkylsilyl group of 1 to 20 carbons, an alkyl ester group of 2 to 20 carbons and a derivative thereof. However, at least one of R' is an alkyl group of 1 to 20 carbons having a carboxyl group and/or a hydroxyl group, a cycloalkyl group of 3 to 20 carbons having a carboxyl group and/or a hydroxyl group, or a group represented by the following formula

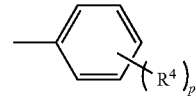

wherein, $R^4$ is a functional group selected from the group consisting of an alkyl group of 1 to 14 carbons, a cycloalkyl group of 3 to 14 carbons, an aryl group of 6 to 14 carbons, an alkoxy group of 1 to 14 carbons, a cyano group, a nitro group, a heterocyclic group, a halogen atom, a carboxyl group, a hydroxyl group, an alkylsilyl group of 1 to 14 carbons, an alkyl ester group of 2 to 14 carbons and a derivative thereof, at least one of $R^4$ is a hydroxyl group or a carboxyl group, and p is an integer of 1 to 5.

A cyclic compound represented by the above formula (1) preferably includes the following compound.

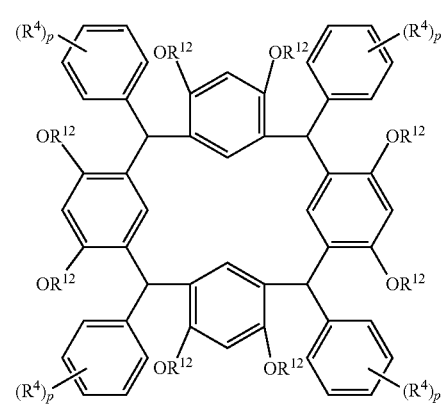

(2)

(In the above formula (2), $R^{12}$, $R^4$ and p are the same as above.)

A cyclic compound represented by the above formula (2) more preferably includes compounds represented by the following formulae (2-1) to (2-4).

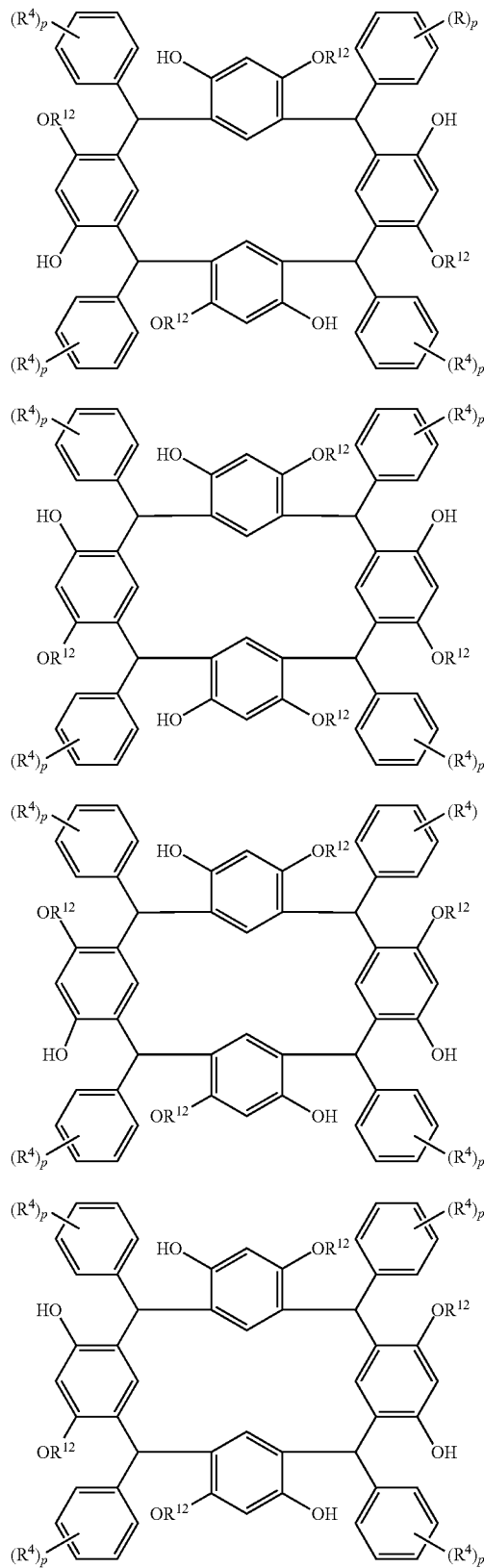

(In the formulae (2-1) to (2-4), $R^{12}$, $R^4$ and p are the same as above.)

The cyclic compound represented by the above formula (2) further preferably includes the following compound.

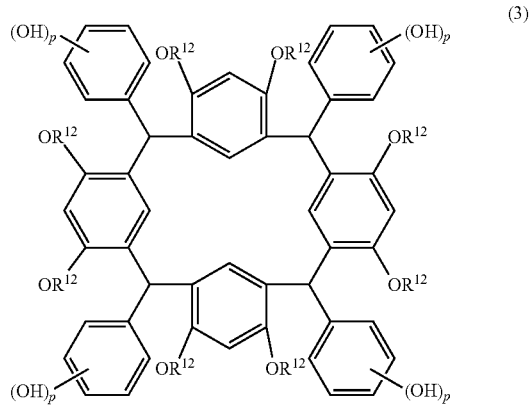

Cyclic compounds represented by the above formulae (2-1) to (2-4) further preferably include a compound represented by any of the isomers of the following formulae (3-1) to (3-4).

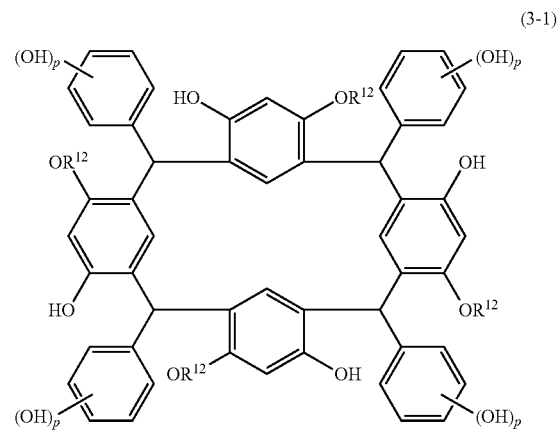

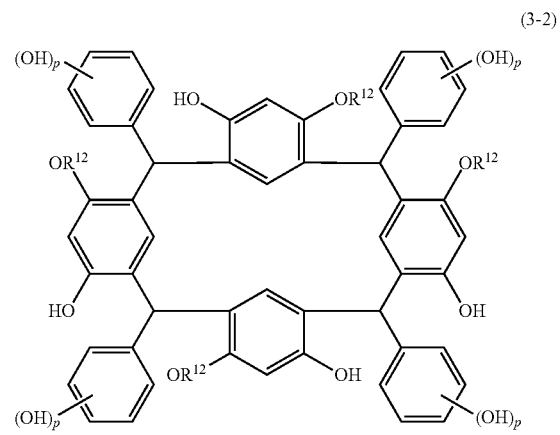

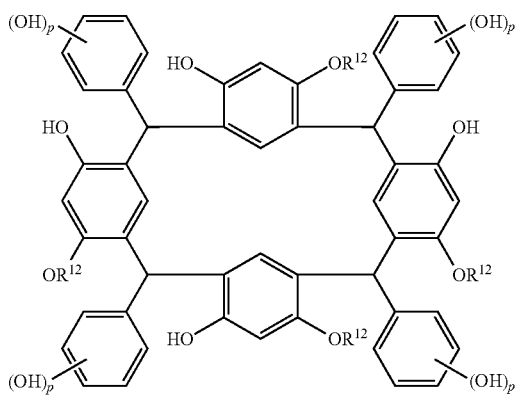
(3-3)

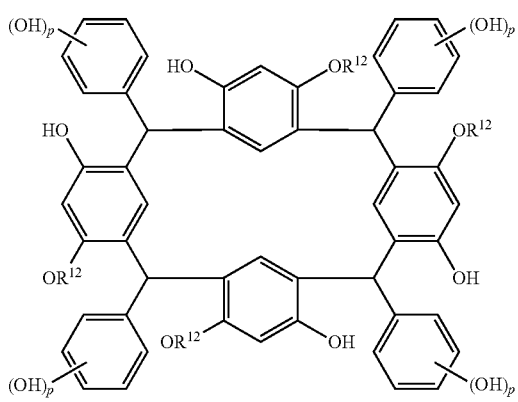
(3-4)

(In the formulae (3-1) to (3-4), $R^{12}$ and p are the same as above.)

The above cyclic compounds more preferably include a compound represented by any of the isomers of the following formulae (3'-1) to (3'-4).

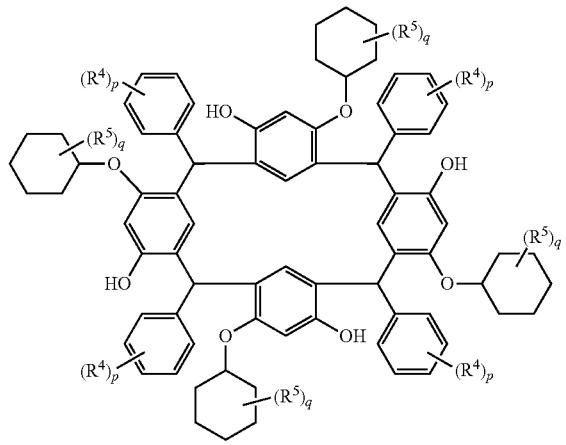
(3'-1)

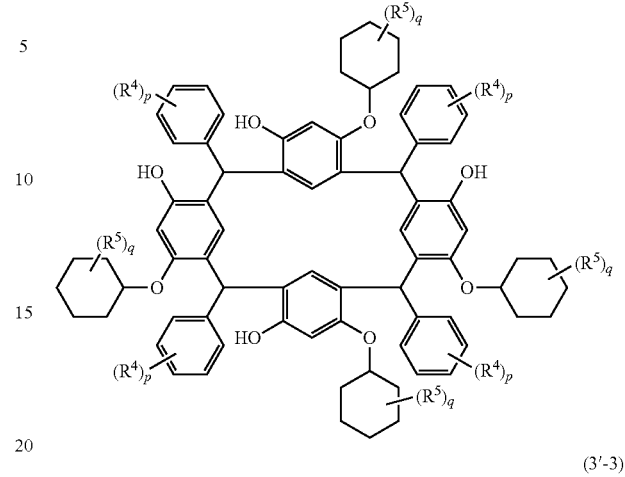
(3'-2)

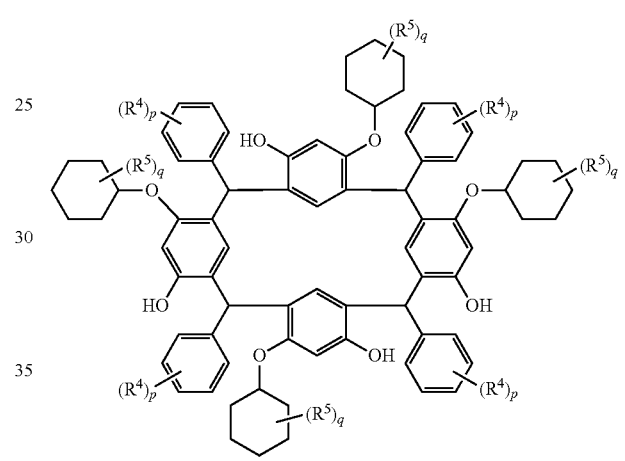
(3'-3)

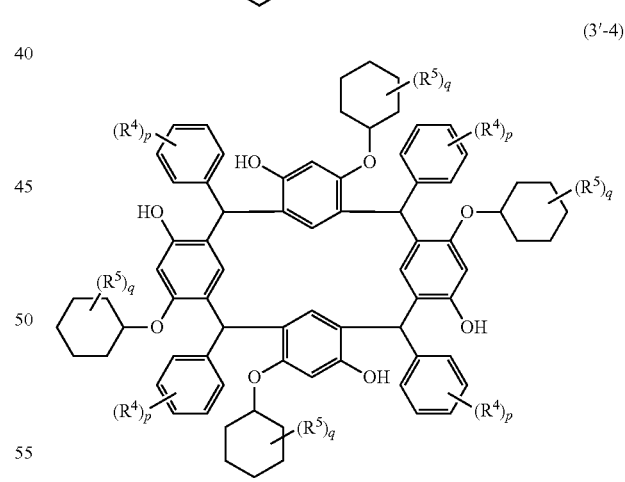
(3'-4)

In the formulae (3'-1) to (3'-4), $R^4$ and p are the same as above. $R^3$ is a functional group selected from the group consisting of an alkyl group of 1 to 3 carbons, a cycloalkyl group of 3 to 6 carbons, an aryl group of 6 to 14 carbons, an alkoxy group of 1 to 14 carbons, a cyano group, a nitro group, a heterocyclic group, a halogen atom, a carboxyl group, a hydroxyl group, an alkylsilyl group of 1 to 14 carbons and a derivative thereof, or a hydrogen group, and q is an integer of 0 to 2.

The cyclic compound of the invention, which has high heat resistance, is also excellent in film forming property due to its amorphousness, does not have sublimation property, is excellent in alkaline development, etching resistance and the like, has a phenolic hydroxyl group or a carboxyl group derived from aldehydes, does not have a phenolic hydroxyl group derived from resorcinol derivatives, without deteriorating the solubility in a safe solvent, improves the adhesiveness and the crosslinking reactivity of the resulting resist pattern, inhibits collapse and peeling of the resist pattern, and improves the sensitivity, is preferably used as a resist material, particularly a main component (base material) of a resist material.

Moreover, in the production aspect, since it can be produced at high yield by using various aldehydes such as industrially produced aromatic aldehyde and phenol derivatives such as methoxyphenol as raw materials, and conducting a dehydration condensation reaction with a nonmetal catalyst such as hydrochloric acid, it is also extremely excellent in practicality.

The cyclic compound of the invention can be obtained by using various aldehydes such as aromatic aldehyde and phenol derivatives such as cyclohexyloxyphenol as raw materials, and conducting a dehydration condensation reaction with a nonmetal catalyst such as hydrochloric acid. In this regard, since the objective substance can be obtained at high inversion rate without conducting any special purification process, by controlling the reaction rate at the reaction temperature of 0 to 60° C. to prevent resinification and gellation, it is also excellent in practicality.

The molecular weight of the cyclic compound represented by the above formula (1) is 800 to 5000, preferably 800 to 2000, and more preferably 1000 to 2000. Within the above range, the resolution improves while maintaining the film forming property required for a resist.

The cyclic compound in the invention can be in the cis form and the trans form, but may be any structure or mixture of them. When used as a resist component of a radiation-sensitive composition, it is preferable to have only one structure of either the cis form or the trans form, since it becomes a pure substance compound and the uniformity of the component within the resist film. A method for obtaining a cyclic compound having only one structure of either the cis form or the trans form can be conducted by publicly known methods such as separation by column chromatography or preparative liquid chromatography, and optimization of reaction solvent and reaction temperature upon production.

The cyclic compound represented by the above formula (1) can be obtained by a condensation reaction of one or more kinds selected from the group consisting of a compound (aldehydic compound (A1A)) having 2 to 59 carbons and 1 to 4 formyl groups, and one or more kinds selected from the group consisting of phenolic compound (A2).

More preferably, the cyclic compound represented by the above formula (1) can be obtained by a condensation reaction of one or more kinds selected from the group consisting of aromatic carbonyl compound (A1), and one or more kinds selected from the group consisting of phenolic compound (A2).

The aromatic carbonyl compound (A1) is hydroxybenzaldehyde of 7 to 20 carbons or carboxybenzaldehyde of 7 to 20 carbons, exemplified by hydroxybenzaldehyde, hydroxymethylbenzaldehyde, hydroxydimethylbenzaldehyde, hydroxyethylbenzaldehyde, hydroxypropylbenzaldehyde, hydroxybutylbenzaldehyde, hydroxyethylmethylbenzaldehyde, hydroxyisopropylmethylbenzaldehyde, hydroxydiethylbenzaldehyde, hydroxyanisaldehyde, hydroxynaphthoaldehyde, hydroxyanthrazaldehyde, hydroxycyclopropylbenzaldehyde, hydroxycyclobutylbenzaldehyde, hydroxycyclopentylbenzaldehyde, hydroxycyclohexylbenzaldehyde, hydroxyphenylbenzaldehyde, hydroxynaphthylbenzaldehyde, hydroxyadamantylbenzaldehyde, hydroxynorbornylbenzaldehyde, hydroxylactylbenzaldehyde, hydroxyisopropylbenzaldehyde, hydroxynormalpropylbenzaldehyde, hydroxybromobenzaldehyde, dimethylaminohydroxybenzaldehyde, dihydroxybenzaldehyde, trihydroxybenzaldehyde, carboxybenzaldehyde, dicarboxybenzaldehyde, formylmethylbenzoic acid, formylethylbenzoic acid, formyldimethylbenzoic acid, formyldiethylbenzoic acid, formylchlorobenzoic acid, formylbromobenzoic acid, formylhydroxybenzoic acid, formyldichlorobenzoic acid, formyldibromobenzoic acid, formyldihydroxybenzoic acid, and the like, preferably hydroxybenzaldehyde, dihydroxybenzaldehyde and trihydroxybenzaldehyde, and more preferably 2-hydroxybenzaldehyde, 3-hydroxybenzaldehyde, 4-hydroxybenzaldehyde, 2,4-dihydroxybenzaldehyde, 3,4-dihydroxybenzaldehyde and 3,5-dihydroxybenzaldehyde. The aromatic carbonyl compound (A1) may have a linear or branched alkyl group of 1 to 4 carbons, a cyano group, a hydroxyl group, a halogen and the like within the range of not deteriorating the effect of the invention. The aromatic carbonyl compound (A1) may be used alone or in combination of two or more kinds.

The phenolic compound (A2) is alkoxyphenol of 12 to 20 carbons, exemplified by cyclohexyloxyphenol, methylcyclohexyloxyphenol, dimethylcyclohexyloxyphenol, ethylcyclohexyloxyphenol, propylcyclohexyloxyphenol, trimethylcyclohexyloxyphenol, butylcyclohexyloxyphenol, pentylcyclohexyloxyphenol, hexylcyclohexyloxyphenol, bicyclohexyloxyphenol, menthyloxyphenol, bornyloxyphenol, phenoxyphenol, chlorocyclohexyloxyphenol, cyclohexyloxyhydroxytoluene, dicyclohexyloxyphenol, fluorocyclohexyloxyphenol, cyclohexyloxyhydroxybenzoic acid, dicyclohexyloxyhydroxybenzoic acid, tricyclohexyloxyhydroxybenzoic acid, cyclohexyloxydihydroxybenzoic acid, methyl cyclohexyloxyhydroxybenzoate, methyl cyclohexyloxydihydroxybenzoate, methyl chlorocyclohexyloxyhydroxybenzoate, ethyl chlorocyclohexyloxyhydroxybenzoate, acetylcyclohexyloxyhydroxybenzoic acid and the like, preferably cyclohexyloxyphenol, methylcyclohexyloxyphenol and cyclohexylcresol, and more preferably 3-cyclohexyloxyphenol. The phenolic compound (A2) may have a linear or branched alkyl group of 1 to 4 carbons, a cyano group, a hydroxyl group, a halogen atom and the like, within the range of not deteriorating the effect of the invention. The phenolic compound (A2) may be used alone or in combination of two or more kinds.

The cyclic compound represented by the above formula (1) can be produced by a publicly known method. For example, the cyclic compound (A) can be obtained by using 0.1 to 10 moles of the phenolic compound (A2) per mole of the aromatic carbonyl compound (A1), and an acid catalyst (such as hydrochloric acid, sulfuric acid, or para-toluene sulfonic acid) in an organic solvent such as methanol or ethanol, reacting at 60 to 150° C. for about 0.5 to 20 hours, filtering, washing with alcohols such as methanol, washing with water, filtering to separate, and drying. The cyclic compound (A) can also be obtained by using a basic catalyst (such as sodium hydroxide, barium hydroxide or 1,8-diazabicyclo[5.4.0]undecene-7) instead of the acid catalyst and reacting in the same way. Moreover, the cyclic compound (A) can also be produced by treating the above aromatic carbonyl compound (A1) with hydrogen halide or halogen gas into dihalide, and reacting the isolated dihalide with the phenolic compound (A2).

It is more preferable to use two or more kinds of aromatic carbonyl compound (A1) and two or more kinds of phenolic compound (A2). By using two or more kinds of aromatic carbonyl compound (A1) and two or more kinds of phenolic compound (A2), the solubility of the resulting cyclic compound in a semiconductor safe solvent improves.

In order to reduce the remaining metal amount, the cyclic compound may be purified if required. Also, since the storage stability of a radiation-sensitive composition generally decreases when an acid catalyst and a co-catalyst remain, or the sensitivity of a radiation-sensitive composition generally decreases when a basic catalyst remains, purification for the purpose of reducing them may be conducted. The purification can be conducted by any publicly known method unless a cyclic compound is modified, and the method is not particularly limited but exemplified by methods of washing with water, washing with an acid aqueous solution, washing with a basic aqueous solution, treating with ion exchange resin, treating by silica gel column chromatography, and the like. It is more preferable to conduct these purification methods in combination of two or more kinds. It is possible to arbitrarily select the optimal one for the acid aqueous solution, the basic aqueous solution, the ion exchange resin and the silica gel column chromatography, according to the amount and the kind of metal, acidic compound and/or basic compound to be removed, the kind of cyclic compound to be purified and the like. For example, the acid aqueous solution includes aqueous solutions of hydrochloric acid, nitric acid and acetic acid with a concentration of 0.01 to 10 mol/L, the basic aqueous solution includes an aqueous solution of ammonia with a concentration of 0.01 to 10 mol/L, and the ion exchange resin includes cation exchange resin, such as Amberlyst 15J-HG Dry made by Organo. Drying may be conducted after purification. Drying can be conducted by a publicly known method, and the method is not particularly limited, but includes methods of vacuum drying, hot air drying and the like under the condition where a cyclic compound is not modified.

The cyclic compound represented by the above formula (1) can form an amorphous film by spin coating. Also, it can be applied to a typical semiconductor production process.

The cyclic compound of the invention represented by the above formula (1) is useful as a negative type resist material which becomes a hardly soluble compound in an alkaline developing solution by being irradiated with KrF excimer laser, extreme ultraviolet, electron beam or X-ray. It is assumed that by irradiating the cyclic compounds with KrF excimer laser, extreme ultraviolet, electron beam or X-ray, a condensation reaction among the compounds is induced to provide a compound hardly soluble in an alkaline developing solution. A resist pattern thus obtained has very small LER.

The cyclic compound of the invention can be formulated into a negative type radiation-sensitive composition as a main component itself, and moreover can be added to a radiation-sensitive composition not as a main component but as an additive agent for improving sensitivity and etching resistance. In this case, the cyclic compound is used in 1 to 49.999% by weight of the total weight of solid component.

The dissolution rate of the amorphous film of the cyclic compound of the invention in 2.38% by mass tetramethylammonium hydroxide (TMAH) aqueous solution at 23° C. is preferably not less than 10 Å/sec, more preferably 10 to 10000 Å/sec, and further preferably 100 to 1000 Å/sec. With not less than 10 Å/sec, it dissolves in an alkaline developing solution to be a resist. Also, when it has the dissolution rate of not more than 10000 Å/sec, the resolution may improve. It is presumed that this is because due to the change in the solubility before and after exposure of the cyclic compound, contrast at the interface between the unexposed portion being dissolved in an alkaline developing solution and the exposed portion not being dissolved in an alkaline developing solution becomes large. Moreover, there are reduction effects of LER and defect.

The glass transition temperature of the cyclic compound of the invention is preferably not less than 100° C., more preferably not less than 120° C., further preferably not less than 140° C., and particularly preferably not less than 150° C. By having the glass transition temperature within the above range, in semiconductor lithography process, it can have heat resistance capable of maintaining the resist pattern shape and performance such as high resolution can be impart.

The crystallization heat generation amount obtained by differential scanning calorimetrical analysis of the glass transition temperature of the cyclic compound of the invention preferably is less than 20 J/g. Also, (crystallization temperature)–(glass transition temperature) is preferably not less than 70° C., more preferably not less than 80° C., further preferably not less than 100° C., and particularly preferably not less than 130° C. When the crystallization heat generation amount is less than 20 J/g or (crystallization temperature)–(glass transition temperature) is within the above range, by spin coating a radiation-sensitive composition, an amorphous film is easy to be formed, the film forming property required for a resist can be maintained over an extended period of time, and the resolution can be improved.

In the invention, the crystallization heat generation amount, crystallization temperature and glass transition temperature can be measured as below using DSC/TA-SOWS made by Shimadzu and obtained by differential scanning calorimetrical analysis. About 10 mg of the sample is placed in a non-sealed container made of aluminum, and the temperature is raised to the melting point or above at the rate of temperature rise of 20° C./min in a nitrogen gas stream (50 ml/min). After quenching, again the temperature is raised to the melting point or above at the rate of temperature rise of 20° C./min in a nitrogen gas stream (30 ml/min). After further quenching, again the temperature is raised to 400° C. at the rate of temperature rise of 20° C./min in a nitrogen gas stream (30 ml/min). The temperature at the middle point of the region where the discontinuous portion appears in the baseline (where the specific heat is changed into the half) is the glass transition temperature (Tg), and the temperature at the subsequently appearing heat generation peak is the crystallization temperature. The heat generation amount is obtained from the area of the region surrounded by the heat generation peak and the baseline, as the crystallization heat generation amount.

The cyclic compound of the invention preferably has low sublimation property under normal pressure at not more than 100° C., preferably not more than 120° C., more preferably not more than 130° C., further preferably not more than 140° C. and particularly preferably not more than 150° C. By low sublimation property, in thermogravimetrical analysis, the weight decrease after being kept at a predetermined temperature for 10 minutes is not more than 10%, preferably not more than 5%, more preferably not more than 3%, further preferably not more than 1%, and particularly preferably not more than 0.1%. By having low sublimation property, contamination of an exposure equipment by outgas upon exposure can be prevented. Also, a good resist pattern shape with low LER can be provided.

The cyclic compound of the invention meets preferably F<3.0 (F represents total atom number/(total carbon atom number-total oxygen atom number)), more preferably F<2.5. By meeting the above condition, it becomes excellent in dry etching resistance.

The cyclic compound of the invention dissolves in a solvent selected from propylene glycol monomethyl ether acetate (PGMEA), propylene glycol monomethyl ether (PGME), cyclohexanone (CHN), cyclopentanone (CPN), 2-heptanone, anisole, butyl acetate, ethyl propionate, and ethyl lactate, and showing the highest dissolving ability to the cyclic compound, in preferably not less than 1% by weight, more preferably not less than 5% by weight, and further preferably not less than 10% by weight at 23° C., particularly preferably in a solvent selected from PGMEA, PGME and CHN, and showing the highest dissolving ability to the cyclic compound, in not less than 20% by weight at 23° C., and particularly preferably in PGMEA in not less than 20% by weight at 23° C. By meeting the above conditions, the use in semiconductor production process in the actual production becomes possible.

A halogen atom may be introduced into the cyclic compound of the invention within the range of not deteriorating the effect of the invention. The percentage of the number of halogen atoms to the number of aal constituent atoms of the cyclic compound is preferably 0.1 to 60%, more preferably 0.1 to 40%, further preferably 0.1 to 20%, particularly preferably 0.1 to 10%, and most preferably 1 to 5%. Within the above range, the film forming property can be maintained while increasing the sensitivity to radiation. Also the solubility in a safe solvent can be improved.

A nitrogen atom may be introduced into the cyclic compound of the invention, within the range of not deteriorating the effect of the invention. The percentage of the number of nitrogen atoms to the number of all constituent atoms of the cyclic compound is preferably 0.1 to 40%, more preferably 0.1 to 20%, further preferably 0.1 to 10%, and particularly preferably 0.1 to 5%. Within the above range, the line edge roughness of the resulting resist pattern can be reduced. Also as a nitrogen atom, a nitrogen atom contained in secondary amine or tertiary amine is preferable, and a nitrogen atom contained in tertiary amine is more preferable.

A crosslinking reactive group initiating a crosslinking reaction by visible light, ultraviolet, excimer laser, electron beam, extreme ultraviolet (EUV), X-ray, and ion beam irradiation or a chemical reaction induced thereby may be introduced into the cyclic compound of the invention, within the range of not deteriorating the effect of the invention. The introduction is conducted by, for example, reacting the cyclic compound with a crosslinking reactive group introducing agent in the presence of a basic catalyst. The crosslinking reactive group includes a carbon-carbon multiple bond, an epoxy group, an azide group, a halogenated phenyl group, and a chloromethyl group. The crosslinking reactive group introducing agent includes an acid having such a crosslinking reactive group, acid chloride, acid anhydride, a carboxylic acid derivative such as dicarbonate, alkyl halide and the like. A radiation-sensitive composition containing a cyclic compound having a crosslinking reactive group is also useful as a nonpolymer based radiation-sensitive composition with high solution, high heat resistance and solvent solubility.

A nonacid dissociation functional group may be introduced into at least one phenolic hydroxyl group of the cyclic compound of the invention, within the range of not deteriorating the effect of the invention. The nonacid dissociation functional group refers to a characteristic group not cleaving in the presence of acid or generating an alkali soluble group. For example, it includes a functional group selected from the group consisting of an alkyl group of C1 to 20, a cycloalkyl group of C3 to 20, an aryl group of C6 to 20, an alkoxyl group of C1 to 20, a cyano group, a nitro group, a hydroxyl group, a heterocyclic group, a halogen atom, a carboxyl group, an alkylsilyl group of C1 to 20 and a derivative thereof, which are not degraded by action of acid.

A naphthoquinone diazide ester group may be introduced into at least one phenolic hydroxyl group of the cyclic compound of the invention within the range of not deteriorating the effect of the invention. A compound having a naphthoquinone diazide ester group introduced into at least one phenolic hydroxyl group of the cyclic compound can be formulated into a negative type radiation-sensitive composition as a main component itself, and moreover added to a radiation-sensitive composition as a positive type radiation-sensitive composition, an acid generating agent and an additive agent having itself as a main component.

An acid generating functional group generating an acid by irradiation of radiation may be introduced into at least one phenolic hydroxyl group of the cyclic compound of the invention, within the range of not deteriorating the effect of the invention. A cyclic polyphenol compound having an acid generating functional group generating an acid by irradiation of radiation introduced into at least one phenolic hydroxyl group of the cyclic compound can be formulated into a negative type radiation-sensitive composition as a main component itself, and moreover added to a radiation-sensitive composition as a positive type radiation-sensitive composition, an acid generating agent and an additive agent having itself as a main component.

[Radiation-Sensitive Composition]

The invention relates to a radiation-sensitive composition containing a cyclic compound represented by the above formula (1) and a solvent. Also, the invention is preferably a radiation-sensitive composition comprising 1 to 80% by weight of solid component and 20 to 99% by weight of solvent, and moreover, the cyclic compound is preferably 50 to 99.999% by weight of the total weight of solid component.

The radiation-sensitive composition of the invention can form an amorphous film by spin coating. The dissolution rate of the amorphous film formed by spin coating the cyclic compound of the invention in 2.38% by mass TMAH aqueous solution at 23° C. is preferably not less than 10 Å/sec, more preferably 10 to 10000 Å/sec, and further preferably 100 to 1000 Å/sec. When the dissolution rate is not less than 10 Å/sec, it dissolves in an alkaline developing solution to be a resist. Also, when the amorphous film has the dissolution rate of not more than 10000 Å/sec, the resolution may improve. It is presumed that this is because due to the change in the solubility before and after exposure of the cyclic compound, contrast at the interface between the unexposed portion being dissolved in an alkaline developing solution and the exposed portion not being dissolved in an alkaline developing solution becomes large. Moreover, there are reduction effects of LER and defect.

The dissolution rate of the portion exposed by radiation such as KrF excimer laser, extreme ultraviolet, electron beam or X-ray of the amorphous film formed by spin coating the radiation-sensitive composition of the invention in 2.38% by mass TMAH aqueous solution at 23° C. is preferably not more than 5 Å/sec, more preferably 0.05 to 5 Å/sec, and further preferably 0.0005 to 5 Å/sec. When the dissolution rate is not more than 5 Å/sec, it is insoluble in an alkaline developing solution and can be a resist. Also, when the exposed portion has the dissolution rate of not less than 0.0005 Å/sec, the solution may improve. It is presumed that this is because the micro surface portion of the cyclic compound dissolves and LER is reduced. Moreover, there is a reduction effect of defect.

The radiation-sensitive composition of the invention contains preferably 1 to 80% by weight of solid component and 20 to 99% by weight of solvent, more preferably 1 to 50% by weight of solid component and 50 to 99% by weight of solvent, further preferably 2 to 40% by weight of solid component and 60 to 98% by weight of solvent, and particularly preferably 2 to 10% by weight of solid component and 90 to 98% by weight of solvent.

The amount of the cyclic compound represented by the formula (1) is 50 to 99.999% by weight, preferably 65 to 80% by weight, and more preferably 60 to 70% by weight of the total weight of solid component. With the above compounding percentage, high solution can be obtained and line edge roughness becomes small.

The radiation-sensitive composition of the invention is preferable to contain one or more kinds of acid generating agent (C) generating an acid directly or indirectly by irradiation of any radiation selected from visible light, ultraviolet, excimer laser, electron beam, extreme ultraviolet (EUV), X-ray, and ion beam. The amount of the acid generating agent used is preferably 0.001 to 50% by weight of the total weight of solid component (summation of optionally used solid component such as cyclic component, acid generating agent (C), acid crosslinking agent (G), acid diffusion controlling agent (E) and other component (F), hereinafter the same), more preferably 1 to 40% by weight, further preferably 3 to 30% by weight, and particularly preferably 10 to 25% by weight. By using it within the above range, a resist pattern profile with high sensitivity and low edge roughness can be obtained. In the invention, the acid generation method is not limited as long as an acid is generated within a system. By using excimer laser instead of ultraviolet such as g-ray and i-ray, finer processing is possible, and also by using electron beam, extreme ultraviolet, X-ray or ion beam as a high energy ray, further finer processing is possible.

The above acid generating agent (C) is preferably at least one kind selected from the group consisting of compounds represented by the following formulae (4-1) to (4-8).

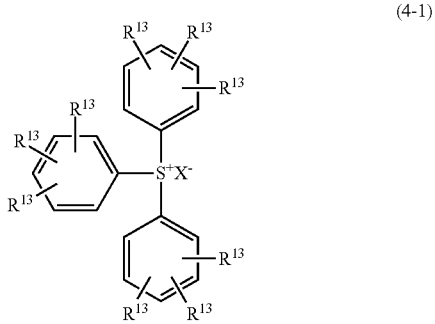

(4-1)

In the formula (4-1), $R^{13}$ may be the same or different, and are each independently a hydrogen atom, a linear, branched or cyclic alkyl group, a linear, branched or cyclic alkoxy group, a hydroxyl group or a halogen atom; $X^-$ is an alkyl group, an aryl group, a sulfonic acid ion having a halogen substituted alkyl group or a halogen substituted aryl group, or a halide ion.

The compound represented by the above formula (4-1) is preferably at least one kind selected from the group consisting of triphenylsulfonium trifluoromethanesulfonate, triphenylsulfonium nonafluoro-n-butanesulfonate, diphenyltolylsulfonium nonafluoro-n-butanesulfonate, triphenylsulfonium perfluoro-n-octanesulfonate, dipheny-4-methylphenylsulfonium trifluoromethanesulfonate, di-2,4,6-trimethyl-phenylsulfonium trifluoromethanesulfonate, diphenyl-4-t-butoxyphenylsulfonium trifluoromethanesulfonate, diphenyl-4-t-butoxyphenylsulfonium nonafluoro-n-butanesulfonate, diphenyl-4-hydroxyphenylsulfonium trifluoromethanesulfonate, bis(4-fluorophenyl)-4-hydroxyphenylsulfonium trifluoromethanesulfonate, diphenyl-4-hydroxyphenylsulfonium nonafluoro-n-butanesulfonate, bis(4-hydroxyphenyl)-phenylsulfonium trifluoromethanesulfonate, tri(4-methoxyphenyl)sulfonium trifluoromethanesulfonate, tri(4-fluorophenyl)sulfonium trifluoromethanesulfonate, triphenylsulfonium 1-butanesulfonate, triphenylsulfonium p-toluenesulfonate, triphenylsulfonium benzenesulfonate, diphenyl-2,4,6-trimethylphenyl-p-toluenesulfonate, diphenyl-2,4,6-trimethylphenylsulfonium-2-trifluoromethylbenzenesulfonate, diphenyl-2,4,6-trimethylphenylsulfonium-4-trifluoromethylbenzenesulfonate, diphenyl-2,4,6-trimethylphenylsulfonium-2,4-difluorobenzenesulfonate, diphenyl-2,4,6-trimethylphenylsulfonium hexafluorobenzenesulfonate, diphenylnaphthylsulfonium trifluoromethanesulfonate, diphenyl-4-hydroxyphenylsulfonium-p-toluenesulfonate, triphenylsulfonium 10-camphersulfonate, diphenyl-4-hydroxyphenylsulfonium10-camphersulfonate and cyclo(1,3-perfluoropropanedisulfone)imidate.

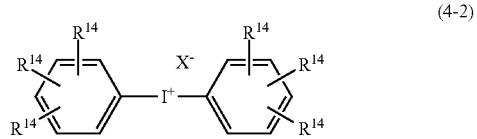

(4-2)

In the formula (4-2), $R^{14}$ may be the same or different, and each independently represents a hydrogen atom, a linear, branched or cyclic alkyl group, a linear, branched or cyclic alkoxy group, a hydroxyl group or a halogen atom. $X^-$ is the same as above.

The compound represented by the above formula (4-2) is preferably at least one kind selected from the group consisting of bis(4-t-butylphenyl)iodonium trifluoromethanesulfonate, bis(4-t-butylphenyl)iodonium nonafluoro-n-butanesulfonate, bis(4-t-butylphenyl)iodonium perfluoro-n-octanesulfonate, bis(4-t-butylphenyl)iodonium p-toluenesulfonate, bis(4-t-butylphenyl)iodonium benzenesulfonate, bis(4-t-butylphenyl)iodonium-2-trifluoromethylbenzenesulfonate, bis(4-t-butyl-phenyl)iodonium-4-trifluoromethylbenzenesulfonate, bis(4-t-butylphenyl)iodonium-2,4-difluorobenzenesulfonate, bis(4-t-butyl-phenyl)iodonium hexafluorobenzenesulfonate, bis(4-t-butylphenyl)iodonium 10-camphersulfonate, diphenyliodonium trifluoromethanesulfonate, diphenyliodonium nonafluoro-n-butanesulfonate, diphenyliodonium perfluoro-n-octanesulfonate, diphenyliodonium p-toluenesulfonate, diphenyliodonium benzenesulfonate, diphenyliodonium 10-camphersulfonate, diphenyliodonium-2-trifluoromethylbenzenesulfonate, diphenyliodonium-4-trifluoromethybenzenesulfonate, diphenyliodonium-2,4-difluorobenzenesulfonate, diphenyliodonium hexafluorobenzenesulfonate, di(4-trifluoromethylphenyl)iodonium trifluoromethanesulfonate, di(4-trifluoromethylphenyl)iodonium nonafluoro-n-butanesulfonate, di(4-trifluoromethylphenyl)iodonium perfluoro-n-octaneulfonate, di(4-trifluoromethylphenyl)iodonium p-toluenesulfonate, di(4-trifluoromethylphenyl)iodonium benzenesulfonate and di(4-trifluoromethylphenyl)iodonium 10-camphersulfonate.

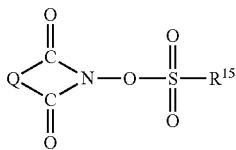

(4-3)

In the formula (4-3), Q is an alkylene group, an arylene group or an alkoxylene group, and $R^{15}$ is an alkyl group, an aryl group, a halogen substituted alkyl group or a halogen substituted aryl group.

The compound represented by the above formula (4-3) is preferably at least one kind selected from the group consisting of N-(trifluoromethylsulfonyloxy)succinimide, N-(trifluoromethylsulfonyloxy)phthalimide, N-(trifluoromethylsulfonyloxy)diphenylmaleimide, N-(trifluoromethylsulfonyloxy)bicyclo[2.2.1]hepto-5-ene-2,3-dicarboxylmide, N-(trifluoromethylsulfonyloxy)naphthylimide, N-(10-camphersulfonyloxy)succinimide, N-(10-camphersulfonyloxy)phthalimide, N-(10-camphersulfonyloxy)diphenylmaleimide, N-(10-camphersulfonyloxy)bicyclo[2.2.1]hepto-5-ene-2,3-dicarboxylmide, N-(10-camphersulfonyloxy)naphthylimide, N-(n-octanesulfonyloxy)bicyclo[2.2.1]hepto-5-ene-2,3-dicarboxylmide, N-(n-octanesulfonyloxy)naphthylimide, N-(p-toluenesulfonyloxy)bicyclo[2.2.1]hepto-5-ene-2,3-dicarboxyimide, N-(p-toluenesulfonyloxy)naphthylimide, N-(2-trifluoromethylbenzenesulfonyloxy)bicyclo[2.2.1]hepto-5-ene-2,3-dicarboxylmide, N-(2-trifluoromethylbenzenesulfonyloxy)naphthylimide, N-(4-trifluoromethylbenzenesulfonyloxy)bicyclo[2.2.1]hepto-5-ene-2,3-dicarboxylmide, N-(4-trifluorobenzenesulfonyloxy)naphthylimide, N-(perfluorobenzenesulfonyloxy)bicyclo[2.2.1]hepto-5-ene-2,3-dicarboxyimide, N-(perfluorobenzenesulfonyloxy)naphthylimide, N-(1-naphthalenesulfonyloxy)bicyclo[2.2.1]hepto-5-ene-2,3-dicarboxyimide, N-(1-naphthalenesulfonyloxy)naphthylimide, N-(nonafluoro-n-butanesulfonyloxy)bicyclo[2.2.1]hepto-5-ene-2,3-dicarboxylmide, N-(nonafluoro-n-butanesulfonyloxy)naphthylimide, N-(perfluoro-n-octanesulfonyloxy)bicyclo[2.2.1]hepto-5-ene-2,3-dicarboxylmide and N-(perfluoro-n-octanesulfonyloxy)naphthylimide.

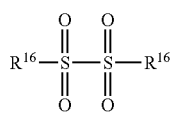

(4-4)

In the formula (4-4), $R^{16}$ may be the same or different, and are each independently an optionally substituted linear, branched or cyclic alkyl group, an optionally substituted aryl group, an optionally substituted heteroaryl group or an optionally substituted aralkyl group.

The compound represented by the above formula (4-4) is preferably at least one kind selected from the group consisting of diphenyldisulfone, di(4-methylphenyl)disulfone, dinaphthyldisulfone, di(4-tert-butylphenyl)disulfone, di(4-hydroxyphenyl)disulfone, di(3-hydroxynaphthyl)disulfone, di(4-fluorophenyl)disulfone, di(2-fluorophenyl)disulfone and di(4-trifluoromethylphenyl)disulfone.

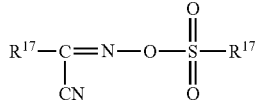

(4-5)

In the formula (4-5), $R^{17}$ may be the same or different, and are each independently an optionally substituted linear, branched or cyclic alkyl group, an optionally substituted aryl group, an optionally substituted heteroaryl group or an optionally substituted aralkyl group.

The compound represented by the above formula (4-5) is preferably at least one kind selected from the group consisting of α-(methylsulfonyloxyimino)-phenylacetonitrile, α-(methylsulfonyloxyimino)-4-methoxyphenylacetonitrile, α-(trifluoromethylsulfonyloxyimino)-phenylacetonitrile, α-(trifluoromethylsulfonyloxyimino)-4-methoxyphenylacetonitrile, α-(ethylsulfonyloxyimino)-4-methoxyphenylacetonitrile, α-(propylsulfonyloxyimino)-4-methyl-phenylacetonitrile and α-(methylsulfonyloxyimino)-4-bromophenylacetonitrile.

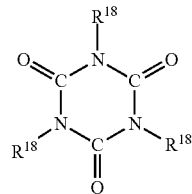

(4-6)

In the formula (4-6), $R^{18}$ may be the same or different, and are each independently a halogenated alkyl group having one or more chlorine atoms and one or more bromine atoms. The number of carbon atoms of the halogenated alkyl group is preferably 1 to 5.

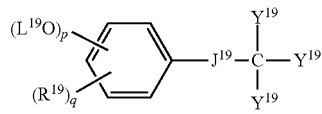

(4-7)

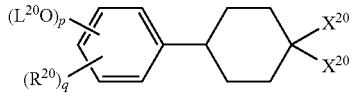

(4-8)

In the formulae (4-7) to (4-8), $R^{19}$ and $R^{20}$ are each independently an alkyl group of 1 to 3 carbon atoms such as a methyl group, an ethyl group, an n-propyl group and an isopropyl group, a cycloalkyl group such as a cyclopentyl group and a cyclohexyl group, an alkoxyl group of 1 to 3 carbon atoms such as a methoxy group, an ethoxy group and a propoxy group, or an aryl group such as a phenyl group, a toluoyl group and a naphthyl group, preferably an aryl group of 6 to 10 carbon atoms. $L^{19}$ and $L^{20}$ are each independently an organic group having a 1,2-naphthoquinoneazide group. The organic group having a 1,2-naphthoquinoneazide group can particularly preferably include a 1,2-quinonediazidesulfonyl group such as a 1,2-naphthoquinonediazide-4-sulfonyl group, a 1,2-naphthoquinonediazide-5-sulfonyl group and a 1,2-naphthoquinonediazide-6-sulfonyl group. Particularly, a 1,2-naphthoquinonediazide-4-sulfonyl group and a 1,2-naphthoquinonediazide-5-sulfonyl group are preferable. p is an integer of 1 to 3, q is an integer of 0 to 4, and 1≤p+q≤5. $J^{19}$ is a single bond, a polymethylene group of 1 to 4 carbon atoms, a cycloalkylene group, a phenylene group, a group represented by the following formula (4-7-1), a carbonyl group, an ester group, an amide group or an ether group, $Y^{19}$ is a hydrogen atom, an alkyl group or an aryl group, and $X^{20}$ are each independently a group represented by the following formula (4-8-1).

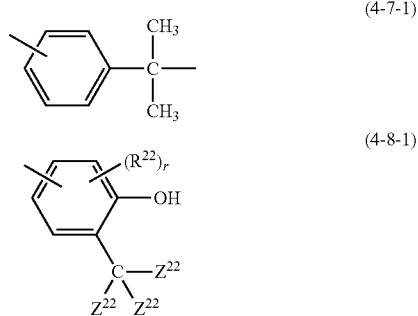

(4-7-1)

(4-8-1)

In the formula (4-8-1), $Z^{22}$ are each independently an alkyl group, a cycloalkyl group or an aryl group, $R^{22}$ is an alkyl group, a cycloalkyl group or an alkoxyl group, and r is an integer of 0 to 3.

The other acid generating agent includes bissulfonyldiazomethanes such as bis(p-toluenesulfonyl)diazomethane, bis(2,4-dimethylphenylsulfonyl)diazomethane, bis(tert-butylsulfonyl)diazomethane, bis(n-butylsulfonyl)diazomethane, bis(isobutylsulfonyl)diazomethane, bis(isopropylsulfonyl)diazomethane, bis(n-propylsulfonyl)diazomethane, bis(cyclohexylsulfonyl)diazomethane, bis(isopropylsulfonyl)diazomethane, 1,3-bis(cyclohexylsulfonylazomethylsulfonyl)propane, 1,4-bis(phenylsulfonylazomethylsulfonyl)butane, 1,6-bis(phenylsulfonylazomethylsulfonyl)hexane and 1,10-bis(cyclohexylsulfonylazomethylsulfonyl)decane, halogen-containing triazine derivatives such as 2-(4-methoxyphenyl)-4,6-(bistrichloromethyl)-1,3,5-triazine, 2-(4-methoxynaphthyl)-4,6-(bistrichloromethyl)-1,3,5-triazine, tris(2,3-dibromopropyl)-1,3,5-triazine and tris(2,3-dibromopropyl)isocyanurate, and the like.

Among the above acid generating agents, an acid generating agent having an aromatic ring is preferable, and an acid generating agent represented by the formula (4-1) or (4-2) is more preferable. An acid generating agent having a sulfonate ion wherein X⁻ of the formula (4-1) or (4-2) has an aryl group or a halogen-substituted aryl group is further preferable, an acid generating agent having a sulfonate ion having an aryl group is particularly preferable, and diphenyltrimethylphenylsulfonium p-toluenesulfonate, triphenylsulfonium p-toluenesulfonate, triphenylsulfonium trifluoromethanesulfonate and triphenylsulfonium nonafluoromethanesulfonate are particularly preferable. By using the acid generating agent, LER can be reduced.

The above acid generating agent (C) can be used alone or in combination of two or more kinds.

The radiation-sensitive composition of the invention is preferable to contain one or more kinds of acid crosslinking agent (G). The acid crosslinking agent (G) is a compound capable of intramolecular or intermolecular crosslinking cyclic compound (A). Such acid crosslinking agent (G) can be exemplified by a compound having one or more kinds of substituent group having crosslinking reactivity (hereinafter, referred to as "crosslinkable substituent group") with the cyclic compound (A).

Particular examples of such a crosslinkable substituent group can include (i) a hydroxyalkyl group such as a hydroxy (C1-C6 alkyl group), a C1-C6 alkoxy (C1-C6 alkyl group) and an acetoxy (C1-C6 alkyl group) or a substituent group derived therefrom; (ii) a carbonyl group such as a formyl group and a carboxy (C1-C6 alkyl group) or a substituent group derived therefrom; (iii) a nitrogenous group-containing substituent group such as a dimethylaminomethyl group, a diethylaminomethyl group, a dimethylolaminomethyl group, a diethylolaminomethyl group and a morpholinomethyl group; (iv) a glycidyl group-containing substituent group such as a glycidyl ether group, a glycidyl ester group and a glycidylamino group; (v) a substituent group derived from an aromatic group such as a C6-C12 alkyloxy (C1-C6 alkyl group) and a C7-C12 aralkyloxy (C1-C6 alkyl group) such as a benzyloxymethyl group and a benzoyloxymethyl group; (vi) a polymerizable multiple bond-containing substituent group such as a vinyl group and a isopropenyl group, and the like for example. As the crosslinkable substituent group of the acid crosslinking agent (G) of the invention, a hydroxyalkyl group, an alkoxyalkyl group and the like are preferable, and particularly an alkoxymethyl group is preferable.

The acid crosslinking agent (G) having the above crosslinkable substituent group can be exemplified by (i) a methylol group-containing compound such as a methylol group-containing melamine compound, a methylol group-containing benzoguanamine compound, a methylol group-containing urea compound, a methylol group-containing glycoluryl compound and a methylol group-containing phenol compound; (ii) an alkoxyalkyl group-containing compound such as alkoxyalkyl group-containing melamine compound, an alkoxyalkyl group-containing benzoguanamine compound, an alkoxyalkyl group-containing urea compound, an alkoxyalkyl group-containing glycoluryl compound and an alkoxyalkyl group-containing phenol compound; (iii) a carboxymethyl group-containing compound such as a carboxymethyl group-containing melamine compound, a carboxymethyl group-containing benzoguanamine compound, a carboxymethyl group-containing urea compound, a carboxymethyl group-containing glycoluryl compound and a carboxymethyl group-containing phenol compound; (iv) an epoxy compound such as a bisphenol A based epoxy compound, a bisphenol F based epoxy compound, a bisphenol S based epoxy compound, a novolac resin based epoxy compound, a resol resin based epoxy compound and a poly(hydroxystyrene) based epoxy compound, and the like.

As the acid crosslinking agent (G), a compound having a phenolic hydroxyl group, and a compound and resin where the above crosslinkable substituent group is introduced into an acid functional group in alkali soluble resin to impart crosslinkability can be further used. The introduction rate of the crosslinkable substitute group in that case is adjusted to be normally 5 to 100 mol %, preferably 10 to 60 mol %, and more preferably 15 to 40 mol % based on the total acid functional groups in the compound having a phenolic hydroxyl group, and the alkali soluble resin. Within the above range, the crosslinking reaction sufficiently occurs, and a decrease in the film remaining rate, swelling phenomena, meandering and the like of a resist pattern can be avoided, which is preferable.

In the radiation-sensitive composition of the invention, as the acid crosslinking agent (G), an alkoxyalkylated urea compound or resin thereof, or an alkoxyalkylated glycoluryl compound or resin thereof is preferable. The particularly preferable acid crosslinking agent (G) can include compounds represented by the following formulae (5) and an alkoxymethylated melamine compound (acid crosslinking agent (G1)).

(5)

(5-1)

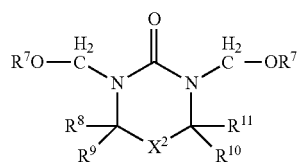

(5-2)

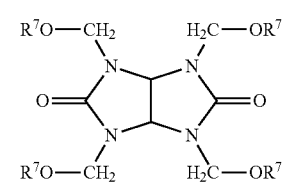

(5-3)

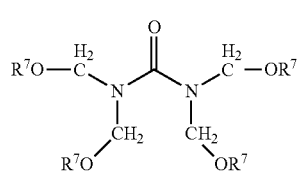

In the above formula (5), $R^7$ each independently represents an hydrogen atom, an alkyl group or an alkylsilyl group; $R^8$ to $R^{11}$ each independently represents an hydrogen atom, a hydroxyl group, an alkyl group or an alkoxyl group; and $X^2$ represents a single bond, a methylene group or an oxygen atom.

As $R^7$ in the above formulae (5), a hydrogen atom, an alkyl group of 1 to 6 carbons, or an acyl group of 2 to 6 carbons is preferable. The alkyl group of 1 to 6 carbons is further preferably an alkyl group of 1 to 3 carbons, and exemplified by a methyl group, an ethyl group and a propyl group. The acyl group of 2 to 6 carbons is further preferably an acyl group of 2 to 4 carbons, and exemplified by an acetyl group and a propyonyl group. $R^8$ to $R^{11}$ in the formulae (5) is preferably a hydrogen atom, a hydroxyl group, an alkyl group of 1 to 6 carbons, or an alkoxyl group of 1 to 6 carbons. The alkyl group of 1 to 6 carbons is further preferably an alkyl group of 1 to 3 carbons, and exemplified by a methyl group, an ethyl group and a propyl group. The alkoxyl group of 1 to 6 carbons is further preferably an alkoxyl group of 1 to 3 carbons, and exemplified by a methoxy group, an ethoxy group and a propoxy group. $X^2$ represents a single bond, a methylene group or an oxygen atom, and a single bond or a methylene group is preferable. In addition, $R^7$ to $R^{11}$ and $X^2$ may further have a substituent group including an alkyl group such as a methyl group and an ethyl group, an alkoxy group such as a methoxy group and an ethoxy group, a hydroxyl group and a halogen atom in the group exemplified above. A plurality of $R^7$ and $R^8$ to $R^{11}$ may be each the same or different.

The compound represented by the formula (5-1) can particularly be exemplified by compounds shown below.

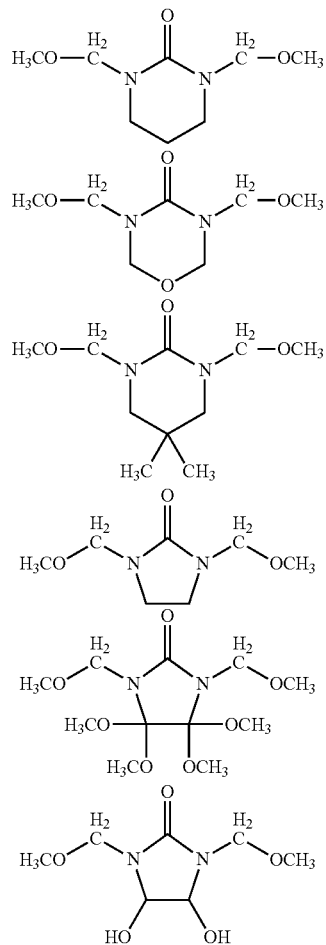

The compound represented by the formula (5-2) can particularly be exemplified by N,N,N,N-tetra(methoxymethyl)glycoluryl, N,N,N,N-tetra(ethoxymethyl)glycoluryl, N,N,N,N-tetra(n-propoxymethyl)glycoluryl, N,N,N,N-tetra(isopropoxymethyl)glycoluryl, N,N,N,N-tetra(n-butoxymethyl)glycoluryl, N,N,N,N-tetra(t-butoxymethyl)glycoluryl, and the like. Among them, particularly N,N,N,N-tetra(methoxymethyl)glycoluryl is preferable.

The compound represented by the formula (5-3) can particularly be exemplified by compounds shown below.

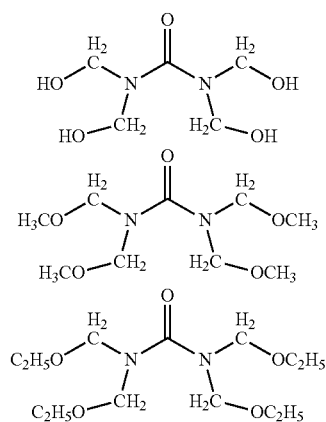

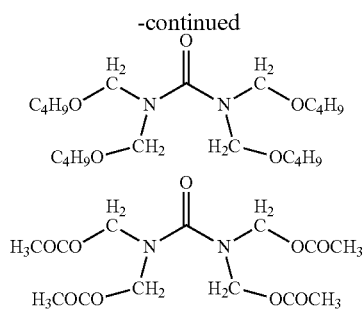

The alkoxymethylated melamine compound can particularly be exemplified by N,N,N,N,N,N-hexa(methoxymethyl)melamine, N,N,N,N,N,N-hexa(ethoxymethyl)melamine, N,N,N,N,N,N-hexa(n-propoxymethyl)melamine, N,N,N,N,N,N-hexa(isopropoxymethyl)melamine, N,N,N,N,N,N-hexa(n-butoxymethyl)melamine, N,N,N,N,N,N-hexa(t-butoxymethyl)melamine, and the like. Among them, particularly N,N,N,N,N,N-hexa(methoxymethyl)melamine is preferable.

The above acid crosslinking agent (G1) can be obtained by, for example, conducting a condensation reaction of a urea compound or a glycoluryl compound and formalin to introduce an methylol group, further etherifying lower alcohols such as methyl alcohol, ethyl alcohol, propyl alcohol and butyl alcohol, and then cooling the reaction solution to collect a precipitated compound or resin thereof. Moreover, the above acid crosslinking agent (G1) can also be obtained as a commercially available product such as CYMEL (trade name, made by MT AquaPolymer) and NIKALAC (made by Sanwa Chemical).

Also, the other particularly preferable acid crosslinking agent (G) can include a phenol derivative having 1 to 6 benzene rings within a molecule and two or more hydroxyalkyl groups and/or alkoxyalkyl groups within the entire molecule, the hydroxyalkyl groups and/or alkoxyalkyl groups being bonded to any of the above benzene rings (acid crosslinking agent (G2)). Preferably, a phenol derivative having a molecular weight of not more than 1500, 1 to 6 benzene rings and a total of two or more hydroxyalkyl groups and/or alkoxyalkyl groups within a molecule, the hydroxyalkyl groups and/or alkoxyalkyl groups being bonded to any of the above benzene rings, or a plurality of benzene rings can be included.

As the hydroxyalkyl group bonded to a benzene ring, the one of 1 to 6 carbons such as a hydroxylmethyl group, a 2-hydroxyethyl group and a 2-hydroxy-1-propyl group is preferable. As the alkoxyalkyl group bonded to a benzene ring, the one of 2 to 6 carbons is preferable. Particularly, a methoxymethyl group, an ethoxymethyl group, an n-propoxmethyl group, an isopropoxymethyl group, an n-butoxymethyl group, an isobutoxymethyl group, a sec-butoxymethyl group, a t-butoxymethyl group, a 2-methoxyethyl group, and a 2-methoxy-1-propyl group are preferable.

Among these phenol derivatives, particularly preferable ones are shown below.

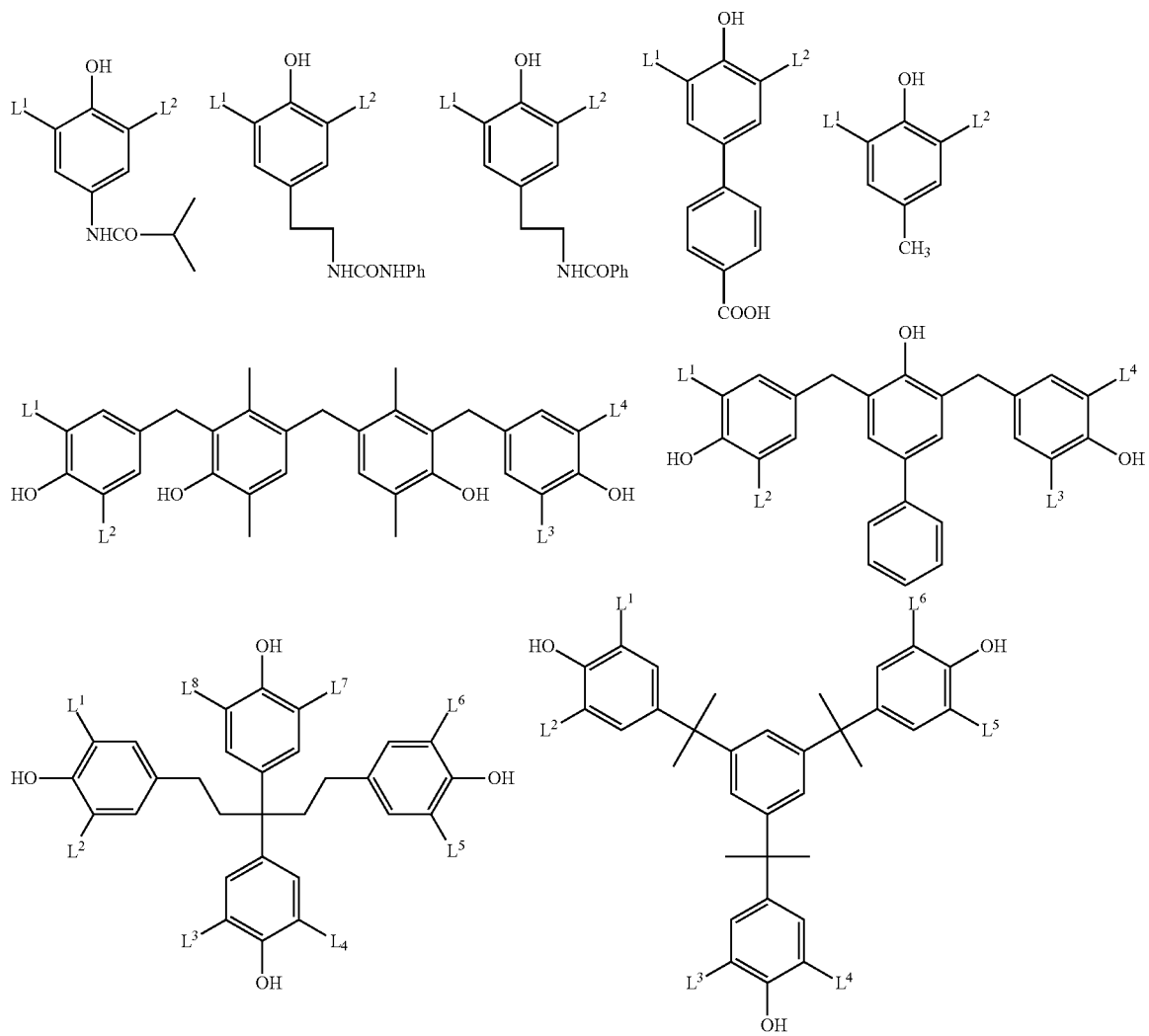

-continued
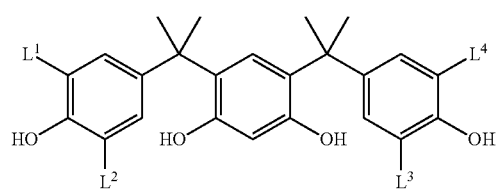
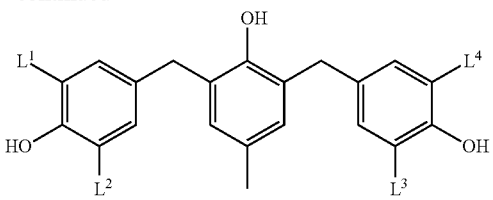
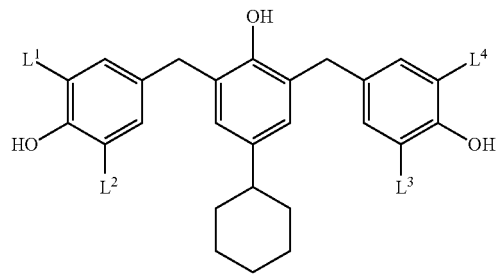
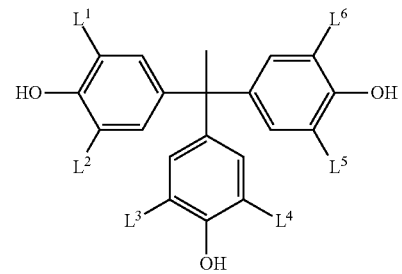
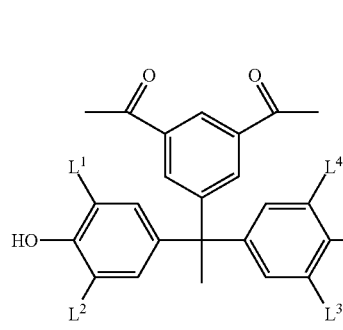
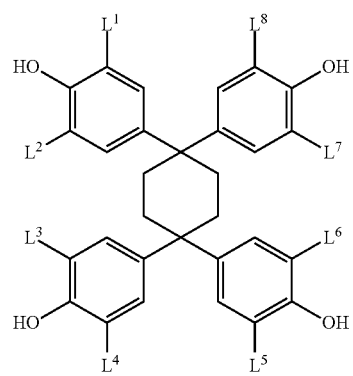
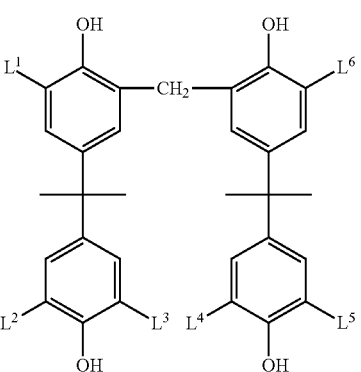
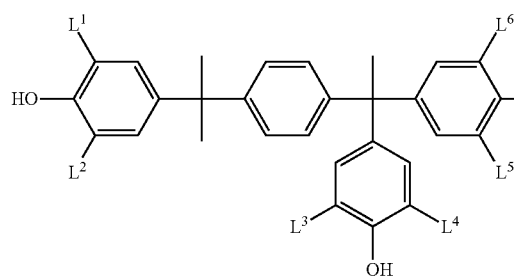
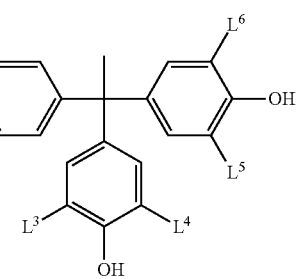
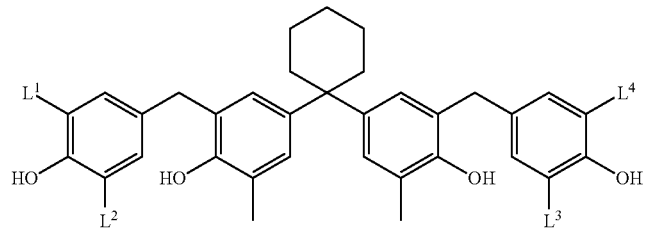
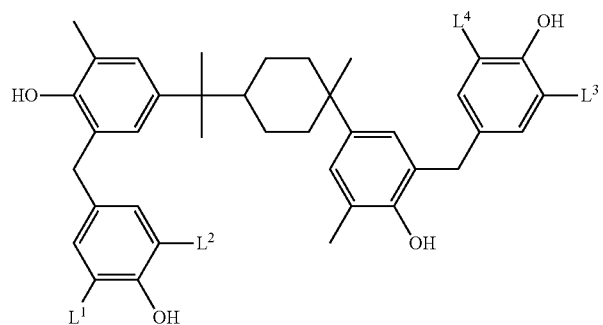

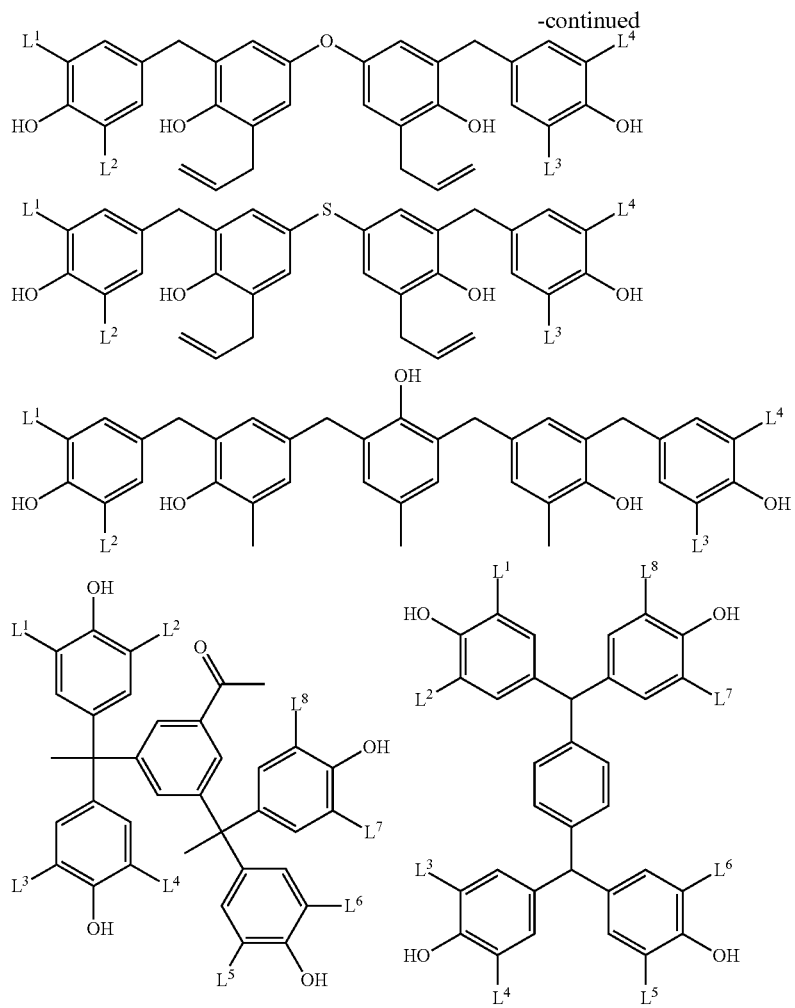

In the above formulae, L' to L⁸ may be the same or different, and each independently represents a hydroxymethyl group, a methoxymethyl group or an ethoxymethyl group. A phenol derivative having a hydroxymethyl group can be obtained by reacting the corresponding phenol compound having no hydroxylmethyl group (a compound where L¹ to L⁸ in the above formulae are a hydrogen atom) with formaldehyde in the presence of a basic catalyst. In this regard, in order to prevent resinification and gelation, the reaction temperature is preferably not more than 600° C. Particularly, it can be synthesized by methods described in JP-A-H6-282067, JP-A-H7-64285 and the like.

A phenol derivative having an alkoxymethyl group can be obtained by reacting the corresponding phenol derivative having a hydroxymethyl group with alcohol in the presence of an acid catalyst. In this regard, in order to prevent resinification and gelation, the reaction temperature is preferably not more than 100° C. Particularly, it can be synthesized by methods described in EP632003A, and the like.

While the phenol derivative having a hydroxymethyl group and/or an alkoxymethyl group thus synthesized is preferable in terms of stability upon storage, the phenol derivative having an alkoxymethyl group is particularly preferable in terms of stability upon storage. The acid crosslinking agent (G2) may be used alone, or may be used in combination of two or more kinds.

Moreover, the other particularly preferable acid crosslinking agent (G) can include a compound having at least one α-hydroxyisopropyl group (acid crosslinking agent (G3)). The compound is not particularly limited in the structure, as long as it has an α-hydroxyisopropyl group. In addition, a hydrogen atom of a hydroxyl group in the above α-hydroxyisopropyl group may be substituted with one or more kinds of acid dissociation group (R—COO-group, R—SO₂-group and the like, wherein R represents a substituent group selected from the group consisting of a linear hydrocarbon group of 1 to 12 carbons, a cyclic hydrocarbon group of 3 to 12 carbons, an alkoxy group of 1 to 12 carbons, a 1-branched alkyl group of 3 to 12 carbons and an aromatic hydrocarbon group of 6 to 12 carbons).

A compound having the above α-hydroxyisopropyl group is exemplified by one kind or two kinds or more of a substituted or unsubstituted aromatic based compound, a diphenyl compound, a naphthalene compound, a furan compound and the like containing at least one α-hydroxyisopropyl group. Particularly, it is exemplified by a compound represented by the following general formula (6-1) (hereinafter, referred to as "benzene based compound (1)"), a compound represented by the following general formula (6-2) (hereinafter, referred to as "diphenyl based compound (2)"), a compound represented by the following general formula (6-3) (hereinafter, referred to as "naphthalene based compound (3)"), a compound represented by the following general formula (6-4) (hereinafter, referred to as "furan based compound (4)"), and the like.

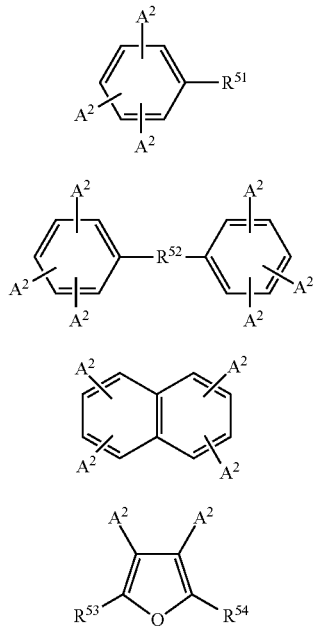

In the above general formulae (6-1) to (6-4), each $A^2$ independently represents an α-hydroxyisopropyl group or a hydrogen atom, and at least one $A^2$ is an α-hydroxyisopropyl group. Moreover, in the general formula (6-1), $R^{51}$ represents a hydrogen atom, a hydroxyl group, a linear or branched alkylcarbonyl group of 2 to 6 carbons, or a linear or branched alkoxycarbonyl group of 2 to 6 carbons. Furthermore, in the general formula (6-2), $R^{52}$ represents a single bond, a linear or branched alkylene group of 1 to 5 carbons, —O—, —CO—, or —COO—. Also, in the general formula (6-4), $R^{53}$ and $R^{54}$ represent a hydrogen atom or a linear or branched alkyl group of 1 to 6 carbons independently from each other.

The above benzene based compound (6-1) is particularly exemplified by α-hydroxyisopropylbenzenes such as α-hydroxyisopropylbenzene, 1,3-bis(α-hydroxyisopropyl)benzene, 1,4-bis(α-hydroxyisopropyl)benzene, 1,2,4-tris(α-hydroxyisopropyl)benzene and 1,3,5-tris(α-hydroxyisopropyl)benzene; α-hydroxyisopropylphenols such as 3-α-hydroxyisopropylphenol, 4-α-hydroxyisopropylphenol, 3,5-bis(α-hydroxyisopropyl)phenol and 2,4,6-tris(α-hydroxyisopropyl)phenol; α-hydroxyisopropylphenylalkylketones such as 3-α-hydroxyisopropyl-phenylmethylketone, 4-α-hydroxyisopropylphenylmethylketone, 4-α-hydroxyisopropyl-phenylethylketone, 4-α-hydroxyisopropylphenyl n-propylketone, 4-α-hydroxyisopropylphenyl isopropylketone, 4-α-hydroxyisopropyl-phenyl n-butylketone, 4-α-hydroxyisopropylphenyl t-butylketone, 4-α-hydroxyisopropylphenyl n-pentylketone, 3,5-bis(α-hydroxyisopropyl)phenyl methylketone, 3,5-bis(α-hydroxyisopropyl)phenyl ethylketone and 2,4,6-tris(α-hydroxyisopropyl)phenylmethylketone; alkyl 4-α-hydroxyisopropylbenzoates such as methyl 3-α-hydroxyisopropylbenzoate, methyl 4-α-hydroxyisopropylbenzoate, ethyl 4-α-hydroxyisopropylbenzoate, n-propyl 4-α-hydroxyisopropylbenzoate, isopropyl 4-α-hydroxyisopropylbenzoate, n-butyl 4-α-hydroxyisopropylbenzoate, t-butyl 4-α-hydroxyisopropylbenzoate, n-pentyl 4-α-hydroxyisopropylbenzoate, methyl 3,5-bis(α-hydroxyisopropyl)benzoate, ethyl 3,5-bis(α-hydroxyisopropyl)benzoate and methyl 2,4,6-tris(α-hydroxyisopropyl)benzoate, and the like.

Moreover, the above diphenyl based compound (6-2) is particularly exemplified by α-hydroxyisopropylbiphenyls such as 3-α-hydroxyisopropylbiphenyl, 4-α-hydroxyisopropylbiphenyl, 3,5-bis(α-hydroxyisopropyl)biphenyl, 3,3'-bis(α-hydroxyisopropyl)biphenyl, 3,4'-bis(α-hydroxyisopropyl)biphenyl, 4,4'-bis(α-hydroxyisopropyl)biphenyl, 2,4,6-tris(α-hydroxyisopropyl)biphenyl, 3,3',5-tris(α-hydroxyisopropyl)biphenyl, 3,4',5-tris(α-hydroxyisopropyl)biphenyl, 2,3',4,6-tetrakis(α-hydroxyisopropyl)biphenyl, 2,4,4',6-tetrakis(α-hydroxyisopropyl)biphenyl, 3,3',5,5'-tetrakis(α-hydroxyisopropyl)biphenyl, 2,3',4,5',6-pentakis(α-hydroxyisopropyl)biphenyl and 2,2',4,4',6,6'-hexakis(α-hydroxyisopropyl)biphenyl;

α-hydroxyisopropyldiphenylalkanes such as 3-α-hydroxyisopropyldiphenylmethane, 4-α-hydroxyisopropyldiphenylmethane, 1-(4-α-hydroxyisopropyl-phenyl)-2-phenylethane, 1-(4-α-hydroxyisopropyl-phenyl)-2-phenylpropane, 2-(4-α-hydroxyisopropylphenyl)-2-phenylpropane, 1-(4-α-hydroxyisopropylphenyl)-3-phenylpropane, 1-(4-α-hydroxyisopropylphenyl)-4-phenylbutane, 1-(4-α-hydroxyisopropyl-phenyl)-5-phenylpentane, 3,5-bis(α-hydroxyisopropyl)diphenylmethane, 3,3'-bis(α-hydroxyisopropyl)diphenylmethane, 3,4'-bis(α-hydroxyisopropyl)diphenylmethane, 4,4'-bis(α-hydroxyisopropyl)diphenylmethane, 1,2-bis(4-α-hydroxyisopropylphenyl)ethane, 1,2-bis(4-α-hydroxypropylphenyl)propane, 2,2-bis(4-α-hydroxypropylphenyl)propane, 1,3-bis(4-α-hydroxypropylphenyl)propane, 2,4,6-tris(α-hydroxyisopropyl)diphenylmethane, 3,3',5-tris(α-hydroxyisopropyl)diphenylmethane, 3,4',5-tris(α-hydroxyisopropyl)diphenylmethane, 2,3'4,6-tetrakis(α-hydroxyisopropyl)diphenylmethane, 2,4,4',6-tetrakis(α-hydroxyisopropyl)diphenylmethane, 3,3',5,5'-tetrakis(α-hydroxyisopropyl)diphenylmethane, 2,3'4,5',6-pentakis(α-hydroxyisopropyl)diphenylmethane and 2,2',4,4',6,6'-hexakis(α-hydroxyisopropyl)diphenylmethane;

α-hydroxyisopropyldiphenylethers such as 3-α-hydroxyisopropyldiphenylether, 4-α-hydroxyisopropyldiphenylether, 3,5-bis(α-hydroxyisopropyl)diphenylether, 3,3'-bis(α-hydroxyisopropyl)diphenylether, 3,4'-bis(α-hydroxyisopropyl)diphenylether, 4,4'-bis(α-hydroxyisopropyl)diphenylether, 2,4,6-tris(α-hydroxyisopropyl)diphenylether, 3,3',5-tris(α-hydroxyisopropyl)diphenylether, 3,4',5-tris(α-hydroxyisopropyl)diphenylether, 2,3',4,6-tetrakis(α-hydroxyisopropyl)diphenylether, 2,4,4',6-tetrakis(α-hydroxyisopropyl)diphenylether, 3,3',5,5'-tetrakis(α-hydroxyisopropyl)diphenylether, 2,3',4,5',6-pentakis(α-hydroxyisopropyl)diphenylether and 2,2',4,4',6,6'-hexakis(α-hydroxyisopropyl)diphenylether;

α-hydroxyisopropyldiphenylketones such as 3-α-hydroxyisopropyldiphenylketone, 4-α-hydroxyisopropyldiphenylketone, 3,5-bis(α-hydroxyisopropyl)diphenylketone, 3,3'-bis(α-hydroxyisopropyl)diphenylketone, 3,4'-bis(α-hydroxyisopropyl)diphenylketone, 4,4'-bis(α-hydroxyisopropyl)diphenylketone, 2,4,6-tris(α-hydroxyisopropyl)diphenylketone, 3,3',5-tris(α-hydroxyisopropyl)diphenylketone, 3,4',5-tris(α-hydroxyisopropyl)diphenylketone, 2,3',4,6-tetrakis(α- hydroxyisopropyl)diphenylketone, 2,4,4',6-tetrakis(α-hydroxyisopropyl)diphenylketone, 3,3',5,5'-tetrakis(α-hydroxyisopropyl)diphenylketone, 2,3',4,5',6-pentakis(α-hydroxyisopropyl)diphenylketone and 2,2',4,4',6,6'-hexakis (α-hydroxyisopropyl)diphenylketone; phenyl α-hydroxyisopropylbenzoates such as phenyl 3-α-hydroxyisopropylbenzoate, phenyl 4-α-hydroxyisopropylbenzoate, 3-α-hydroxyisopropylphenylbenzoate, 4-α-hydroxyisopropyl-phenyl benzoate, phenyl 3,5-bis(α-hydroxyisopropyl) benzoate, 3-α-hydroxyisopropyl-phenyl 3-α-hydroxyisopropylbenzoate, 4-α-hydroxyisopropyl-phenyl 3-α-hydroxyisopropylbenzoate, 3-α-hydroxyisopropyl-phenyl 4-α-hydroxyisopropylbenzoate, 4-α-hydroxyisopropylphenyl 4-α-hydroxyisopropylbenzoate, 3,5-bis(α-hydroxyisopropyl)phenylbenzoate, phenyl 2,4,6-tris(α-hydroxyisopropyl)benzoate, 3-α-hydroxyisopropylphenyl 3,5-bis(α-hydroxyisopropyl)benzoate, 4-α-hydroxyisopropylphenyl 3,5-bis(α-hydroxyisopropyl)benzoate, 3,5-bis(α-hydroxyisopropyl)phenyl 3-α-hydroxyisopropylbenzoate, 3,5-bis(α-hydroxyisopropyl)phenyl 4-α-hydroxyisopropylbenzoate, 2,4,6-tris(α-hydroxyisopropyl)phenyl benzoate, 3-α-hydroxyisopropyl-phenyl 2,4,6-tris(α-hydroxyisopropyl)benzoate, 4-α-hydroxyisopropylphenyl 2,4,6-tris(α-hydroxyisopropyl)benzoate, 3,5-bis(α-hydroxyisopropyl)phenyl 3,5-bis (α-hydroxyisopropyl)benzoate, 2,4,6-tris(α-hydroxyisopropyl)phenyl 3-α-hydroxyisopropylbenzoate, 2,4,6-tris(α-hydroxyisopropyl)phenyl 4-α-hydroxyisopropylbenzoate, 3,5-bis(α-hydroxyisopropyl)phenyl 2,4,6-tris (α-hydroxyisopropyl)benzoate, 2,4,6-tris(α-hydroxyisopropyl)phenyl 3,5-bis(α-hydroxyisopropyl)benzoate and 2,4,6-tris(α-hydroxyisopropyl)phenyl 2,4,6-tris(α-hydroxyisopropyl)benzoate, and the like.

Furthermore, the above naphthalene based compound (6-3) is particularly exemplified by 1-(α-hydroxyisopropyl) naphthalene, 2-(α-hydroxyisopropyl)naphthalene, 1,3-bis (α-hydroxyisopropyl)naphthalene, 1,4-bis(α-hydroxyisopropyl)naphthalene, 1,5-bis(α-hydroxyisopropyl) naphthalene, 1,6-bis(α-hydroxyisopropyl)naphthalene, 1,7-bis(α-hydroxyisopropyl)naphthalene, 2,6-bis(α-hydroxyisopropyl)naphthalene, 2,7-bis(α-hydroxyisopropyl)naphthalene, 1,3,5-tris(α-hydroxyisopropyl)naphthalene, 1,3,6-tris(α-hydroxyisopropyl)naphthalene, 1,3,7-tris(α-hydroxyisopropyl)naphthalene, 1,4,6-tris(α-hydroxyisopropyl)naphthalene, 1,4,7-tris(α-hydroxyisopropyl)naphthalene, 1,3,5,7-tetrakis(α-hydroxyisopropyl)naphthalene and the like.

Also, the above furan based compound (6-4) is particularly exemplified by 3-(α-hydroxyisopropyl)furan, 2-methyl-3-(α-hydroxyisopropyl)furan, 2-methyl-4-α-hydroxyisopropyl)furan, 2-ethyl-4-(α-hydroxyisopropyl)furan, 2-n-propyl-4-α-hydroxyisopropyl)furan, 2-isopropyl-4-(α-hydroxyisopropyl)furan, 2-n-butyl-4-α-hydroxyisopropyl) furan, 2-t-butyl-4-(α-hydroxyisopropyl)furan, 2-n-pentyl-4-α-hydroxyisopropyl)furan, 2,5-dimethyl-3-(α-hydroxyisopropyl)furan, 2,5-diethyl-3-α-hydroxyisopropyl) furan, 3,4-bis(α-hydroxyisopropyl)furan, 2,5-dimethyl-3,4-bis(α-hydroxyisopropyl)furan, 2,5-diethyl-3,4-bis(α-hydroxyisopropyl)furan and the like.

As the above acid crosslinking agent (G3), a compound having two or more free α-hydroxyisopropyl groups is preferable, the above benzene based compound (6-1) having two or more α-hydroxyisopropyl groups, the above diphenyl based compound (6-2) having two or more α-hydroxyisopropyl groups and the above naphthalene based compound (6-3) having two or more α-hydroxyisopropyl groups are further preferable, and α-hydroxyisopropylbiphenyls having two or more α-hydroxyisopropyl groups and the above naphthalene based compound (6-3) having two or more α-hydroxyisopropyl groups are particularly preferable.

The above acid crosslinking agent (G3) can normally be obtained by a method of reacting an acetyl group-containing compound such as 1,3-diacetylbenzene with Grignard reagent such as $CH_3MgBr$ to methylate and then hydrolyzing, or a method of oxidizing an isopropyl group-containing compound such as 1,3-diisopropylbenzene with oxygen and the like to produce a peroxide and then reducing.

The compounding proportion of the acid crosslinking agent (G) in the invention is 1 to 100 parts by weight per 100 parts by weight of the cyclic compound represented by the formula (6-1), preferably 1 to 80 parts by weight, more preferably 2 to 60 parts by weight, and particularly preferably 4 to 40 parts by weight. When the compounding proportion of the above acid crosslinking agent (G) is not less than 0.5 parts by weight, the inhibiting effect of the solubility of a resist film in an alkaline developing solution can be improved, and a decrease in the film remaining rate, and occurrence of swelling and meandering of a resist pattern can be inhibited, which is preferable, while when it is not more than 50 parts by weight, a decrease in heat resistance as a resist can be inhibited, which is preferable.

Moreover, the compounding proportion of at least one kind of compound selected from the above acid crosslinking agent (G1), acid crosslinking agent (G2) and acid crosslinking agent (G3) in the above acid crosslinking agent (G) is also not particularly limited, and can be within various ranges according to the kind of substrates used upon forming a resist pattern.

In all acid crosslinking agent components, the above alkoxymethylated melamine compound and/or the compounds represented by (6-1) to (6-3) are 50 to 99% by weight, preferably 60 to 99% by weight, more preferably 70 to 98% by weight, and further preferably 80 to 97% by weight. By having the alkoxymethylated melamine compound and/or the compounds represented by (6-1) to (6-3) of not less than 50% by weight of all acid crosslinking agent components, the resolution can be improved, which is preferable, while by having it of not more than 99% by weight, it is easy for the resist pattern cross section to be a rectangular shape, which is preferable.

In the invention, an acid diffusion controlling agent (E) having a function of controlling diffusion of an acid generated from an acid generating agent by radiation irradiation in a resist film to inhibit any unpreferable chemical reaction at an unexposed region may be compounded in a radiation-sensitive composition. By using such an acid diffusion controlling agent (E), the storage stability of a radiation-sensitive composition improves. Also, along with the improvement of the resolution, the line width change of a resist pattern due to variation in the post exposure delay time before electron beam irradiation and the post exposure delay time after electron beam irradiation can be inhibited, and the composition becomes excellent in process stability.

Such acid diffusion controlling agent (E) includes an electron beam radiation degradable basic compound such as a nitrogen atom-containing basic compound, a basic sulfonium compound and a basic iodonium compound. The acid diffusion controlling agent can be used alone or in combination of two or more kinds.

The above acid diffusion controlling agent is exemplified by a nitrogen-containing organic compound, a basic compound degradable by exposure and the like. The above nitrogen containing organic compound can be exemplified by a compound represented by the following general formula (7):

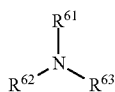
(7)

(hereinafter, referred to as "nitrogen-containing compound (I)"), a diamino compound having two nitrogen atoms within the same molecule (hereinafter, referred to as "nitrogen-containing compound (II)"), a polyamino compound or polymer having three or more nitrogen atoms (hereinafter, referred to as "nitrogen containing compound (III)"), an amide group-containing compound, a urea compound, a nitrogen-containing heterocyclic compound, and the like. In addition, the above acid diffusion controlling agent may be used alone as one kind or may be used in combination of two or more kinds.

In the above general formula (7), $R^{61}$, $R^{62}$ and $R^{63}$ represent a hydrogen atom, a linear, branched or cyclic alkyl group, an aryl group, or an aralkyl group independently from each other. Also, the above alkyl group, aryl group, or aralkyl group may be unsubstituted or may be substituted with the other functional group such as a hydroxyl group. Here, the above linear, branched or cyclic alkyl group is exemplified by the one of 1 to 15, preferably 1 to 10 carbons, and is particularly exemplified by a methyl group, an ethyl group, an n-propyl group, an isopropyl group, an n-butyl group, an isobutyl group, a sec-butyl group, a t-butyl group, an n-pentyl group, a neopentyl group, an n-hexyl group, a texyl group, an n-heptyl group, an n-octyl group, an n-ethylhexyl group, an n-nonyl group, an n-decyl group, and the like. Moreover, the above aryl group includes the one of 6 to 12 carbons, and particularly includes a phenyl group, a tolyl group, a xylyl group, a cumenyl group, a 1-naphthyl group, and the like. Furthermore, the above aralkyl group includes the one of 7 to 19, preferably 7 to 13 carbons, and particularly includes a benzyl group, an α-methylbenzyl group, a phenethyl group, a naphthyl group and the like.

The above nitrogen-containing compound (I) can particularly be exemplified by mono(cyclo)alkylamines such as n-hexylamine, n-heptylamine, n-octylamine, n-nonylamine, n-decylamine, n-dodecylamine and cyclohexylamine; di(cyclo)alkylamines such as di-n-butylamine, di-n-pentylamine, di-n-hexylamine, di-n-heptylamine, di-n-octylamine, di-n-nonylamine, di-n-decylamine, methyl-n-dodecylamine, di-n-dodecylmethyl, cyclohexylmethylamine and dicyclohexylamine; tri(cyclo)alkylamines such as triethylamine, tri-n-propylamine, tri-n-butylamine, tri-n-pentylamine, tri-n-hexylamine, tri-n-heptylamine, tri-n-octylamine, tri-n-nonylamine, tri-n-decylamine, dimethyl-n-dodecylamine, di-n-dodecylmethylamine, dicyclohexylmethylamine and tricyclohexylamine; alkanolamines such as monoethanolamine, diethanolamine and triethanolamine; aromatic amines such as aniline, N-methylaniline, N,N-dimethylaniline, 2-methylaniline, 3-methylaniline, 4-methylaniline, 4-nitroaniline, diphenylamine, triphenylamine and 1-naphthylamine, and the like.

The above nitrogen-containing compound (II) can particularly be exemplified by ethylenediamine, N,N,N',N'-tetramethylethylenediamine, N,N,N',N'-tetrakis(2-hydroxylpropyl) ethylenediamine, tetramethylenediamine, hexamethylenediamine, 4,4'-diaminodiphenylmethane, 4,4'-diaminodiphenylether, 4,4'-diaminobenzophenone, 4,4'-diaminodiphenylamine, 2,2-bis(4-aminophenyl)propane, 2-(3-aminophenyl)-2-(4-aminophenyl)propane, 2-(4-aminophenyl)-2-(3-hydroxyphenyl)propane, 2-(4-aminophenyl)-2-(4-hydroxyphenyl)propane, 1,4-bis[1-(4-aminophenyl)-1-methylethyl]benzene, 1,3-bis[1-(4-aminophenyl)-1-methylethyl]benzene and the like.

The above nitrogen-containing compound (III) can particularly be exemplified by polymers of polyethyleneimine, polyarylamine and N-(2-dimethylaminoethyl)acrylamide, and the like.

The above amide group-containing compound can particularly be exemplified by formamide, N-methylformamide, N,N-dimethylformamide, acetamide, N-methylacetamide, N,N-dimethylacetamide, propioneamide, benzamide, pyrrolidon, N-methylpyrrolidon and the like.

The above urea compound can particularly be exemplified by urea, methylurea, 1,1-dimethylurea, 1,3-dimethylurea, 1,1,3,3-tetramethylurea, 1,3-diphenylurea, tri-n-butylthiourea and the like.

The above nitrogen-containing heterocyclic compound can particularly be exemplified by imidazoles such as imidazole, benzimidazole, 4-methylimidazole, 4-methyl-2-phenylimidazole, 2-phenylbenzimidazole and 2,4,5-triphenylimidazole; pyridines such as pyridine, 2-methylpyridine, 4-methylpyridine, 2-ethylpyridine, 4-ethylpyridine, 2-phenylpyridine, 4-phenylpyridine, 2-methyl-4-phenylpyridine, nicotine, nicotinic acid, amide nicotinate, quinoline, 8-oxyquinoline and acridine; and pyrazine, pyrazole, pyridazine, quinozaline, purine, pyrrolidine, piperidine, morpholine, 4-methylmorpholine, piperazine, 1,4-dimethylpiperazine, 1,4-diazabicyclo[2.2.2]octane and the like.

Also, the above basic compound degradable by exposure can particularly be exemplified by a sulfonium compound represented by the following general formula (8-1):

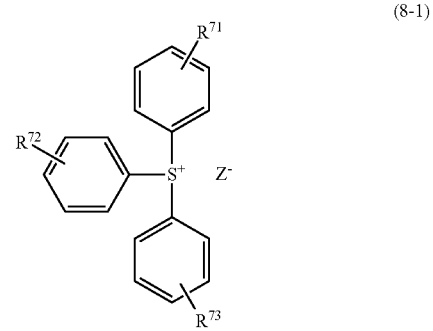
(8-1)

an iodonium compound represented by the following general formula (8-2):

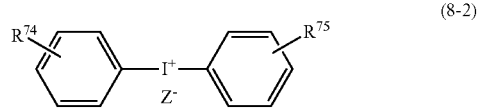
(8-2)

and the like.

In the above general formulae (8-1) and (8-2), $R^{71}$, $R^{72}$, $R^{73}$, $R^{74}$ and $R^{75}$ represent a hydrogen atom, an alkyl group of 1 to 6 carbons, an alkoxyl group of 1 to 6 carbons, a hydroxyl group or a halogen atom independently from each other. $Z^-$ represents $HO^-$, $R$—$COO^-$ (provided that R represents an alkyl group of 1 to 6 carbons, an aryl group of 1 to 6 carbons or an alkaryl group of 1 to 6 carbons) or an anion represented by the following general formula (8-3):

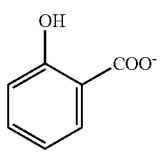

(8-3)

The above basic compound degradable by exposure is particularly exemplified by triphenylsulfonium hydroxide, triphenylsulfonium acetate, triphenylsulfonium salicylate, diphenyl-4-hydroxyphenylsulfonium hydroxide, diphenyl-4-hydroxyphenylsulfonium acetate, diphenyl-4-hydroxyphenylsulfonium salicylate, bis(4-t-butylphenyl) iodonium hydroxide, bis(4-t-butyl-phenyl)iodonium acetate, bis(4-t-butylphenyl)iodonium salicylate, 4-t-butylphenyl-4-hydroxyphenyliodonium hydroxide, 4-t-butylphenyl-4-hydroxyphenyliodonium acetate, 4-t-butylphenyl-4-hydroxyphenyliodonium salicylate and the like.

The compounding amount of the acid diffusion controlling agent (E) is preferably 0.001 to 50% by weight of the total weight of solid component, more preferably 0.001 to 10% by weight, further preferably 0.001 to 5% by weight, and particularly preferably 0.001 to 3% by weight. Within the above range, a decrease in resolution, and deterioration of the resist pattern shape, the dimension fidelity and the like can be prevented. Moreover, even though the post exposure delay time from electron beam irradiation to heating after radiation irradiation becomes longer, the shape of the resist pattern upper layer portion is not deteriorated. Also, when the compounding amount is not more than 10% by weight, a decrease in sensitivity, developability of the unexposed portion and the like can be prevented. In addition, by using such an acid diffusion controlling agent, the storage stability of a radiation-sensitive composition improves, also along with improvement of the resolution, the line width change of a resist pattern due to variation in the post exposure delay time before radiation irradiation and the post exposure delay time after radiation irradiation can be inhibited, and the composition becomes excellent in process stability.

To the radiation-sensitive composition of the invention, within the range of not inhibiting the purpose of the invention, if required, as the other component (F), one kind or two kinds or more of various additive agents such as dissolution promoting agent, dissolution controlling agent, sensitizing agent, surfactant, and organic carboxylic acid or oxo acid of phosphor or derivative thereof can be added.

[1] Dissolution Promoting Agent

A low molecular weight dissolution promoting agent is a component having a function of increasing the solubility to moderately increase the dissolution rate of a cyclic compound upon developing, when the solubility of the cyclic compound represented by the formula (1) in a developing solution such as an alkali is too low, and can be used within the range of not deteriorating the effect of the invention. The above dissolution promoting agent can be exemplified by a low molecular weight phenolic compound, and can be exemplified by bisphenols, tris(hydroxyphenyl)methane and the like. These dissolution promoting agents can be used alone or in mixture of two or more kinds.

The compounding amount of the dissolution promoting agent, which is arbitrarily adjusted according to the kind of cyclic compound to be used, is 0 to 100 parts by weight per 100 parts by weight of the cyclic compound represented by the formula (1), preferably 0 to 30 parts by weight, more preferably 0 to 10 parts by weight, and further preferably 0 to 2 parts by weight.

[2] Dissolution Controlling Agent

The dissolution controlling agent is a component having a function of controlling the solubility to moderately decrease the dissolution rate upon developing, when the solubility of the cyclic compound represented by the formula (1) in a developing solution such as an alkali is too high. As such a dissolution controlling agent, the one which does not chemically change in steps such as calcination of resist coating, radiation irradiation and development is preferable.

The dissolution controlling agent can be exemplified by aromatic hydrocarbons such as naphthalene, phenanthrene, anthracene and acenaphthene; ketones such as acetophenone, benzophenone and phenyl naphtyl ketone; sulfones such as methyl phenyl sulfone, diphenyl sulfone and dinaphthyl sulfone, and the like. These dissolution controlling agents can be used alone or in two or more kinds.

The compounding amount of the dissolution controlling agent, which is arbitrarily adjusted according to the kind of cyclic compound to be used, is 0 to 100 parts by weight per 100 parts by weight of the cyclic compound represented by the formula (1), preferably 0 to 30 parts by weight, more preferably 0 to 10 parts by weight, and further preferably 0 to 2 parts by weight.

[3] Sensitizing Agent

The sensitizing agent is a component having a function of absorbing irradiated radiation energy, transmitting the energy to the acid generating agent (C) and thereby increasing the acid production amount, and improving the apparent sensitivity of a resist. Such a sensitizing agent can be exemplified by benzophenones, biacetyls, pyrenes, phenothiazines, fluorenes and the like, but is not particularly limited. These sensitizing agents can be used alone or in two or more kinds.

The compounding amount of the sensitizing agent, which is arbitrarily adjusted according to the kind of cyclic compound to be used, is 0 to 100 parts by weight per 100 parts by weight of the cyclic compound represented by the formula (1), preferably 0 to 30 parts by weight, more preferably 0 to 10 parts by weight, and further preferably 0 to 2 parts by weight.

[4] Surfactant

The surfactant is a component having a function of improving coatability and striation of the radiation-sensitive composition of the invention, and developability of a resist and the like. Such a surfactant may be any of anionic, cationic, nonionic or amphoteric. A preferable surfactant is a nonionic surfactant. The nonionic surfactant has a good affinity with a solvent used in production of radiation-sensitive compositions and more effects.

Examples of the nonionic surfactant include, but not particularly limited to, a polyoxyethylene higher alkyl ethers, polyoxyethylene higher alkyl phenyl ethers, higher fatty acid diesters of polyethylene glycol, and the like. Commercially available products can include, hereinafter by trade name, EFTOP (made by Jemco), MEGAFAC (made by DIC), Fluorad (made by Sumitomo 3M), AsahiGuard, Surflon (hereinbefore, made by Asahi Glass), Pepole (made by TOHO Chemical Industry), KP (made by Shin-Etsu Chemical), Polyflow (made by Kyoeisha Chemical) and the like can be included.

The compounding amount of the surfactant, which is arbitrarily adjusted according to the kind of cyclic compound to be used, is 0 to 100 parts by weight per 100 parts by weight of the cyclic compound represented by the formula (1), preferably 0 to 30 parts by weight, more preferably 0 to 10 parts by weight, and further preferably 0 to 2 parts by weight.

[5] Organic Carboxylic Acid or Oxo Acid of Phosphor or Derivative Thereof

For the purpose of prevention of sensitivity deterioration or prevention of collapse and peeling of a resist pattern, and improvement of resist pattern shape, post exposure delay stability and the like, and as an additional optional component, an organic carboxylic acid or an oxo acid of phosphor or derivative thereof can be contained. In addition, it can be used in combination with the acid diffusion controlling agent, or may be used alone.

As the organic carboxylic acid, for example, malonic acid, citric acid, malic acid, succinic acid, benzoic acid, salicylic acid, and the like are preferable. The oxo acid of phosphor or derivative thereof includes phosphoric acid or derivative thereof such as ester including phosphoric acid, di-n-butyl ester phosphate and diphenyl ester phosphate, phosphonic acid or derivative thereof such as ester including phosphonic acid, dimethyl ester phosphonate, di-n-butyl ester phosphonate, phenylphosphonic acid, diphenyl ester phosphonate and dibenzyl ester phosphonate, phosphinic acid and derivative thereof such ester including phosphinic acid and phenylphosphinic acid, and phosphonic acid is particularly preferable among them.

The organic carboxylic acid or the oxo acid of phosphorous or derivative thereof can be used alone or in combination of two or more kinds. The compounding amount of the organic carboxylic acid or the oxo acid of phosphorous or derivative thereof, which is arbitrarily adjusted according to the kind of cyclic compound to be used, is 0 to 100 parts by weight per 100 parts by weight of the cyclic compound represented by the formula (1), preferably 0 to 30 parts by weight, more preferably 0 to 10 parts by weight, and further preferably 0 to 2 parts by weight.

[6] Other Additive Agent Than the Above Dissolution Controlling Agent, Sensitizing Agent, Surfactant, and Organic Carboxylic Acid or Oxo Acid of Phosphorous or Derivative Thereof Furthermore, to the radiation-sensitive composition of the invention, within the range of not inhibiting the purpose of the invention, if required, one kind or two kinds or more of additive agent other than the above dissolution controlling agent, sensitizing and surfactant can be compounded. Such an additive agent is exemplified by dye, pigment, adhesion aid and the like. For example, by compounding dye or pigment, a latent image of the exposed portion can be visualized and influence of halation upon exposure can be alleviated, which is preferable. Moreover, by compounding an adhesion aid, adhesiveness to a substrate can be improved, which is preferable. Furthermore, other additive agents can include halation preventing agent, storage stabilizing agent, defoaming agent, shape improving agent and the like, and particularly include 4-hydroxy-4'-methylchalkone and the like.

The compounding of the radiation-sensitive composition of the invention (cyclic compound/acid generating agent (C)/acid crosslinking agent (G)/acid diffusion controlling agent (E)/optional component (F)) is, in % by weight based on solid content, preferably
50 to 99.489/0.001 to 49.49/0.5 to 49.989/0.01 to 49.499/0 to 49.489, more preferably
50 to 99.489/0.001 to 49.49/0.5 to 40/0.01 to 5/0 to 15, further preferably
60 to 70/10 to 25/1 to 30/0.01 to 3/0 to 1, and particularly preferably
60 to 70/10 to 25/2 to 20/0.01 to 3/0. With the above compounding, it is excellent in performance such as sensitivity, resolution and alkaline developability.

The radiation-sensitive composition of the invention is normally prepared by dissolving each component in a solvent upon use into a homogenous solution, and then if required, filtering through a filter and the like with a pore diameter of 0.2 μm, for example.

The solvent used for preparing the radiation-sensitive composition of the invention is basically not limited as long as it satisfies the solubility of each component of the composition and the coatability of the curable composition, but a safe solvent selected in consideration of the solubility, coatibility and safety of a binder is preferable.

The above safe solvent can be exemplified by, but not particularly limited to, ethylene glycol monoalkyl ether acetates such as ethylene glycol monomethyl ether acetate, ethylene glycol monoethyl ether acetate, ethylene glycol mono-n-propyl ether acetate and ethylene glycol mono-n-butyl ether acetate; ethylene glycol monoalkyl ethers such as ethylene glycol monomethyl ether and ethylene glycol monoethyl ether; propylene glycol monoalkyl ether acetates such as propylene glycol monomethyl ether acetate, propylene glycol monoethyl ether acetate, propylene glycol mono-n-propyl ether acetate and propylene glycol mono-n-butyl ether acetate; propylene glycol monoalkyl ethers such as propylene glycol monomethyl ether and propylene glycol monoethyl ether; ester lactates such methyl lactate, ethyl lactate, n-propyl lactate, n-butyl lactate and n-amyl lactate; aliphatic carboxylic acid esters such as methyl acetate, ethyl acetate, n-propyl acetate, n-butyl acetate, n-amyl acetate, n-hexyl acetate, methyl propionate and ethylpropionate; other esters such as methyl 3-methoxypropionate, ethyl 3-methoxypropionate, methyl 3-ethoxypropionate, ethyl 3-ethoxypropionate, methyl 3-methoxy-2-methylpropionate, 3-methoxybutylacetate, 3-methyl-3-methoxybutylacetate, butyl 3-methoxy-3-methylpropionate, butyl 3-methoxy-3-methylbutyrate, methyl acetoacetate, methyl pyruvate and ethyl pyruvate; aromatic hydrocarbons such as toluene and xylene; ketones such as 2-heptanone, 3-heptanone, 4-heptanone, cyclopentanone and cyclohexanone; amides such as N,N-dimethylformamide, N-methylacetamide, N,N-dimethylacetamide and N-methylpyrrolidone; lactones such as γ-lactone, and the like. These solvents can be used alone or in two or more kinds.

The radiation-sensitive composition of the invention can contain a resin soluble in an alkaline aqueous solution within the range of not inhibiting the purpose of the invention. The resin soluble in an alkaline aqueous solution includes novolac resin, polyvinyl phenols, polyacrylic acid, polyvinyl alcohol, styrene-maleic anhydride resin, and polymer containing acrylic acid, vinyl alcohol or vinylphenol as a monomeric unit, or derivative thereof and the like.

The compounding amount of the resin soluble in an alkaline aqueous solution, which is arbitrarily adjusted according to the kind of cyclic compound represented by the formula (1) to be used, is preferably not more than 30 parts by weight per 100 parts by weight of the above cyclic compound, more preferably not more than 10 parts by weight, further preferably not more than 5 parts by weight, and particularly preferably 0 part by weight.

[Resist Pattern Formation Method]

The invention relates to a resist pattern formation method including steps of forming a resist film on a substrate using the above radiation-sensitive composition of the invention, exposing the resist film, and developing the resist film to form a resist pattern. The resist pattern of the invention can also be formed as an upper layer resist in a multilayer resist process.

In order to form a resist pattern, a resist film is formed by coating the above radiation-sensitive composition of the invention onto a conventionally publically known substrate using a coating means such as spin coating, flow casting coating and roll coating. The conventionally publically known substrate is not particularly limited, but can be exemplified by a substrate for electronic components, the one having a predetermined wiring resist pattern formed thereon, and the like. More particularly, it is exemplified by a substrate made of metal such as silicon wafer, copper, chromium, iron and aluminum, a glass substrate and the like.

A wiring resist pattern material is exemplified by copper, aluminum, nickel, gold and the like. Also if required, it may be a substrate as described above having an inorganic and/or organic coating provided thereon. The inorganic coating includes an inorganic antireflection coating (inorganic BARC). The organic coating includes an organic antireflection coating (organic BARC). Surface treatment with hexamethylene disilazane and the like may be conducted.

Next, if required, the coated substrate is heated. The heating conditions vary according to the compounding composition of the radiation-sensitive composition, but are preferably 20 to 250° C., more preferably 20 to 150° C. By heating, the adhesiveness of a resist to a substrate may improve, which is preferable. Then, the resist film is exposed to a desired resist pattern by any radiation selected from the group consisting of visible light, ultraviolet, excimer laser, electron beam, extreme ultraviolet (EUV), X-ray and ion beam. The exposure conditions and the like are arbitrarily selected according to the compounding composition of the radiation-sensitive composition, and the like. In the invention, in order to stably form a fine resist pattern with a high degree of accuracy in exposure, it is preferable to heat after radiation irradiation. The heating conditions vary according to the compounding composition of the radiation-sensitive composition and the like, but are preferably 20 to 250° C., more preferably 20 to 150° C.

Next, by developing the exposed resist film in an alkaline developing solution, a predetermined resist pattern is formed. As the above alkaline developing solution, for example, an alkaline aqueous solution having one or more kinds of alkaline compound such as mono-, di- or tri-alkylamines, mono-, di- or tri-alkanolamines, heterocyclic amines, tetramethyl ammonium hydroxide (TMAH) and choline dissolved such that the concentration is preferably 1 to 10% by mass, and more preferably 1 to 5% by mass can be used. When the concentration of the above alkaline aqueous solution is not more than 10% by mass, the exposed portion can be prevented from being dissolved in a developing solution, which is preferable.

Moreover, to the above alkaline developing solution, alcohols such as methanol, ethanol and isopropyl alcohol and the above surfactant can also be added in an adequate amount. Among them, it is particularly preferable to add isopropyl alcohol in 10 to 30% by mass. Thereby, the wettability of a developing solution to a resist can be improved, which is preferable. In addition, when such a developing solution comprising an alkaline aqueous solution is used, washing with water is generally conducted after development.

After forming the resist pattern, a resist pattern wiring substrate is obtained by etching. Etching can be conducted by a publicly known method such as dry etching using plasma gas and wet etching with alkaline solution, cupric chloride solution, ferric chloride solution and the like.

After forming the resist pattern, plating can also be conducted. The above plating method is exemplified by copper plating, solder plating, nickel plating, gold plating and the like.

The remaining resist pattern after etching can be peeled by an organic solvent or an alkaline aqueous solution stronger than the alkaline aqueous solution used for development. The above organic solvent includes PGMEA (propylene glycol monomethyl ether acetate), PGME (propylene glycol monomethyl ether), EL (ethyl lactate) and the like, and the strong alkaline aqueous solution includes, for example, 1 to 20% by mass of sodium hydroxide aqueous solution and 1 to 20% by mass of potassium hydroxide aqueous solution. The above peeling method is exemplified by immersion method, spray method and the like. Moreover, a wiring substrate having a resist pattern formed may be a multilayer wiring substrate, and may have a small diameter through hole.

The wiring substrate obtained in the invention can also be formed by a method of forming a resist pattern then depositing a metal in vacuum, and subsequently dissolving the resist pattern in a solution, i.e., liftoff method.

EXAMPLES

Embodiments of the invention will be more particularly described with reference to examples below. However, the invention is not limited to these examples. In the following synthesis Examples and Examples, the structure of a compound is confirmed by $^1$H-NMR measurement and LC-MS measurement.

Synthesis 1

Synthesis of Cyclohexyloxyphenol

Under a nitrogen gas stream, resorcinol (55 g, 0.5 mol), potassium carbonate (207 g, 1.5 mol), water (25 ml, 1.4 mol) and N,N-dimethylformaldehyde (500 ml) were charged to a four necked flask (2 L) sufficiently dried, substituted with nitrogen, and equipped with a dropping funnel, Dimroth condenser tube, thermometer and stirring blade, so as to prepare a dimethylformaldehyde solution. Next, bromocylcohexane (408 g, 2.5 mol) was dropped through the dropping funnel for 10 minutes at room temperature, then this solution was heated at 80° C. for 14 hours by a mantle heater while stirring, and then heated at 100° C. for 11 hours. After the reaction terminated, it was stood to cool, and after it reached room temperature, it was cooled in an ice bath. The reaction solution was dissolved in 1 L toluene, and washed three times with 500 ml water. Toluen was distilled away by evaporation, and the residue was purified by column chromatography using hexane and ethyl acetate as developing solvents, to obtain a red brown objective product (hereinafter, referred to as R-1A) (21.9 g, 23% yield, 100% GC purity). The chemical shift value (δ ppm, TMS standard) of $^1$H-NMR of this compound in a heavy dimethyl sulfoxide solvent was 1.1 to 2.0 (m, 10H), 4.2 (m, H), 6.3 (m, 3H), 7.0 (m, H), 9.3 (s, H).

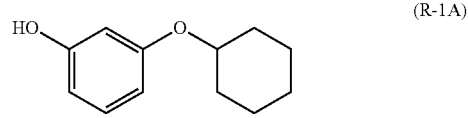 [SMILES: Oc1cccc(OC2CCCCC2)c1]

(R-1A)

Synthesis Example 1

Synthesis of Cyclic Compound (A)

Synthesis of CR-1A

Under a nitrogen gas stream, R-1A (5.38 g, 28 mmol) obtained in the above Synthesis 1, concentrated hydrochloric acid (35 wt %, 4.37 g) and ethanol (15 g) were charged to a four necked flask (100 mL) sufficiently dried, substituted with nitrogen, and equipped with a dropping funnel, Dimroth condenser tube, thermometer and stirring blade, so as to prepare an ethanol solution. Next, 4-hydroxybenzaldehyde (3.25 g, 27 mmol) made by Kanto Chemical and ethanol (8 g) were dropped through the dropping funnel for 10 minutes at room temperature, and then this solution was heated at 40° C. for 5 hours by a mantle heater while stirring. After the reaction terminated, it was stood to cool, and after it reached room temperature, it was cooled in an ice bath. Ethanol was distilled away by evaporation, and distilled water was added. A brown objective crude crystal was produced and separated. The crude crystal was washed six times with distilled water 100 ml, separated, and vacuum dried at 120° C. to obtain a red brown objective product (hereinafter, referred to as CR-1A) (8.3 g, 99% yield). (However, at least four kinds of stereoisomers are possible.)

The result of LC-MS analysis of the structure of this compound showed 1010 of the molecular weight of the objective substance. The chemical shift value (δ ppm, TMS standard) of $^1$H-NMR of this compound in a heavy dimethyl sulfoxide solvent was 1.0 to 1.8 (m, 40H), 4.0 (m, 4H), 5.5 (m, 4H), 6.0 to 6.5 (m, 24H), 8.5 to 8.7 (m, 8H).

(CR-1A)

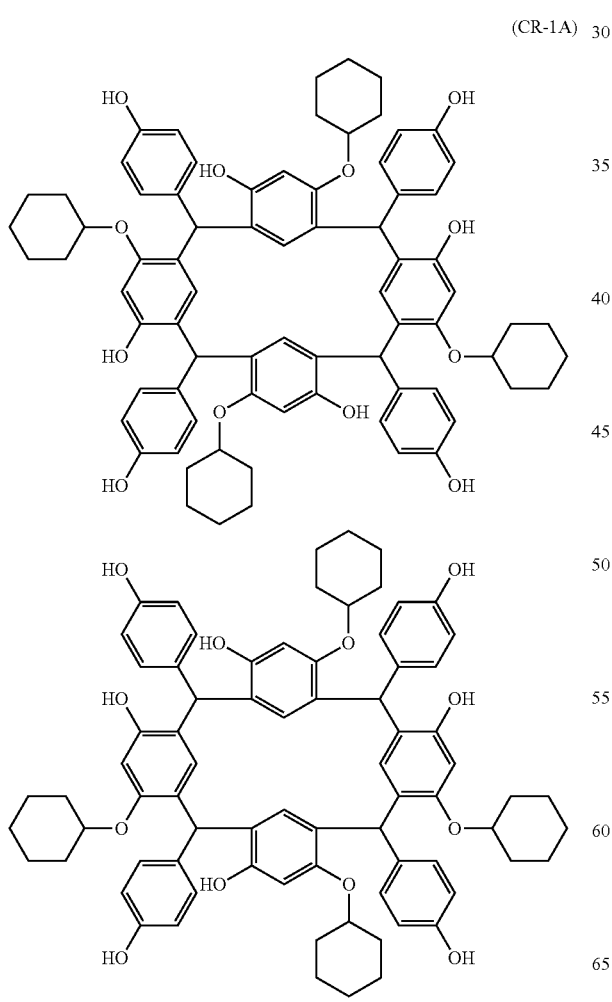

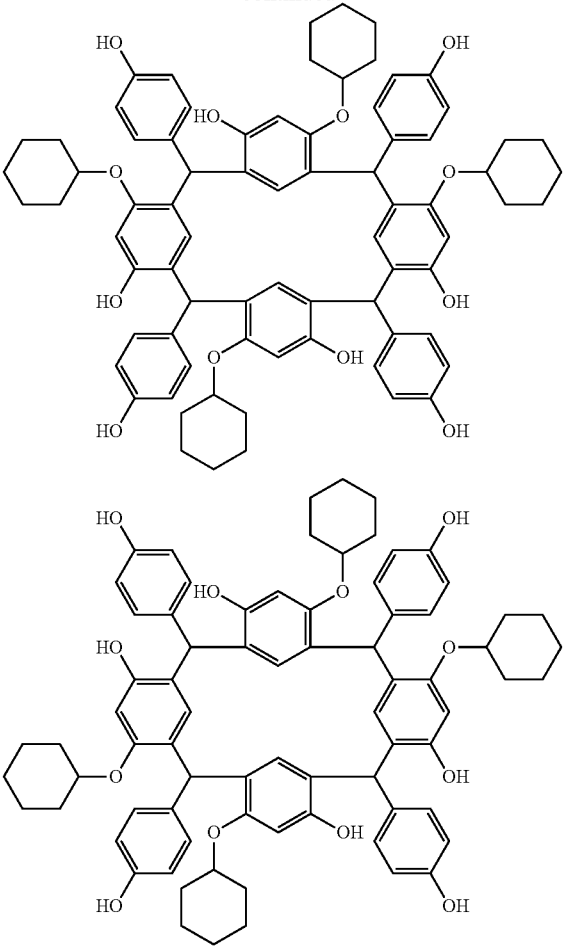

Synthesis Example 2

Synthesis of Cyclic Compound (A)

Synthesis of CR-2A

Under a nitrogen gas stream, R-1A (10.76 g, 56 mmol) obtained in the above Synthesis 1, concentrated hydrochloric acid (35 wt %, 8.74 g) and ethanol (40 g) were charged to a four necked flask (100 mL) sufficiently dried, substituted with nitrogen, and equipped with a dropping funnel, Dimroth condenser tube, thermometer and stirring blade, so as to prepare an ethanol solution. Next, 3,4-dihydroxybenzaldehyde (7.35 g, 54 mmol) made by Kanto Chemical and ethanol (7 g) were dropped through the dropping funnel for 10 minutes at room temperature, and then this solution was heated at 40° C. for 2 hours and at 60° C. for 5 hours by a mantle heater while stirring. After the reaction terminated, it was stood to cool, and after it reached room temperature, it was cooled in an ice bath. Ethanol was distilled away by evaporation, and distilled water was added. A red brown objective crude crystal was produced and separated. The crude crystal was washed six times with distilled water 100 ml, separated, and vacuum dried at 120° C. to obtain an objective product (hereinafter, referred to as CR-2A) (16.2 g, 97% yield). (However, at least four kinds of stereoisomers are possible.)

The result of LC-MS analysis of the structure of this compound showed 1071 of the molecular weight of the objective substance. The chemical shift value (δ ppm, TMS standard) of ¹H-NMR of this compound in a heavy dimethyl sulfoxide solvent was 1.0 to 1.8 (m, 40H), 4.0 (m, 4H), 5.4 (m, 4H), 5.9 to 6.4 (m, 20H), 8.5 (m, 12H).

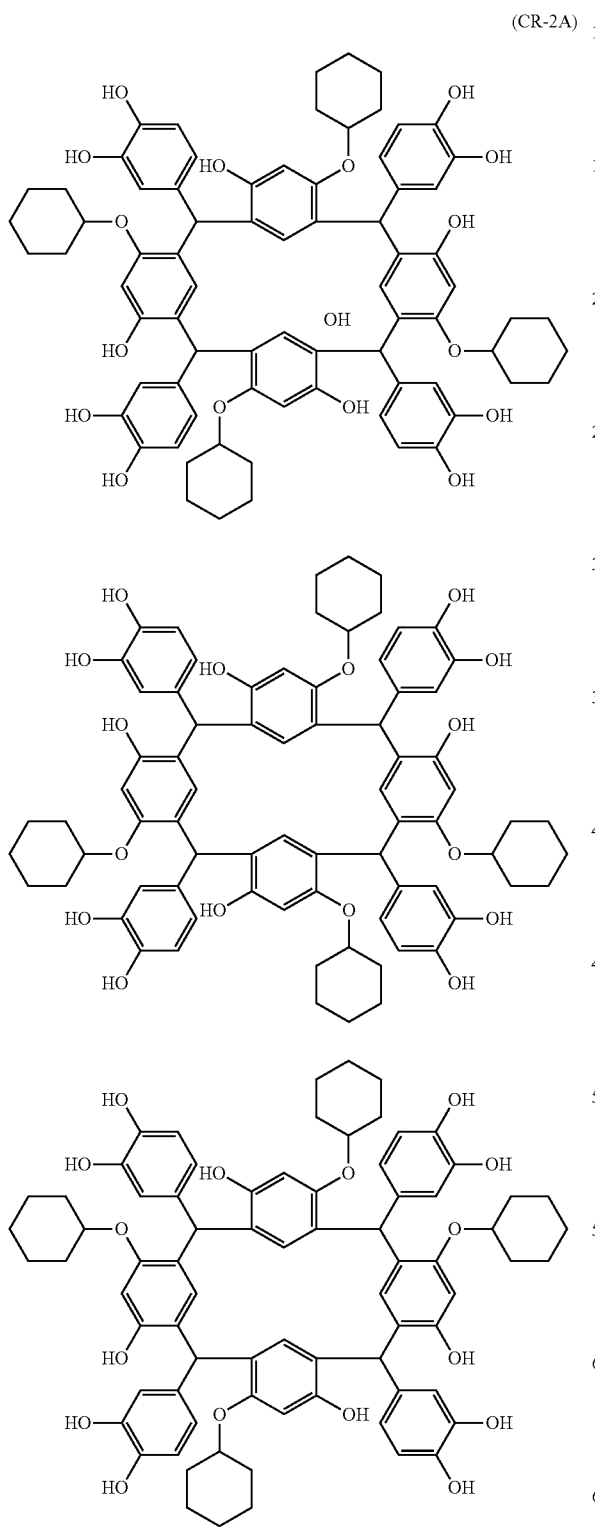

(CR-2A)

Synthesis 2

Synthesis of 3-(4-methylcyclohexyloxy)phenol

In a four necked flask (2 L) sufficiently dried, substituted with nitrogen, and equipped with a dropping funnel, Dimroth condenser tube, thermometer and stirring blade, resorcinol (110 g, 1.0 mol), 4-methylcyclohexanol (114 g, 1.0 mol) and triphenylphosphine (393 g, 1.5 mol) were dissolved in dried tetrahydrofuran (500 ml) under a nitrogen gas stream, and a mixed solution of diisopropyl azodicarboxylate (269 g, 1.3 mol) and dried tetrahydrofuran (400 ml) was dropped for 1 hour while cooling with iced saline solution. Next, it was stirred at room temperature for 12 hours. After the reaction terminated, 30% hydrogen peroxide (200 ml) was dropped through the dropping funnel for 10 minutes, then the reaction solution was dissolved in 2 L toluene, and washed three times with 1 L water. Toluene was distilled away by evaporation, and the residue was purified by column chromatography using hexane and ethyl acetate as developing solvents, to obtain a red brown objective product (hereinafter, referred to as R-2A) (45.0 g, 22% yield, 97% GC purity).

The chemical shift value (δ ppm, TMS standard) of ¹H-NMR of this compound in a heavy dimethyl sulfoxide solvent was 0.9 (m, 3H), 1.0 to 1.8 (m, 8H), 2.0 (m, H), 4.0 (m, H), 6.3 (m, 3H), 7.0 (m, H), 9.3 (b, H).

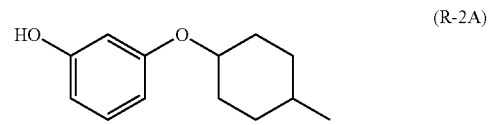

(R-2A)

Synthesis Example 3

Synthesis of Cyclic Compound (A)

Synthesis of CR-3A

Under a nitrogen gas stream, R-2A (11.53 g, 56 mmol) obtained in the above Synthesis 2, concentrated hydrochloric acid (35 wt %, 8.73 g) and ethanol (40 g) were charged to a four necked flask (100 mL) sufficiently dried, substituted with nitrogen, and equipped with a dropping funnel, Dimroth condenser tube, thermometer and stirring blade, so as to prepare an ethanol solution. Next, 4-hydroxybenzaldehyde (6.50 g, 53 mmol) made by Kanto Chemical and ethanol (7 g) were dropped through the dropping funnel for 10 minutes at room temperature, then this solution was heated at 40° C. for 5 hours by a mantle heater while stirring. After the reaction terminated, it was stood to cool, and after it reached room temperature, it was cooled in an ice bath. Ethanol was distilled away by evaporation, and distilled water was added. A brown objective crude crystal was produced and separated. The crude crystal was washed six times with distilled water 100 ml, separated, and vacuum dried at 120° C. to obtain a red purple objective product (hereinafter, referred to as CR-3A) (15.6 g, 94% yield). (However, at least four kinds of stereoisomers are possible.)

The result of LC-MS analysis of the structure of this compound showed 1085 of the molecular weight of the objective substance. The chemical shift value (8 ppm, TMS standard) of $^1$H-NMR of this compound in a heavy dimethyl sulfoxide solvent was 1.0 to 1.6 (m, 48H), 3.2 to 3.4 (m, 4H), 5.5 (m, 4H), 6.2 to 6.5 (m, 24H), 8.5 to 8.7 (m, 8H).

(CR-3A)

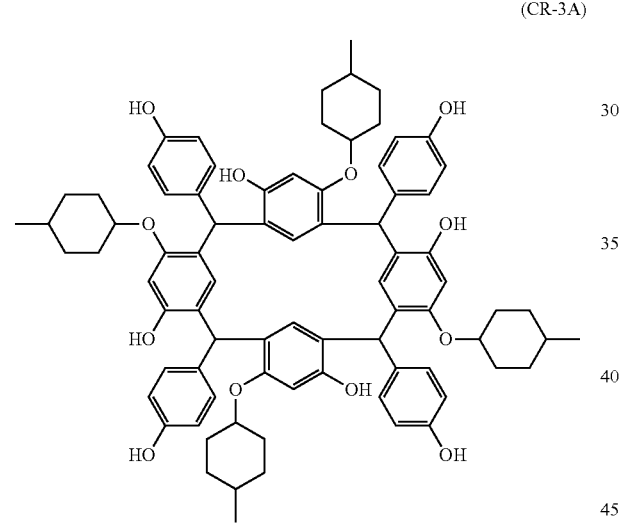

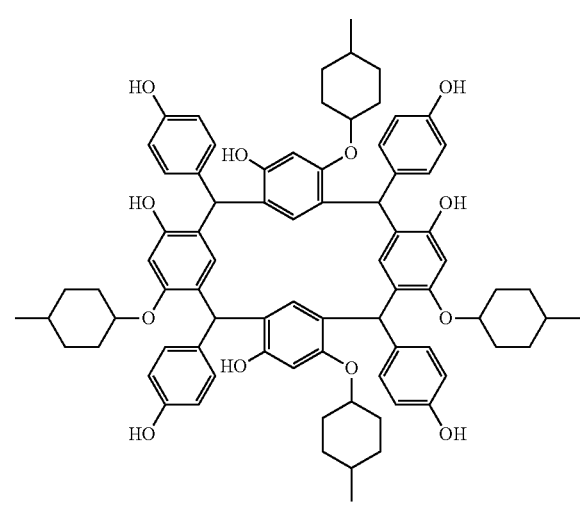

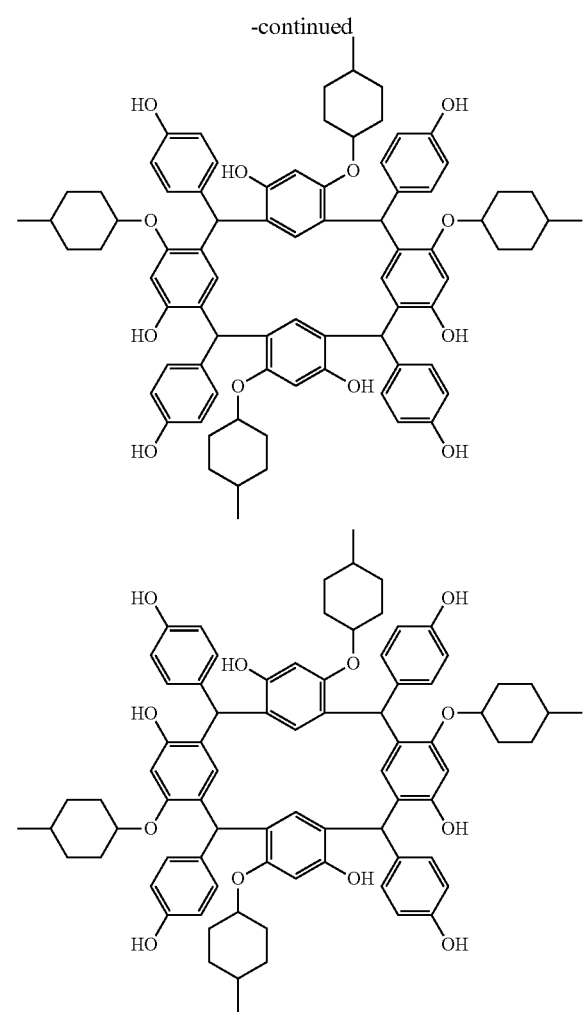

Synthesis Example 4

Synthesis of CR-4A

Under a nitrogen gas stream, R-2A (11.54 g, 56 mmol) obtained in the above Synthesis 2, concentrated hydrochloric acid (35 wt %, 8.73 g) and ethanol (45 g) were charged to a four necked flask (100 mL) sufficiently dried, substituted with nitrogen, and equipped with a dropping funnel, Dimroth condenser tube, thermometer and stirring blade, so as to prepare an ethanol solution. Next, 3,4-dihydroxybenzaldehyde (7.35 g, 53 mmol) made by Kanto Chemical and ethanol (4 g) were dropped through the dropping funnel for 10 minutes at room temperature, and then this solution was heated at 40° C. for 5 hours by a mantle heater while stirring. After the reaction terminated, it was stood to cool, and after it reached room temperature, it was cooled in an ice bath. Ethanol was distilled away by evaporation, and distilled water was added. A brown objective crude crystal was produced and separated. The crude crystal was washed six times with distilled water 100 ml, separated, and vacuum dried at 120° C. to obtain a red purple objective product (hereinafter, referred to as CR-4A) (16.6 g, 96% yield). (However, at least four kinds of stereoisomers are possible.)

The result of LC-MS analysis of the structure of this compound showed 1085 of the molecular weight of the objective substance. The chemical shift value (δppm, TMS standard) of ¹H-NMR of this compound in a heavy dimethyl sulfoxide solvent was 0.7 to 2.1 (m, 48H), 3.1 to 3.4 (m, 4H), 5.4 (m, 4H), 6.2 to 6.4 (m, 20H), 8.0 to 8.5 (m, 12H).

(CR-4A)

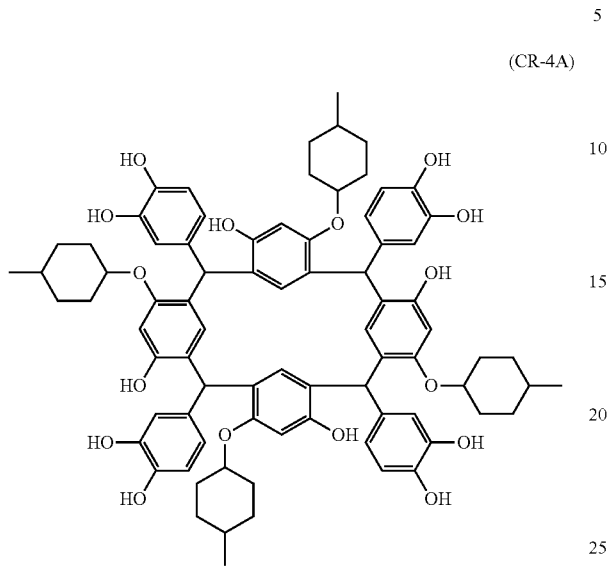

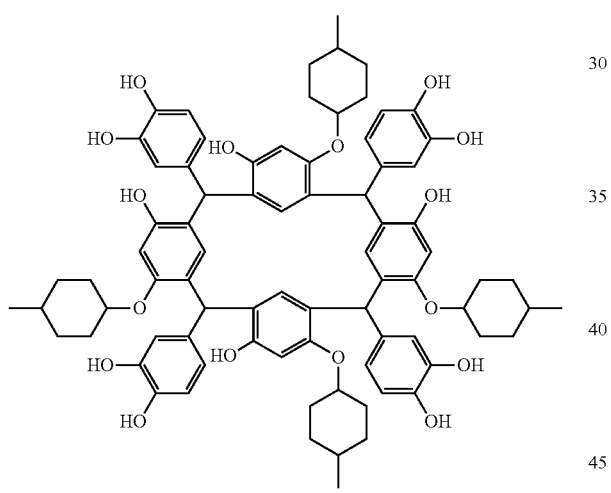

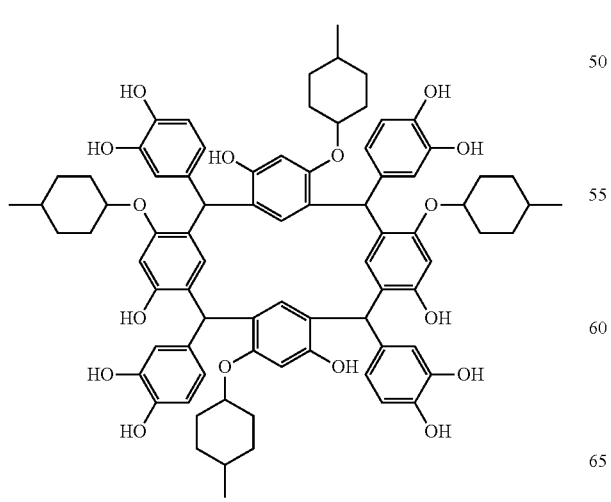

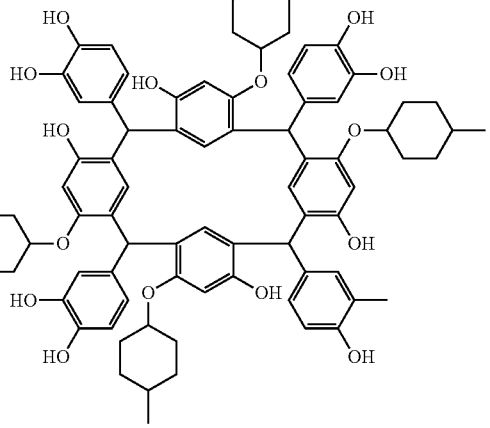

Synthesis 3

Synthesis of 3-(4-ethylcyclohexyloxy)phenol

In a four necked flask (2 L) sufficiently dried, substituted with nitrogen, and equipped with a dropping funnel, Dimroth condenser tube, thermometer and stirring blade, resorcinol (72 g, 0.65 mol), 4-ethylcyclohexanol (92 g, 0.72 mol) and triphenylphosphine (185 g, 0.70 mol) were dissolved in dried tetrahydrofuran (700 ml) under a nitrogen gas stream, and a mixed solution of diisopropyl azodicarboxylate (132 g, 0.65 mol) and dried tetrahydrofuran (180 ml) was dropped for 1 hour while cooling with an iced saline solution. Next, it was stirred at room temperature for 12 hours. After the reaction terminated, 30% hydrogen peroxide (140 ml) was dropped through the dropping funnel for 10 minutes, then the reaction solution was dissolved in 1 L toluene, and washed three times with 500 ml water. Toluene was distilled away by evaporation, and the residue was purified by column chromatography using hexane and ethyl acetate as developing solvents, to obtain a red brown objective product (hereinafter, referred to as R-3A) (38.5 g, 27% yield, 99% GC purity).

The chemical shift value (δ ppm, TMS standard) of ¹H-NMR of this compound in a heavy dimethyl sulfoxide solvent was 0.8 (m, 5H), 1.0 to 1.9 (m, 9H), 4.0 (m, H), 6.5 (m, 3H), 7.0 (m, H), 8.9 (b, H).

(R-3A)

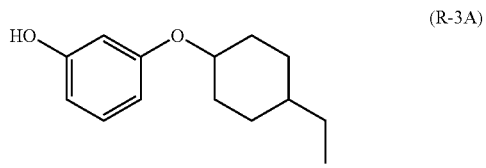 [SMILES: CCC1CCC(Oc2cccc(O)c2)CC1]

Synthesis Example 5

Synthesis of Cyclic Compound (A)

Synthesis of CR-5A

Under a nitrogen gas stream, R-3A (9.17 g, 28 mmol) obtained in the above Synthesis 3, concentrated hydrochloric acid (35 wt %, 4.37 g) and ethanol (20 g) were charged to a four necked flask (100 mL) sufficiently dried, substituted with nitrogen, and equipped with a dropping funnel, Dimroth condenser tube, thermometer and stirring blade, so as to prepare an ethanol solution. Next, 4-hydroxybenzaldehyde (3.25 g, 27 mmol) made by Kanto Chemical and ethanol (4 g) were dropped through the dropping funnel for 10 minutes at room temperature, and then this solution was heated at 40° C. for 5 hours by a mantle heater while stirring. After the reaction terminated, it was stood to cool, and after it reached room temperature, it was cooled in an ice bath. Ethanol was distilled away by evaporation, and distilled water was added. A brown objective crude crystal was produced and separated. The crude crystal was washed six times with distilled water 100 ml, separated, and vacuum dried at 120° C. to obtain a red purple objective product (hereinafter, referred to as CR-5A) (7.9 g, 91% yield). (However, at least four kinds of stereoisomers are possible.)

The result of LC-MS analysis of the structure of this compound showed 1124 of the molecular weight of the objective substance. The chemical shift value (6 ppm, TMS standard) of $^1$H-NMR of this compound in a heavy dimethyl sulfoxide solvent was 1.0 to 1.6 (m, 56H), 3.2 to 3.8 (m, 4H), 4.9 (m, 4H), 5.8 to 6.1 (m, 24H), 8.0 to 8.2 (m, 8H).

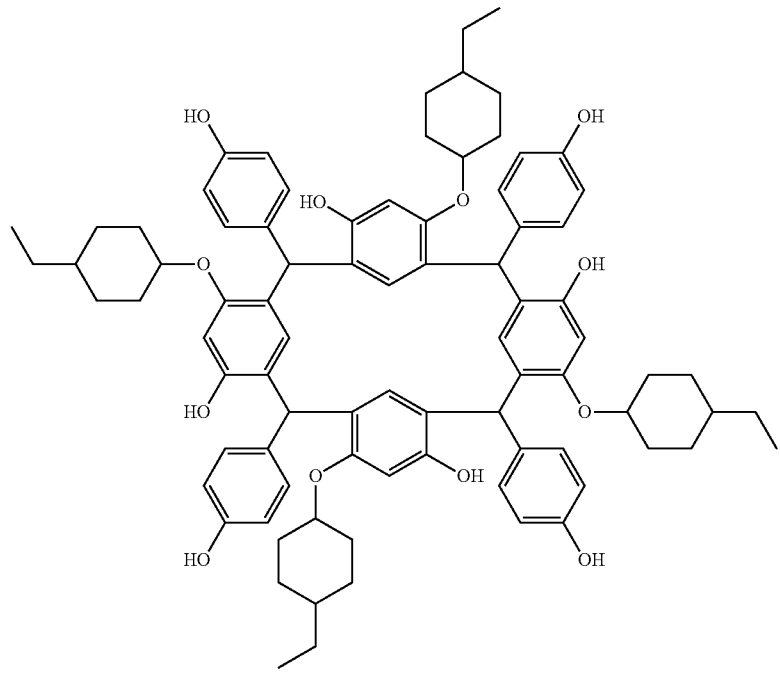

(CR-5A)

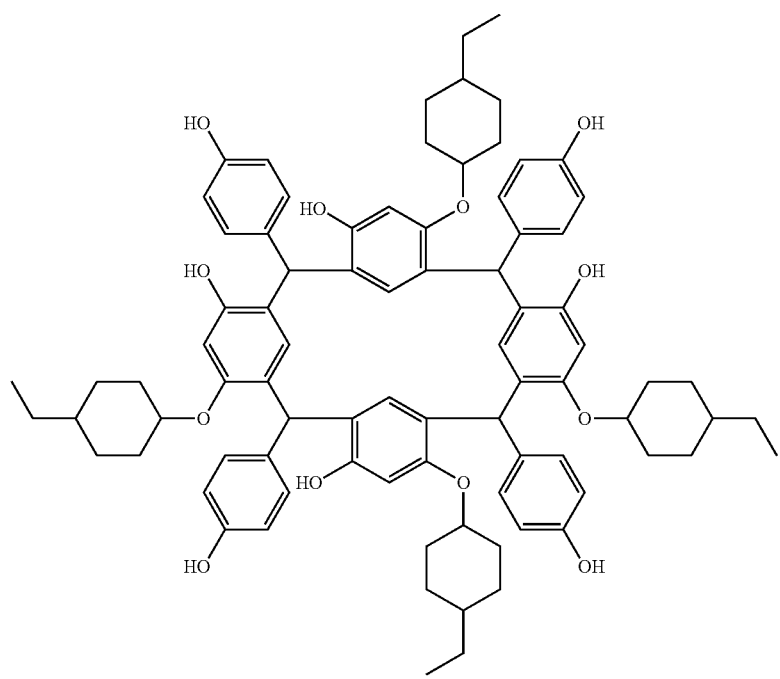

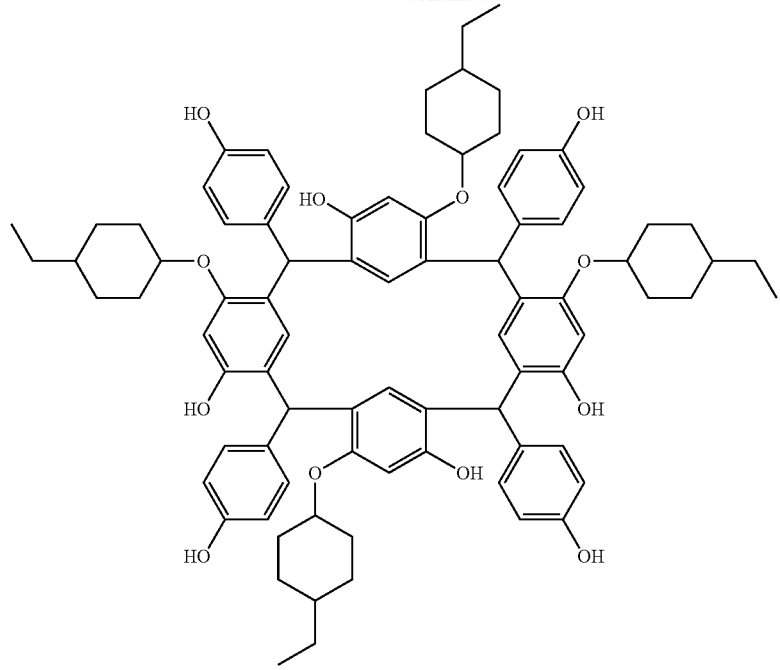

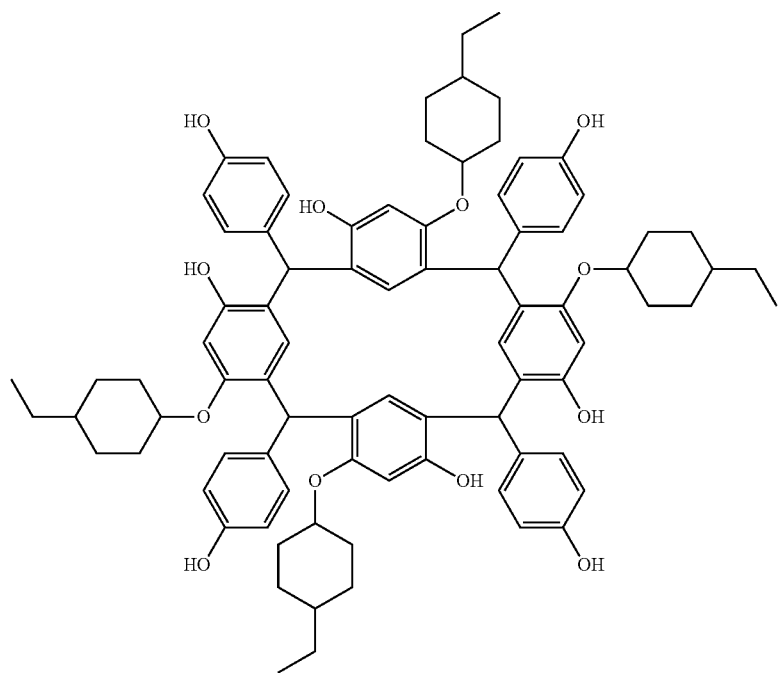

Synthesis Example 6

Synthesis of Cyclic Compound (A)

Synthesis of CR-6A

Under a nitrogen gas stream, R-3A (6.16 g, 28 mmol) obtained in the above Synthesis 3, concentrated hydrochloric acid (35 wt %, 4.38 g) and ethanol (15 g) were charged to a four necked flask (100 mL) sufficiently dried, substituted with nitrogen, and equipped with a dropping funnel, Dimroth condenser tube, thermometer and stirring blade, so as to prepare an ethanol solution. Next, 3,4-dihydroxybenzaldehyde (3.68 g, 27 mmol) made by Kanto Chemical and ethanol (8 g) were dropped through the dropping funnel for 10 minutes at room temperature, and then this solution was heated at 40° C.

for 5 hours by a mantle heater while stirring. After the reaction terminated, it was stood to cool, and after it reached room temperature, it was cooled in an ice bath. Ethanol was distilled away by evaporation, and distilled water was added. A brown objective crude crystal was produced and separated. The crude crystal was washed six times with distilled water 100 ml, separated, and vacuum dried at 120° C. to obtain a red purple objective product (hereinafter, referred to as CR-6A) (8.3 g, 92% yield). (However, at least four kinds of stereoisomers are possible.)

The result of LC-MS analysis of the structure of this compound showed 1198 of the molecular weight of the objective substance. The chemical shift value (δ ppm, TMS standard) of $^1$H-NMR of this compound in a heavy dimethyl sulfoxide solvent was 0.7 to 1.8 (m, 56H), 4.1 to 4.2 (m, 4H), 5.8 (m, 4H), 6.1 to 6.4 (m, 20H), 8.0 to 8.5 (m, 12H).

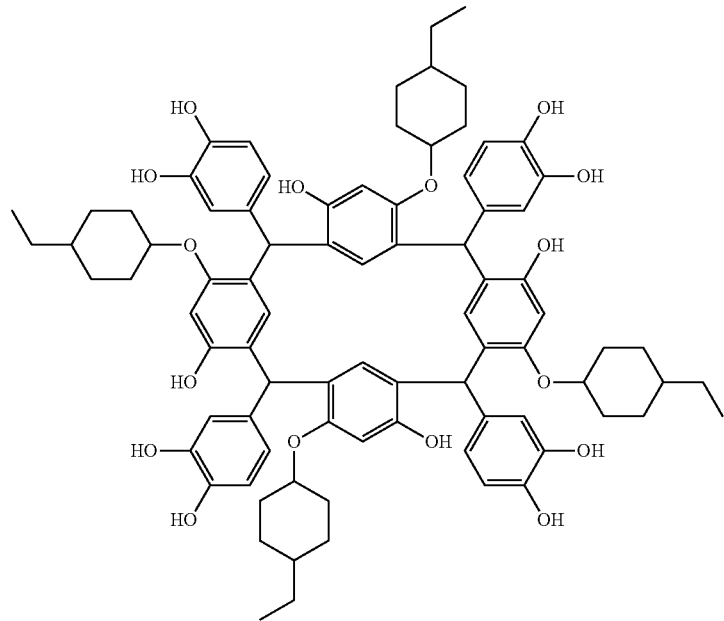

(CR-6A)

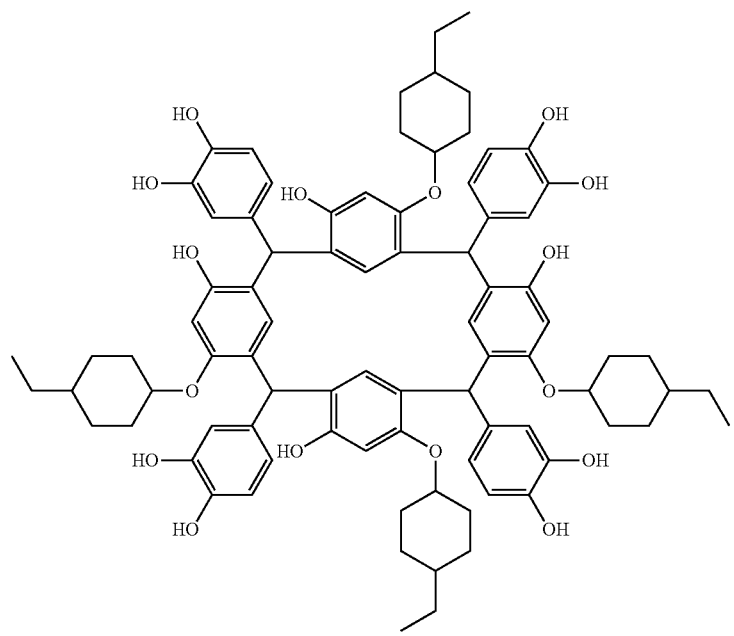

-continued

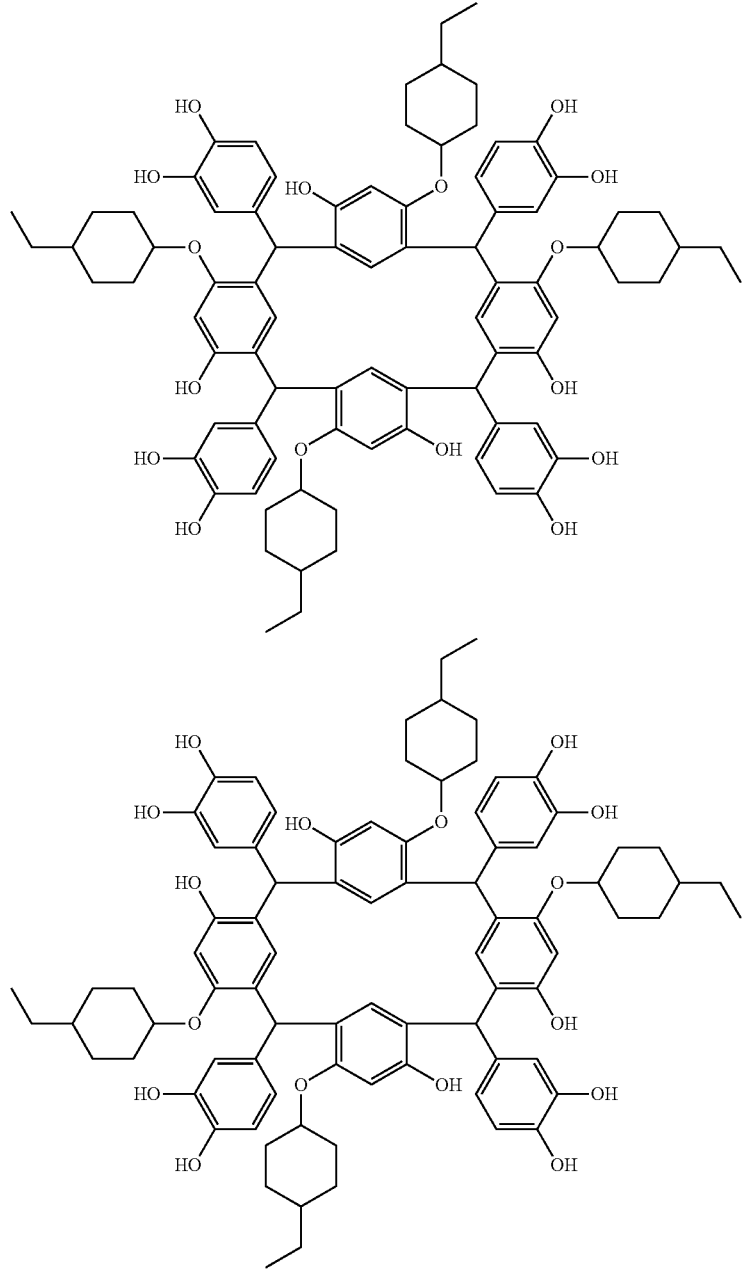

Synthesis 4

Synthesis of 3-(3,3,5-trimethylcyclohexyloxy)phenol

In a four necked flask (1 L) sufficiently dried, substituted with nitrogen, and equipped with a dropping funnel, Dimroth condenser tube, thermometer and stirring blade, resorcinol (42 g, 0.38 mol), 3,3,5-trimethylcyclohexanol (54 g, 0.57 mol) and triphenylphosphine (150 g, 0.57 mol) were dissolved in dried tetrahydrofuran (200 ml) under a nitrogen gas stream, and a mixed solution of diisopropyl azodicarboxylate (100 g, 0.5 mol) and dried tetrahydrofuran (150 ml) was dropped for 1 hour while cooling with an iced saline solution.

Next, it was stirred at room temperature for 12 hours. After the reaction terminated, 30% hydrogen peroxide (75 ml) was dropped through the dropping funnel for 10 minutes, then the reaction solution was dissolved in 1 L toluene, and washed three times with 500 ml water. Toluene was distilled away by evaporation, and the residue was purified by column chromatography using hexane and ethyl acetate as developing solvents, to obtain a red brown objective product (hereinafter, referred to as R-4A) (19.5 g, 22% yield, 99% GC purity).

The chemical shift value ($\delta$ ppm, TMS standard) of $^1$H-NMR of this compound in a heavy dimethyl sulfoxide solvent was 0.7 (m, 1H), 0.9 to 1.0 (m, 9H), 1.2 to 2.0 (m, 6H), 4.1 (m, H), 6.5 (m, 3H), 7.0 (m, H), 8.9 (b, H).

(R-4A)

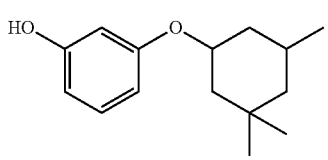

Synthesis Example 7

Synthesis of Cyclic Compound (A)

Synthesis of CR-7A

Under a nitrogen gas stream, R-4A (6.55 g, 28 mmol) obtained in the above Synthesis 4, concentrated hydrochloric acid (35 wt %, 4.37 g) and ethanol (21 g) were charged to a four necked flask (100 mL) sufficiently dried, substituted with nitrogen, and equipped with a dropping funnel, Dimroth condenser tube, thermometer and stirring blade, so as to prepare an ethanol solution. Next, 3,4-dihydroxybenzaldehyde (3.67 g, 27 mmol) made by Kanto Chemical and ethanol (3 g) were dropped through the dropping funnel for 10 minutes at room temperature, and then this solution was heated at 40° C. for 5 hours by a mantle heater while stirring. After the reaction terminated, it was stood to cool, and after it reached the room temperature, it was cooled in an ice bath. Ethanol was distilled away by evaporation, and distilled water was added. A brown objective crude crystal was produced and separated. The crude crystal was washed six times with distilled water 100 ml, separated, and vacuum dried at 120° C. to obtain a red purple objective product (hereinafter, referred to as CR-7A) (8.6 g, 99% yield). (However, at least four kinds of stereoisomers are possible.)

The result of LC-MS analysis of the structure of this compound showed 1254 of the molecular weight of the objective substance. The chemical shift value ($\delta$ ppm, TMS standard) of $^1$H-NMR of this compound in a heavy dimethyl sulfoxide solvent was 0.5 to 2.0 (m, 64H), 4.1 to 4.3 (m, 4H), 5.4 (m, 4H), 6.0 to 6.4 (m, 20H), 7.8 to 8.4 (m, 12H).

(CR-7A)

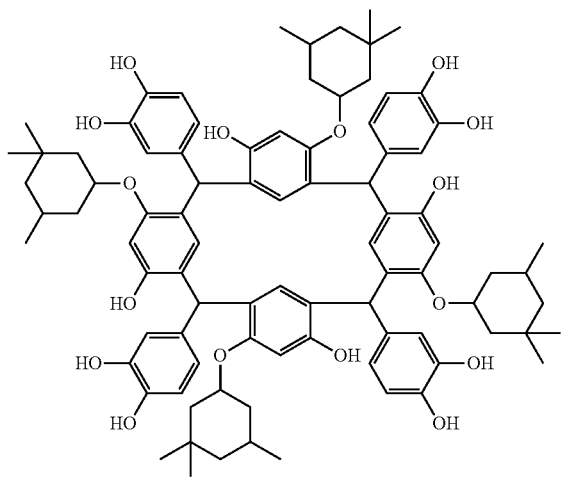

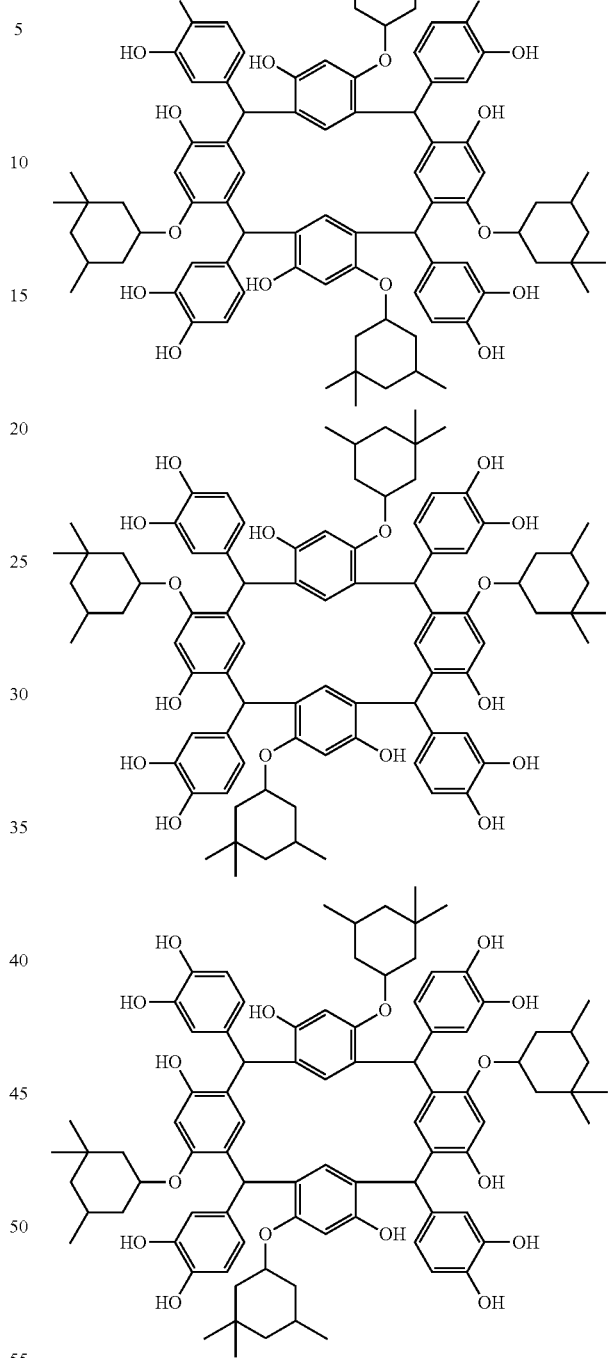

Synthesis Comparative Example 1

Synthesis of Cyclic Compound (A)

Synthesis of CR-8A

Under a nitrogen gas stream, 3-methoxyphenol (6.9 g, 57 mmol) made by Kanto Chemical, concentrated hydrochloric acid (35 wt %, 8.74 g) and ethanol (40 g) were charged to a four necked flask (100 mL) sufficiently dried, substituted with nitrogen, and equipped with a dropping funnel, Dimroth condenser tube, thermometer and stirring blade, so as to prepare an ethanol solution. Next, 2,4-dimethylbenzaldehyde (7.1 g, 53 mmol) made by Mitsubishi Gas Chemical and ethanol (7 g) were dropped through the dropping funnel for 10 minutes at room temperature, and then this solution was heated at 40° C. for 1 hour and at 60° C. for 5 hours by a mantle heater while stirring. After the reaction terminated, it was stood to cool, and after it reached room temperature, it was cooled in an ice bath. Ethanol was distilled away by evaporation, and distilled water was added. A yellow objective crude crystal was produced and separated. The crude crystal was washed six times with distilled water 100 ml, separated, and vacuum dried at 120° C. to obtain a red purple objective product (hereinafter, referred to as CR-8A) (12.6 g, 98% yield). (However, at least four kinds of stereoisomers are possible.)

The result of LC-MS analysis of the structure of this compound showed 1069 of the molecular weight of the objective substance. The chemical shift value (δ ppm, TMS standard) of $^1$H-NMR of this compound in a heavy dimethyl sulfoxide solvent was 1.2 to 2.3 (m, 24H), 2.9 to 3.2 (m, 12H), 5.2 to 5.6 (m, 4H), 6.0 to 6.8 (m, 20H), 8.6 to 9.1 (m, 4H).

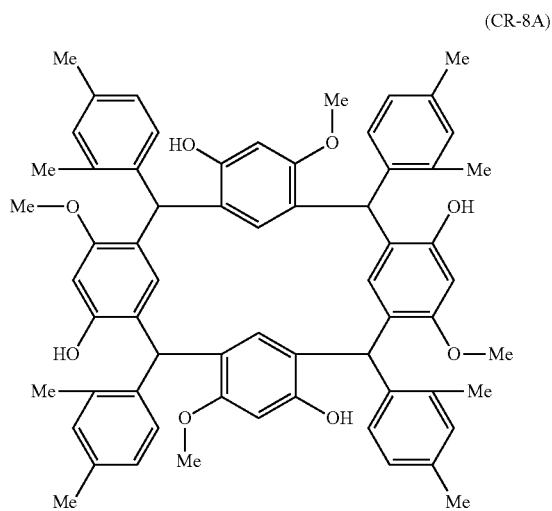

(CR-8A)

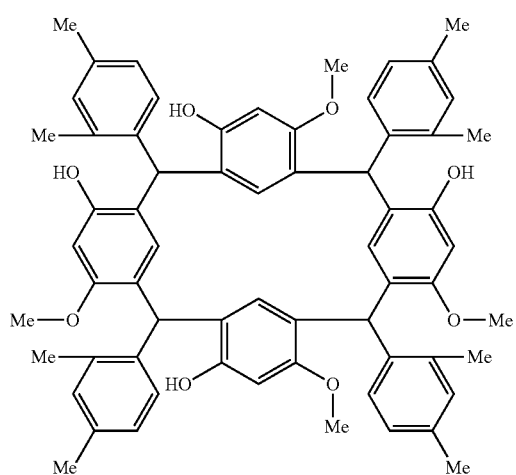 [SMILES: COc1cc(O)c2cc1C(c1ccc(C)cc1C)c1cc(c(O)cc1OC)C(c1ccc(C)cc1C)c1cc(c(OC)cc1O)C(c1ccc(C)cc1C)c1cc(c(O)cc1OC)C2c1ccc(C)cc1C]

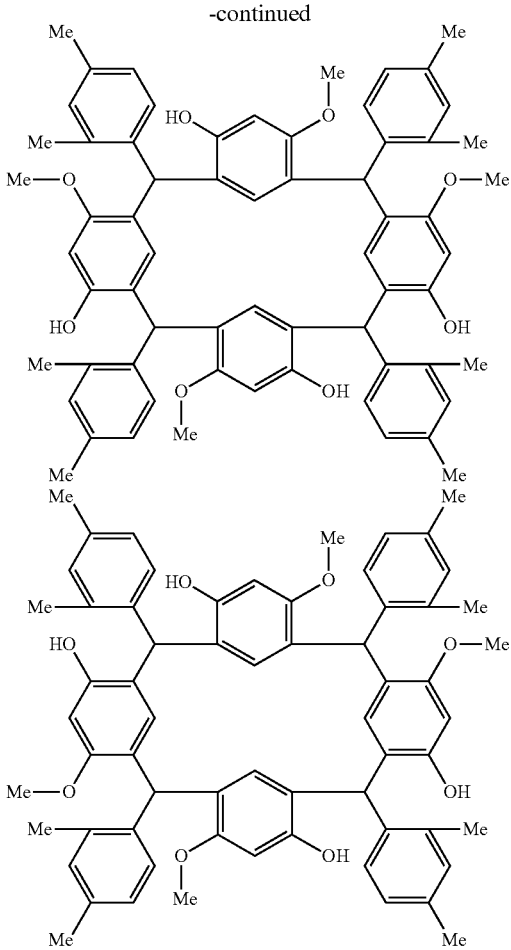

Synthesis Comparative Example 2

Synthesis of Cyclic Compound (A)

Synthesis of CR-9A

Under a nitrogen gas stream, 3-ethoxyphenol (13.8 g, 0.1 mol) made by Kanto Chemical, p-anisbenzaldehyde (13.6 g, 0.1 mol) and ethanol (200 g) were charged to a four necked flask (1 L) sufficiently dried, substituted with nitrogen, and equipped with a dropping funnel, Dimroth condenser tube, thermometer and stirring blade, so as to prepare an ethanol solution. Next, concentrated hydrochloric acid (35 wt %, 25 ml) was dropped through the dropping funnel for 10 minutes at room temperature, and then this solution was heated at 70° C. for 12 hours by a mantle heater while stirring. After the reaction terminated, it was stood to cool, and after it reached room temperature, it was cooled in an ice bath. Ethanol was distilled away by evaporation, and distilled water was added. A yellow objective crude crystal was produced and separated. The crude crystal was washed six times with distilled water 100 ml, separated, and vacuum dried at 120° C. to obtain a red purple objective product (hereinafter, referred to as CR-9A) (25.1 g, 98% yield). (However, at least four kinds of stereoisomers are possible.)

The result of LC-MS analysis of the structure of this compound showed 757 of the molecular weight of the objective substance. The chemical shift value (δ ppm, TMS standard) of $^1$H-NMR of this compound in a heavy dimethyl sulfoxide solvent was 1.0 to 1.2 (m, 12H), 3.5 to 4.0 (m, 20H), 5.5 (m, 4H), 6.2 to 6.6 (m, 24H), 8.6 to 8.7 (m, 4H).

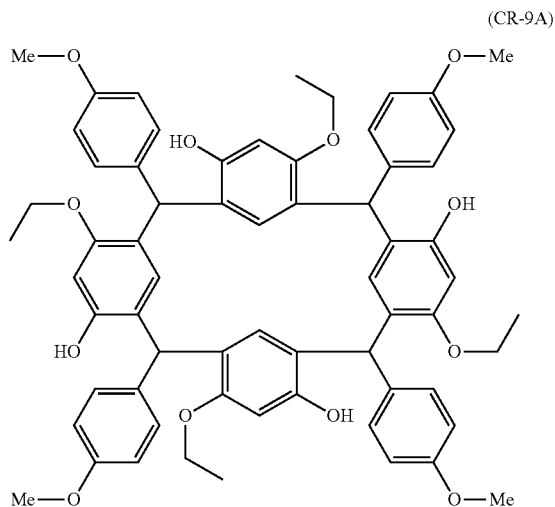

(CR-9A)

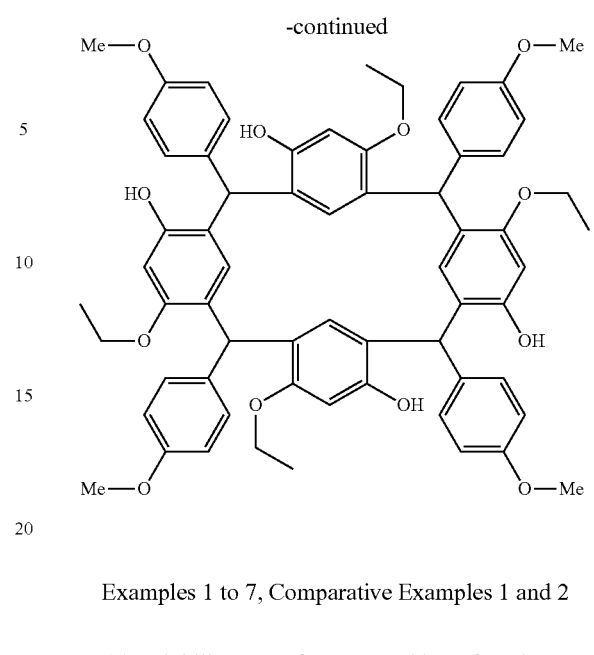

Examples 1 to 7, Comparative Examples 1 and 2

(1) Solubility Test of Compound in Safe Solvent

The dissolution amount of compounds obtained in the above Synthesis Examples 1 to 7 and Synthesis Comparative Examples 1 and 2 in propylene glycol monomethyl ether (PGME) and cyclohexanone (CHN) were evaluated. The result is shown in Table 1.

A: 5.0 wt %≤dissolution amount

B: 3.0 wt %≤dissolution amount<5.0 wt %

C: dissolution amount<3.0 wt %

TABLE 1

|  | Compound | PGME | CHN |
|---|---|---|---|
| Example 1 | CR-1A | A | A |
| Example 2 | CR-2A | A | A |
| Example 3 | CR-3A | A | A |
| Example 4 | CR-4A | A | A |
| Example 5 | CR-5A | A | A |
| Example 6 | CR-6A | A | A |
| Example 7 | CR-7A | A | A |
| Comparative Example 1 | CR-8A | C | C |
| Comparative Example 2 | CR-9A | C | C |

From the result of Table 1, it was clear that the compounds obtained in Examples 1 to 7 show better results of larger dissolution amounts in propylene glycol monomethyl ether (PGME) and cyclohexahone (CHN), as compared to the compounds obtained in Comparative Examples 1 and 2.

Examples 8 to 24, Comparative Examples 3 and 4

(2) Patterning Test

Components described in Table 2 were blended into homogeneous solutions, and then filtered through a membrane filter made of Teflon (registered trademark) with a pore diameter of 0.1 μm to prepare radiation-sensitive compositions, and the following evaluations were conducted for each. The result is shown in Table 3.

TABLE 2

| | Compound | (C) Acid generating agent (g) | (G) Acid crosslinking agent (g) | (E) Acid diffusion controlling agent (g) | Solvent (g) |
|---|---|---|---|---|---|
| Example 8 | CR-1A 0.4 | P-1 0.1 | C-1 0.1 | Q-1 0.045 | S-1 24.4 |
| Example 9 | CR-1A 0.4 | P-2 0.1 | C-1 0.1 | Q-2 0.015 | S-1 21.4 |
| Example 10 | CR-1A 0.4 | P-3 0.1 | C-1 0.1 | Q-1 0.015 | S-1 21.4 |
| Example 11 | CR-1A 0.4 | P-4 0.1 | C-1 0.1 | Q-2 0.015 | S-1 21.4 |
| Example 12 | CR-1A 0.4 | P-5 0.1 | C-1 0.1 | Q-1 0.015 | S-1 21.4 |
| Example 13 | CR-1A 0.4 | P-6 0.1 | C-1 0.1 | Q-2 0.015 | S-1 21.4 |
| Example 14 | CR-2A 0.4 | P-1 0.1 | C-1 0.1 | Q-2 0.015 | S-1 21.4 |
| Example 15 | CR-3A 0.4 | P-2 0.15 | C-1 0.1 | Q-1 0.030 | S-1 22.6 |
| Example 16 | CR-3A 0.4 | P-3 0.15 | C-1 0.1 | Q-1 0.030 | S-1 22.6 |
| Example 17 | CR-3A 0.4 | P-4 0.1 | C-1 0.1 | Q-1 0.015 | S-1 21.4 |
| Example 18 | CR-4A 0.4 | P-1 0.1 | C-1 0.1 | Q-1 0.015 | S-1 21.4 |
| Example 19 | CR-5A 0.4 | P-3 0.15 | C-1 0.1 | Q-1 0.030 | S-1 22.6 |
| Example 20 | CR-6A 0.4 | P-1 0.1 | C-1 0.1 | Q-1 0.015 | S-1 21.4 |
| Example 21 | CR-6A 0.4 | P-3 0.15 | C-1 0.1 | Q-1 0.030 | S-1 22.6 |
| Example 22 | CR-7A 0.4 | P-2 0.15 | C-1 0.1 | Q-1 0.030 | S-1 22.6 |
| Example 23 | CR-7A 0.4 | P-3 0.15 | C-1 0.1 | Q-1 0.030 | S-1 22.6 |
| Example 24 | CR-7A 0.4 | P-4 0.15 | C-1 0.1 | Q-1 0.030 | S-1 22.6 |
| Comparative Example 3 | CR-8A 0.4 | P-1 0.1 | C-1 0.1 | Q-1 0.015 | S-1 21.4 |
| Comparative Example 4 | CR-9A 0.4 | P-1 0.1 | C-1 0.1 | Q-1 0.015 | S-1 21.4 |

(C) Acid Generating Agent
P-1: Triphenylsulfonium trifluoromethanesulfonate (Midori Kagaku Co., Ltd.)
P-2: Triphenylsulfonium 1-butanesulfonate (Wako Pure Chemical Industries, Ltd.)
P-3: Triphenylsulfonium paratoluenesulfonate (Wako Pure Chemical Industries, Ltd.)
P-4: Diphenyl-2,4,6-phenylsulfonium paratoluenesulfonate (Wako Pure Chemical Industries, Ltd.)
P-5: Diphenyliodonium trifluoromethanesulfonate (Midori Kagaku Co., Ltd.)
P-6: Diphenyliodonium paratoluenesulfonate (Midori Kagaku Co., Ltd.)
(G) Acid Crosslinking Agent
C-1: NIKALAC MW-100LM (Sanwa Chemical Co., Ltd.)
(E) Acid Diffusion Controlling Agent
Q-1: Trioctylamine (Tokyo Chemical Industry Co., Ltd.)
Q-2: Rofin (Tokyo Chemical Industry Co., Ltd.)
Solvent
S-1: Propylene glycol monomethyl ether (Tokyo Chemical Industry Co., Ltd.)

(2-1) Evaluation of Resolution

A resist was spin coated on a clean silicon wafer, and then prebaked (PB) before exposure in an oven to form a resist film with a thickness of 60 nm. The resist film was irradiated with electron beams of 1:1 line and space setting with a 50 nm interval and a 30 nm interval using an electron beam lithography system (ELS-7500, made by ELIONIX INC.). After irradiation, it was heated at each predetermined temperature for 90 seconds, and developed in 2.38% by weight TMAH aqueous solution for 60 seconds. Subsequently, it was washed with water for 30 seconds, and dried to form a negative type resist pattern. The obtained line and space was observed by a scanning electron microscope (S-4800 made by Hitachi High-Technologies Corporation). In addition, the dose amount ($\mu C/cm^2$) in this regard was sensitivity.

(2-2) Evaluation of Pattern Shape

Cross section photos of the obtained 1:1 line and space with a 50 nm interval and a 30 nm interval were observed by a scanning electron microscope (S-4800 made by Hitachi-Technologies Corporation) and evaluated.

A: Rectangular pattern without pattern collapse (good pattern)
B: Substantially rectangular pattern with pattern collapse (substantially good pattern)
C: Random pattern or pattern peeling (bad pattern)

TABLE 3

| | PEB (° C.) | Sensitivity ($\mu C/cm^2$) | 50 nm interval Pattern shape | 30 nm interval Pattern shape |
|---|---|---|---|---|
| Example 8 | 110 | 102.0 | A | A |
| Example 9 | 110 | 110.0 | A | A |

TABLE 3-continued

| | PEB (°C.) | Sensitivity (μC/cm²) | 50 nm interval Pattern shape | 30 nm interval Pattern shape |
|---|---|---|---|---|
| Example 10 | 110 | 150.0 | A | A |
| Example 11 | 110 | 100.0 | A | A |
| Example 12 | 110 | 56.0 | A | A |
| Example 13 | 110 | 130.0 | A | A |
| Example 14 | 110 | 130.0 | A | B |
| Example 15 | 110 | 110.0 | A | B |
| Example 16 | 110 | 120.0 | A | A |
| Example 17 | 110 | 60.0 | A | A |
| Example 18 | 110 | 100.0 | A | A |
| Example 19 | 110 | 60.0 | A | B |
| Example 20 | 110 | 60.0 | A | B |
| Example 21 | 110 | 100.0 | A | B |
| Example 22 | 110 | 60.0 | A | B |
| Example 23 | 110 | 100.0 | A | B |
| Example 24 | 110 | 80.0 | A | B |
| Comparative Example 3 | 110 | 20.0 | C | C |
| Comparative Example 4 | 110 | — | C | C |

PEB: Temperature for heating after electron beam irradiation

In the result of Table 3, Examples 8 to 24 formed good patterns without pattern collapse. On the other hand, in Comparative Examples 3 and 4, formed 2×2 mm negative type resist patterns with smooth edges, but pattern peeling was observed in some.

INDUSTRIAL APPLICABILITY

The invention is preferably used in a cyclic compound represented by a specific chemical structural formula, which is useful as an acid amplification type non-polymer based resist material, a radiation-sensitive composition containing the same, and a resist pattern formation method using the radiation-sensitive composition.

What is claimed is:

1. A cyclic compound represented by the following formula (3):

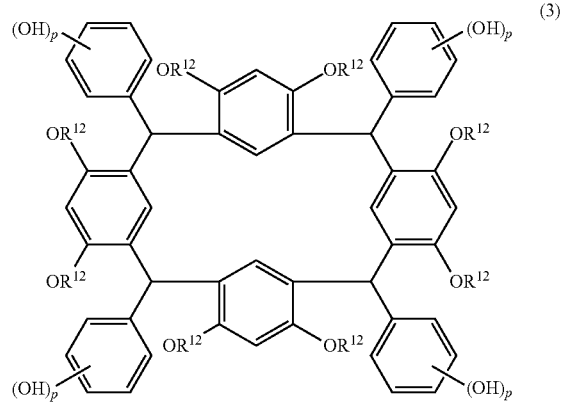

in the formula (3),
R$^{12}$ is independently a functional group selected from the group consisting of an alkyl group of 6 to 20 carbons, a cycloalkyl group of 3 to 20 carbons, an aryl group of 6 to 20 carbons, an alkylsilyl group of 1 to 20 carbons and an alkyl ester group of 2 to 20 carbons, or a hydrogen atom, wherein at least one of R$^{12}$ among them is a functional group selected from the group consisting of an alkyl group of 6 to 20 carbons, a cycloalkyl group of 3 to 20 carbons, an aryl group of 6 to 20 carbons, an alkylsilyl group of 1 to 20 carbons and an alkyl ester group of 2 to 20 carbons; and p is independently an integer of 1 to 5.

2. A cyclic compound according to claim 1, wherein in the formula (3), at least one of R$^{12}$ is a functional group selected from the group consisting of an alkyl group of 6 to 20 carbons, a cycloalkyl group of 6 to 20 carbons, an aryl group of 6 to 20 carbons, an alkylsilyl group of 1 to 20 carbons and an alkyl ester group of 2 to 20 carbons, and at least one other of R$^{12}$ is a hydrogen atom.

3. A cyclic compound according to claim 1, wherein the cyclic compound is represented by any of the isomers of the following formulae (3-1) to (3-4):

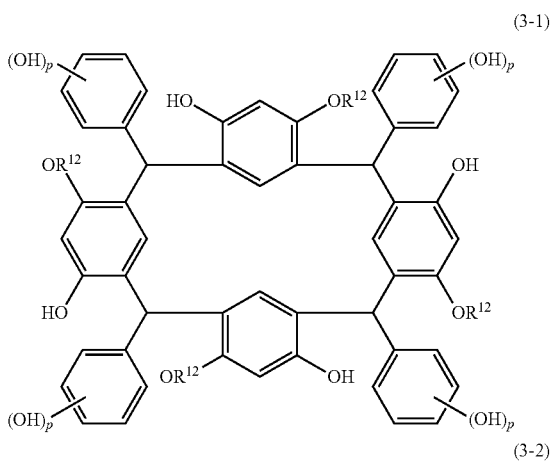

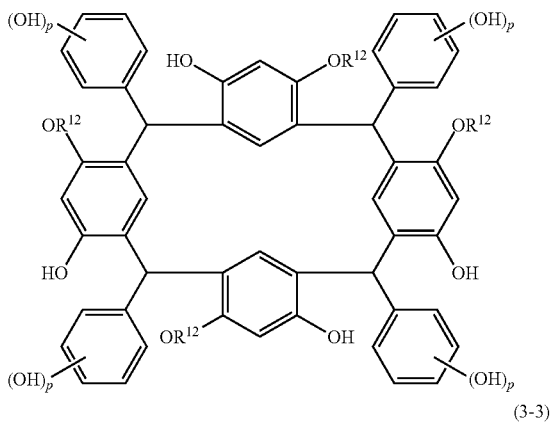

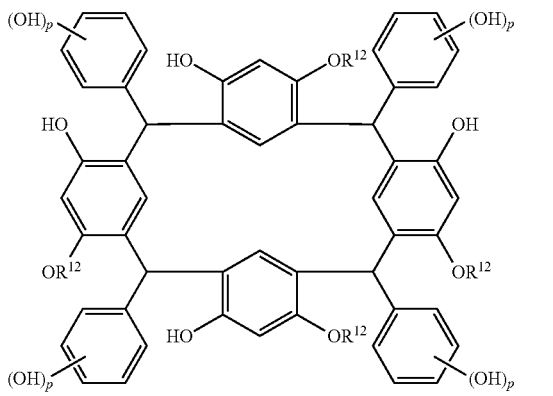

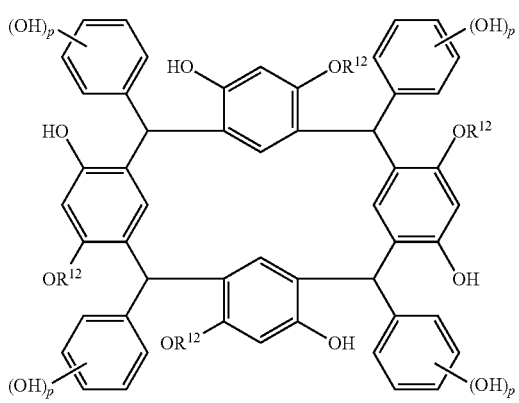

(3-4)

in the formulae (3-1) to (3-4), $R^{12}$ and p are the same as above.

4. A cyclic compound according to claim 1, wherein the cyclic compound is represented by any of the isomers of the following formulae (3'-1) to (3'-4):

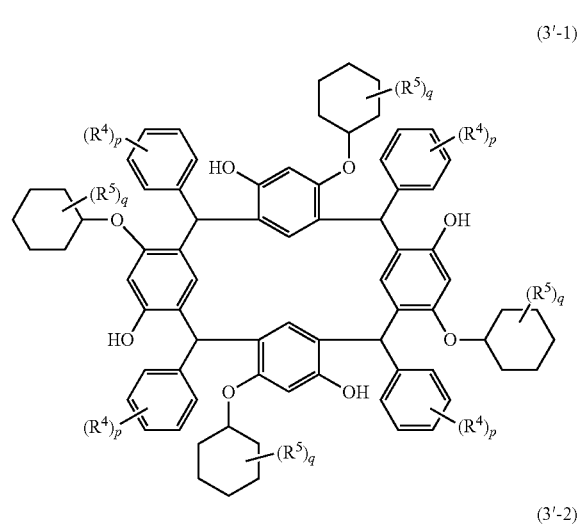

(3'-1)

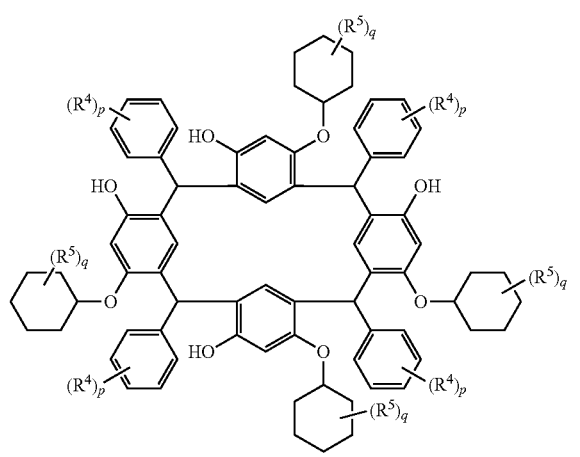

(3'-2)

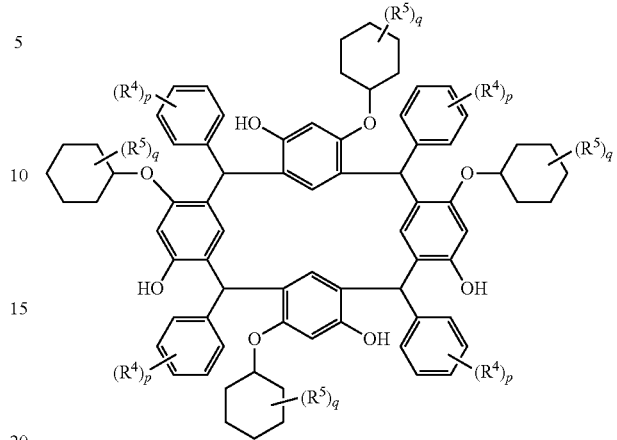

(3'-3)

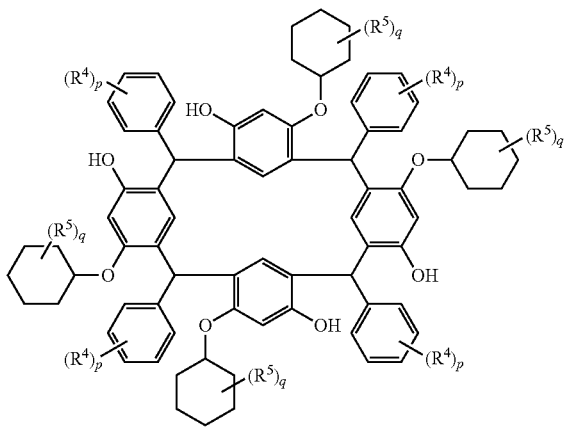

(3'-4)

in the formulae (3'-1) to (3'-4):

p is the same as above;

$R^4$ is a hydroxyl group; and $R^5$ is a functional group selected from the group consisting of an alkyl group of 1 to 3 carbons, a cycloalkyl group of 3 to 6 carbons, an aryl group of 6 to 14 carbons, an alkoxy group of 1 to 14 carbons, a cyano group, a nitro group, a heterocyclic group, a halogen atom, a carboxyl group, a hydroxyl group and an alkylsilyl group of 1 to 14 carbons, or a hydrogen atom, and q is independently an integer of 0 to 2.

5. A production process for a cyclic compound (A) represented by the formula (3) comprising a step of conducting a condensation reaction of one or more kinds selected from the group consisting of aromatic carbonyl compound (A1) and one or more kinds selected from the group consisting of phenolic compound (A2).

6. A production process according to claim 5, wherein the reaction temperature is 0 to 60° C.

* * * * *